(12) United States Patent
Luk et al.

(10) Patent No.: US 8,673,905 B2
(45) Date of Patent: Mar. 18, 2014

(54) IMIDAZO PYRAZINES

(75) Inventors: Kin-Chun Luk, North Caldwell, NJ (US); Michael Soth, Glen Rock, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 182 days.

(21) Appl. No.: 13/415,868

(22) Filed: Mar. 9, 2012

(65) Prior Publication Data

US 2012/0238564 A1    Sep. 20, 2012

Related U.S. Application Data

(60) Provisional application No. 61/453,601, filed on Mar. 17, 2011.

(51) Int. Cl.
| | | |
|---|---|---|
| *A61K 31/535* | (2006.01) | |
| *A61K 31/50* | (2006.01) | |
| *C07D 403/04* | (2006.01) | |
| *C07D 413/04* | (2006.01) | |
| *C07D 491/04* | (2006.01) | |

(52) U.S. Cl.
USPC ........ 514/233.2; 514/249; 544/117; 544/295; 544/350

(58) Field of Classification Search
USPC ............. 514/233.2, 249; 544/117, 295, 350
See application file for complete search history.

(56) References Cited

U.S. PATENT DOCUMENTS

| 2005/0009832 A1 | 1/2005 | Sun et al. | |
| 2007/0099925 A1 * | 5/2007 | Calderwood et al. | 514/249 |

FOREIGN PATENT DOCUMENTS

| WO | 2007/028081 | 3/2007 |
| WO | 2008/021781 | 2/2008 |
| WO | 2008/047307 | 4/2008 |
| WO | 2009/140128 | 11/2009 |

OTHER PUBLICATIONS

Chao et al., "J. Med. Chem." 52:7808-7816 ( 2009).
Fischer et al., "J. Clinical Oncol." 28:4339-4345 ( 2010).
Bouloc et al., "Bioorganic & Medicinal Chemistry Letters" 20:5988-5993 ( 2010).
Lumma et al., "Med. Chem." 26:357-363 ( 1983).
Kerekes et al., "J. Med. Chem." 54:201-210 ( 2011).
Sanz et al., "Current Opinion Oncol." 21:594-600 ( 2009).
Meurer et al., "J. Med. Chem." 35:3845-3857 ( 1992).
Ansel et al., "Pharmaceutical Dosage Forms & Drug Delivery Systems":456-457 ( 1995).
(International Search Report for PCT/EP2012/054415 Jun. 4, 2012).

* cited by examiner

*Primary Examiner* — James O Wilson
*Assistant Examiner* — Ebenezer O Sackey

(57) ABSTRACT

Compounds of formula

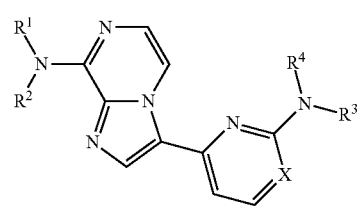

and pharmaceutically acceptable salts thereof are described, as well as the pharmaceutical compositions containing said compounds and their pharmaceutically acceptable salts, and the use of said compounds and pharmaceutical compositions for the treatment, control or amelioration of AML.

32 Claims, No Drawings

IMIDAZO PYRAZINES

PRIORITY TO RELATED APPLICATIONS

This application claims the benefit of U.S. Provisional Application No. 61/453,601, filed Mar. 17, 2011, which is hereby incorporated by reference in its entirety.

FIELD OF THE INVENTION

The present invention relates to imidazo[1,2-a]pyrazines which act as inhibitors of Fms-like tyrosine 3 (FLT3) and are useful in the amelioration, treatment or control of cancer, specifically acute myeloid leukemia (AML).

BACKGROUND OF THE INVENTION

Kinases are known to be important cellular enzymes that regulate cellular functions such as regulating cell division and proliferation. WO 2008/047307. Fms-like tyrosine 3 (FLT3) is a receptor tyrosine kinase (RTK) that is reported to be mutated in 25-30% of acute myeloid leukemia (AML) cases. See Miguel Sanz et al., "FLT3 inhibition as a targeted therapy for acute myeloid leukemia," Current Opinion Oncol. (2009) 21:594-600. Specifically, a mutation in the internal tandem duplication (ITD) of the fms-like tyrosine 3 (FLT3) gene is reported to be the second most common genetic change associated with cytogenetically normal AML. This mutation is indicated to be an important prognostic factor for this class of patients as mutations of the ITD are associated with poor disease prognosis. Sanz Id. FLT3 is thus a recognized molecular target for the development of new therapies for AML. Sanz id at 596; Qi Chao et al, "Identification of . . . (AC220), a Uniquely Potent, Selective and Efficacious FMS-Like Tyrosine Kinase-3 (FLT3) Inhibitor," J. Med. Chem. (2009) 52:7808-7816. Currently, there are a number of selective FLT3 inhibitors being investigated as treatments for AML (including tandutinib and AC220), and sunitinib, a multitargeted kinase inhibitor (including FLT3), has already been approved for sale. See Chao et al., id; Sanz et al., supra. Other inhibitors of FLT3 that are in development are discussed in Sanz, id, and Thomas Fischer et al., J Clinical Oncol. (2010) 28:4339-4345.

SUMMARY OF THE INVENTION

One aspect of the invention is a compound of formula I

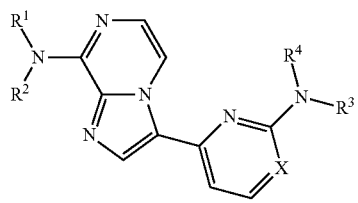

I or a pharmaceutically acceptable salt thereof, wherein X, $R^1$, $R^2$, $R^3$ and $R^4$ are as defined below.

The present invention also relates to pharmaceutical compositions comprising one or more compounds of the invention, or a pharmaceutically acceptable salt, and a pharmaceutically acceptable carrier or excipient.

The present invention further relates to a method of treating, ameliorating or controlling cancer, including specifically AML, comprising administering to a patient a therapeutically effective amount of a compound according to the invention or a pharmaceutically acceptable salt thereof.

DETAILED DESCRIPTION OF THE INVENTION

Definitions

As used herein, the following terms shall have the following definitions.

The terms "$C_{1-6}$ alkyl" or "$C_{1-4}$ alkyl" refer to straight- or branched-chain saturated hydrocarbon groups having from 1 to 6, or 1 to 4, carbon atoms, respectively. Examples of $C_{1-6}$ alkyl groups include, but are not limited to, methyl, ethyl, n-propyl, i-propyl, n-butyl, s-butyl, t-butyl, n-pentyl, and s-pentyl.

"Alkoxy, alkoxyl or lower alkoxy" refers to any of the above alkyl groups which is attached to the remainder of the molecule by an oxygen atom (RO—). Typical alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Aryl" means a substituted or unsubstituted monovalent, monocyclic or bicyclic, aromatic carboxylic hydrocarbon radical, preferably a 6-10 member aromatic ring system. Preferred aryl groups include, but are not limited to, phenyl, naphthyl, tolyl, and xylyl.

The term "cycloalkyl" as used herein means a substituted or unsubstituted stable monocyclic or polycyclic system which consists of carbon atoms only, all rings of which are saturated. Examples of cycloalkyls include, but are not limited to, cyclopropyl, cyclobutyl, cyclopentyl, cyclohexyl, cycloheptyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds.

"Halogen" means Cl, F and Br.

"Heteroaryl" means a substituted or unsubstituted aromatic heterocyclic ring system containing up to two rings. Preferred heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl and tetrazolyl.

In the case of a heteroaryl that is bicyclic it should be understood that one ring may be aryl while the other is heteroaryl and both may be independently substituted or unsubstituted.

"Hetero atom" means an atom selected from N, O and S.

"Heterocycle" or "heterocyclic ring" means a substituted or unsubstituted 5 to 10 membered, mono- or bicyclic, non-aromatic hydrocarbon, wherein 1 to 3 carbon atoms are replaced by a hetero atom selected from nitrogen, oxygen or sulfur atom. Examples include tetrahydropyran, pyrrolidinyl, including pyrrolidin-1-yl, pyrrolidin-2-yl and pyrrolidin-3-yl; piperazinyl; piperidinyl; morpholinyl, including morpholin-4-yl; and the like, which in turn can be substituted.

In the case of a heterocycle that is bicyclic it should be understood that one ring may be heterocycle while the other is cycloalkyl, and either or both may be independently substituted. An example of such a bicyclic heterocycle is 8-oxa-3-aza-bicyclo[3.2.1]octane.

Hydroxy or hydroxyl is a prefix indicating the presence of a monovalent —O—H group.

"IC$_{50}$" refers to the concentration of a particular compound required to inhibit 50% of a specific measured activity. IC$_{50}$ can be measured, inter alia, as is described subsequently in Examples 92 and 93.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, means that the substitution can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

In one embodiment, the present invention relates to compounds of formula I

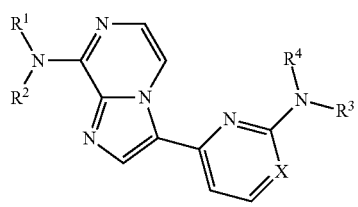

I wherein
X is selected from CH or N,
R$^1$ and R$^2$ are independently selected from the group consisting of
  (a) H,
  (b) C$_{1-4}$ alkyl,
  (c) C$_{1-4}$ alkyl substituted with up to 3 groups selected from cycloalkyl, heterocycle, OR$^5$, NR$^5$R$^6$, SO$_2$R$^7$ or CN,
  (d) heterocycle,
  (e) heterocycle substituted with up to three groups selected from C$_{1-4}$ alkyl, OR$^8$, NR$^8$R$^9$ or CN,
  (f) cycloalkyl, and
  (g) cycloalkyl substituted with up to three groups selected from C$_{1-4}$ alkyl, OR$^8$, NR$^8$R$^9$ or CN; or
alternatively, NR$^1$R$^2$ together can be a heterocycle that optionally may be substituted with C$_{1-4}$ alkyl;

R$^3$ is selected from the group consisting of
  (a) C$_{1-6}$ alkyl
  (b) C$_{1-6}$ alkyl substituted with up to 3 groups selected from
    aryl,
    aryl substituted with Cl, F, CH$_3$, or CF$_3$,
    heteroaryl,
    cycloalkyl,
    heterocycle,
    OH,
    OCH$_3$,
    NR$^8$R$^9$, and
    CN;
  (c) aryl,
  (d) aryl substituted with Cl, F, C$_{1-4}$ alkyl or CF$_3$,
  (e) heteroaryl,
  (f) cycloalkyl optionally substituted with OR$^5$, and
  (g) heterocycle;
R$^4$, R$^8$ and R$^9$ are independently selected from the group consisting of
  (a) H, and
  (b) C$_{1-4}$ alkyl; or
alternatively, NR$^3$R$^4$ together can be a heterocycle that optionally is substituted with C$_{1-4}$ alkyl;
R$^5$ and R$^6$ are independently selected from the group consisting of
  (a) H, and
  (b) C$_{1-4}$ alkyl; and
R$^7$ is selected from the group
  (a) C$_{1-4}$ alkyl, and
  (b) cycloalkyl;
or a pharmaceutically acceptable salt thereof.

In another embodiment, the invention relates to compounds of formula Ia having the structure

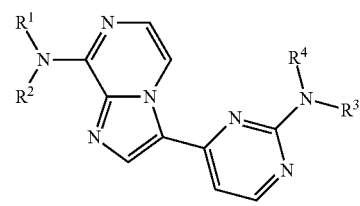

Ia wherein R$^1$, R$^2$, R$^3$ and R$^4$ are as defined above, or a pharmaceutically acceptable salt thereof.

In another embodiment, the invention relates to compounds of formula Ib having the structure

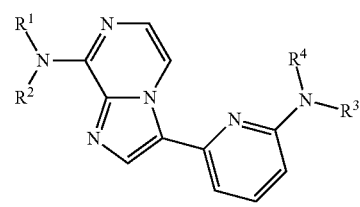

Ib wherein R$^1$, R$^2$, R$^3$ and R$^4$ are as defined above, or a pharmaceutically acceptable salt thereof.

In another embodiment, the invention relates to compounds of formula I, including compounds of formulas Ia and Ib, wherein R$^1$ is C$_{1-4}$ alkyl, or a pharmaceutically acceptable salt thereof.

In another embodiment, the invention relates to compounds of formula I, including compounds of formulas Ia and Ib, wherein $R^1$ is $C_{1-4}$ alkyl that optionally is substituted with a heterocycle, or a pharmaceutically acceptable salt thereof.

In another embodiment, the invention relates to compounds of formula I, including compounds of formulas Ia and Ib, wherein $R^1$ is $C_{1-4}$ alkyl that optionally is substituted with $OR^5$, including specifically OH, or a pharmaceutically acceptable salt thereof.

In another embodiment, the invention relates to compounds of formula I, including compounds of formulas Ia and Ib, wherein $R^1$ is $C_{1-4}$ alkyl that optionally is substituted with $SO_2R^7$, or a pharmaceutically acceptable salt thereof. In an embodiment $R^7$ is $C_{1-4}$ alkyl, specifically methyl, or a pharmaceutically acceptable salt thereof.

In another embodiment, the invention relates to compounds of formula I, including compounds of formulas Ia and Ib, wherein $R^1$ is cycloalkyl, or a pharmaceutically acceptable salt thereof.

In another embodiment, the invention relates to compounds of formula I, including compounds of formulas Ia and Ib, wherein $R^1$ is cycloalkyl that is substituted with $NR^8R^9$, including specifically $NH_2$, or a pharmaceutically acceptable salt thereof.

In another embodiment, the invention relates to compounds of formula I, including compounds of formulas Ia and Ib, wherein $R^1$ is heterocycle, including specifically piperidine and morpholine, or a pharmaceutically acceptable salt thereof.

Another embodiment of the invention relates to compounds of Formula I, including compounds of formulas Ia and Ib, wherein $R^1$ is as defined immediately above and $R^2$ is H, or a pharmaceutically acceptable salt thereof.

Another embodiment of the invention relates to compounds of Formula I, including compounds of formulas Ia and Ib, wherein $R^1$ is as defined immediately above and $R^2$ is $C_{1-4}$ alkyl, or a pharmaceutically acceptable salt thereof.

Another embodiment of the invention relates to compounds of Formula I, including compounds of formulas Ia and Ib, $NR^1R^2$ together are a heterocycle, including specifically piperazine, that optionally may be substituted with $C_{1-4}$ alkyl, including specifically methyl, or a pharmaceutically acceptable salt thereof.

Another embodiment of the invention relates to compounds of Formula I, including compounds of formulas Ia and Ib, wherein $R^1$ and $R^2$ are as defined immediately above and $R^3$ is $C_{1-6}$ alkyl, specifically $C_{1-4}$ alkyl, or a pharmaceutically acceptable salt thereof.

Another embodiment of the invention relates to compounds of Formula I, including compounds of formulas Ia and Ib, wherein $R^1$ and $R^2$ are as defined immediately above and $R^3$ is $C_{1-4}$ alkyl that is substituted with up to 2 groups selected from $NH_2$, thiophene and phenyl, or a pharmaceutically acceptable salt thereof. The phenyl group optionally may substituted with Cl.

Another embodiment of the invention relates to compounds of Formula I, including compounds of formulas Ia and Ib, wherein $R^1$ and $R^2$ are as defined immediately above and $R^3$ is cycloalkyl, including specifically cyclohexane, that optionally may be substituted with OH, or a pharmaceutically acceptable salt thereof.

Another embodiment of the invention relates to compounds of Formula I, including compounds of formulas Ia and Ib, wherein $R^1$ and $R^2$ are as defined immediately above and $R^3$ is aryl, including specifically phenyl, or a pharmaceutically acceptable salt thereof.

Another embodiment of the invention relates to compounds of Formula I, including compounds of formulas Ia and Ib, wherein $R^1$ and $R^2$ are as defined immediately above and $R^3$ is heterocycle, specifically tetrahydropyran or morpholine, or a pharmaceutically acceptable salt thereof.

Another embodiment of the invention relates to compounds of Formula I, including compounds of formulas Ia and Ib, wherein $R^1$, $R^2$ and $R^3$ are as defined immediately above and $R^4$ is H, or a pharmaceutically acceptable salt thereof.

Another embodiment of the invention relates to compounds of Formula I, including compounds of formulas Ia and Ib, wherein $R^1$ and $R^2$ are as defined immediately above and $NR^3R^4$ together form a heterocycle, including specifically morpholine and piperazine, said heterocycle optionally being substituted by $C_{1-4}$ alkyl, including specifically methyl, or a pharmaceutically acceptable salt thereof.

Another embodiment of the invention relates to compounds of Formula I, including compounds of formulas Ia and Ib, wherein $R^1$, $R^2$, $R^3$ and $R^4$ are as defined immediately above and $R^5$ and $R^6$ are independently H or $CH_3$, or a pharmaceutically acceptable salt thereof.

Another embodiment of the invention relates to compounds of Formula I, including compounds of formulas Ia and Ib, wherein $R^1$, $R^2$, $R^3$, $R^4$, $R^5$ and $R^6$ are as defined immediately above and $R^7$, $R^8$ and $R^9$ are independently selected from a $C_{1-4}$ alkyl group, including specifically methyl, or a pharmaceutically acceptable salt thereof.

It is contemplated herein that salts of compounds of formula I such as hydrochloride or trifluoroacetic acid salts include salts with multiple conjugates such as mono HCl, di-HCl, etc.

Compounds according to the invention include:
Isopropyl-[3-(2-phenylamino-pyrimidin-4-yl)-imidazo[1,2-a]pyrazin-8-yl]-amine (Example 12);
2-[3-(2-Phenylamino-pyrimidin-4-yl)-imidazo[1,2-a]pyrazin-8-ylamino]-ethanol (Example 13);
(2-Methanesulfonyl-ethyl)-{3-[2-(tetrahydro-pyran-4-ylamino)-pyrimidin-4-yl]-imidazo[1,2-a]pyrazin-8-yl}-amine (Example 14);
(2-Methanesulfonyl-ethyl)-[3-(2-morpholin-4-yl-pyrimidin-4-yl)-imidazo[1,2-a]pyrazin-8-yl]-amine (Example 15);
[3-(2-Isopropylamino-pyrimidin-4-yl)-imidazo[1,2-a]pyrazin-8-yl]-(2-methanesulfonyl-ethyl)-amine (Example 16);
4-[4-(8-Isopropylamino-imidazo[1,2-a]pyrazin-3-yl)-pyrimidin-2-ylamino]-cyclohexanol (Example 17);
Isopropyl-{3-[2-(tetrahydro-pyran-4-ylamino)-pyrimidin-4-yl]-imidazo[1,2-a]pyrazin-8-yl}-amine (Example 18);
Isopropyl-[3-(2-morpholin-4-yl-pyrimidin-4-yl)-imidazo[1,2-a]pyrazin-8-yl]-amine (Example 19);
Methyl-[3-(2-phenylamino-pyrimidin-4-yl)-imidazo[1,2-a]pyrazin-8-yl]-amine (Example 20);
Methyl-[3-(2-morpholin-4-yl-pyrimidin-4-yl)-imidazo[1,2-a]pyrazin-8-yl]-amine (Example 21);
Piperidin-4-yl-{3-[2-(tetrahydro-pyran-4-ylamino)-pyrimidin-4-yl]-imidazo[1,2-a]pyrazin-8-yl}-amine (Example 22);
[3-(2-Morpholin-4-yl-pyrimidin-4-yl)-imidazo[1,2-a]pyrazin-8-yl]-piperidin-4-yl-amine (Example 23);
[3-(2-Isopropylamino-pyrimidin-4-yl)-imidazo[1,2-a]pyrazin-8-yl]-piperidin-4-yl-amine (Example 24);
Isopropyl-[3-(2-isopropylamino-pyrimidin-4-yl)-imidazo[1,2-a]pyrazin-8-yl]-amine (Example 25);
[3-(2-Methylamino-pyrimidin-4-yl)-imidazo[1,2-a]pyrazin-8-yl]-piperidin-4-yl-amine (Example 26);

4-{4-[8-(2-Methanesulfonyl-ethylamino)-imidazo[1,2-a]
pyrazin-3-yl]-pyrimidin-2-ylamino}-cyclohexanol (Example 27);
2-{3-[2-(Tetrahydro-pyran-4-ylamino)-pyrimidin-4-yl]-imidazo[1,2-a]pyrazin-8-ylamino}-ethanol (Example 28);
2-[3-(2-Morpholin-4-yl-pyrimidin-4-yl)-imidazo[1,2-a]
pyrazin-8-ylamino]-ethanol (Example 29);
2-[3-(2-Isopropylamino-pyrimidin-4-yl)-imidazo[1,2-a]
pyrazin-8-ylamino]-ethanol (Example 30);
2-[3-(2-Methylamino-pyrimidin-4-yl)-imidazo[1,2-a]
pyrazin-8-ylamino]-ethanol (Example 31);
Isopropyl-[3-(2-methylamino-pyrimidin-4-yl)-imidazo[1,2-a]pyrazin-8-yl]-amine (Example 32);
(2-Methanesulfonyl-ethyl)-[3-(2-methylamino-pyrimidin-4-yl)-imidazo[1,2-a]pyrazin-8-yl]-amine (Example 33);
Methyl-{3-[2-(tetrahydro-pyran-4-ylamino)-pyrimidin-4-yl]-imidazo[1,2-a]pyrazin-8-yl}-amine (Example 34);
Methyl-[3-(2-methylamino-pyrimidin-4-yl)-imidazo[1,2-a]
pyrazin-8-yl]-amine (Example 35);
N1-{4-[8-(4-Methyl-piperazin-1-yl)-imidazo[1,2-a]pyrazin-3-yl]-pyrimidin-2-yl}-1-phenyl-ethane-1,2-diamine;
hydrochloride (Example 52);
N1-{4-[8-(4-Methyl-piperazin-1-yl)-imidazo[1,2-a]pyrazin-3-yl]-pyrimidin-2-yl}-1-phenyl-propane-1,3-diamine;
hydrochloride (Example 54);
N1-{6-[8-(4-Methyl-piperazin-1-yl)-imidazo[1,2-a]pyrazin-3-yl]-pyridin-2-yl}-1-phenyl-ethane-1,2-diamine; hydrochloride (Example 55);
Benzyl-{6-[8-(4-methyl-piperazin-1-yl)-imidazo[1,2-a]
pyrazin-3-yl]-pyridin-2-yl}-amine (Example 56);
Benzyl-{4-[8-(4-methyl-piperazin-1-yl)-imidazo[1,2-a]
pyrazin-3-yl]-pyrimidin-2-yl}-amine (Example 57);
(2-Chloro-benzyl)-{4-[8-(4-methyl-piperazin-1-yl)-imidazo[1,2-a]pyrazin-3-yl]-pyrimidin-2-yl}-amine; hydrochloride (Example 58);
(4-Chloro-benzyl)-{4-[8-(4-methyl-piperazin-1-yl)-imidazo[1,2-a]pyrazin-3-yl]-pyrimidin-2-yl}-amine; hydrochloride (Example 59);
N1-{6-[8-(4-Methyl-piperazin-1-yl)-imidazo[1,2-a]pyrazin-3-yl]-pyridin-2-yl}-1-phenyl-propane-1,3-diamine;
hydrochloride (Example 60);
{4-[8-(4-Methyl-piperazin-1-yl)-imidazo[1,2-a]pyrazin-3-yl]-pyrimidin-2-yl}-thiophen-3-ylmethyl-amine (Example 61);
1-(3-Chloro-phenyl)-N-1-{4-[8-(4-methyl-piperazin-1-yl)-imidazo[1,2-a]pyrazin-3-yl]-pyrimidin-2-yl}-propane-1,3-diamine; hydrochloride (Example 63);
{4-[8-(4-Methyl-piperazin-1-yl)-imidazo[1,2-a]pyrazin-3-yl]-pyrimidin-2-yl}-thiophen-2-ylmethyl-amine; hydrochloride (Example 64);
(2-Chloro-benzyl)-{6-[8-(4-methyl-piperazin-1-yl)-imidazo[1,2-a]pyrazin-3-yl]-pyridin-2-yl}-amine; hydrochloride (Example 65);
(3-Chloro-benzyl)-{4-[8-(4-methyl-piperazin-1-yl)-imidazo[1,2-a]pyrazin-3-yl]-pyrimidin-2-yl}-amine; hydrochloride (Example 66);
N-{3-[2-(3-Chloro-benzylamino)-pyrimidin-4-yl]-imidazo[1,2-a]pyrazin-8-yl}-cyclohexane-1,4-diamine; hydrochloride (Example 67);
N-[3-(2-Benzylamino-pyrimidin-4-yl)-imidazo[1,2-a]
pyrazin-8-yl]-cyclohexane-1,4-diamine; hydrochloride (Example 68);
N1-{4-[8-(4-Methyl-piperazin-1-yl)-imidazo[1,2-a]pyrazin-3-yl]-pyrimidin-2-yl}-1-thiophen-3-yl-propane-1,3-diamine; hydrochloride (Example 70);
(4-Chloro-benzyl)-{6-[8-(4-methyl-piperazin-1-yl)-imidazo[1,2-a]pyrazin-3-yl]-pyridin-2-yl}-amine; hydrochloride (Example 71);
[3-(2-Benzylamino-pyrimidin-4-yl)-imidazo[1,2-a]pyrazin-8-yl]-(2-morpholin-4-yl-ethyl)-amine; hydrochloride (Example 72);
N-[3-(6-Benzylamino-pyridin-2-yl)-imidazo[1,2-a]pyrazin-8-yl]-cyclohexane-1,4-diamine; hydrochloride (Example 73);
N1-{4-[8-(4-Methyl-piperazin-1-yl)-imidazo[1,2-a]
pyrazin-3-yl]-pyrimidin-2-yl}-1-thiophen-3-yl-ethane-1,2-diamine; hydrochloride (Example 75);
N-{3-[2-(3-Amino-1-phenyl-propylamino)-pyrimidin-4-yl]-imidazo[1,2-a]pyrazin-8-yl}-cyclohexane-1,4-diamine;
hydrochloride (Example 76);
N-{3-[2-(2-Amino-1-phenyl-ethylamino)-pyrimidin-4-yl]-imidazo[1,2-a]pyrazin-8-yl}-cyclohexane-1,4-diamine;
hydrochloride (Example 77);
1-(3-Chloro-phenyl)-N-1-{4-[8-(4-methyl-piperazin-1-yl)-imidazo[1,2-a]pyrazin-3-yl]-pyrimidin-2-yl}-ethane-1,2-diamine; hydrochloride (Example 79);
N-{3-[6-(2-Amino-1-phenyl-ethylamino)-pyridin-2-yl]-imidazo[1,2-a]pyrazin-8-yl}-cyclohexane-1,4-diamine;
hydrochloride (Example 80);
N-{3-[6-(3-Amino-1-phenyl-propylamino)-pyridin-2-yl]-imidazo[1,2-a]pyrazin-8-yl}-cyclohexane-1,4-diamine;
hydrochloride (Example 81);
N-{3-[6-(3-Chloro-benzylamino)-pyridin-2-yl]-imidazo[1,2-a]pyrazin-8-yl}-cyclohexane-1,4-diamine; hydrochloride (Example 82);
N-{3-[2-(2-Chloro-benzylamino)-pyrimidin-4-yl]-imidazo[1,2-a]pyrazin-8-yl}-cyclohexane-1,4-diamine; hydrochloride (Example 83);
N-(3-{6-[(Thiophen-3-ylmethyl)-amino]-pyridin-2-yl}-imidazo[1,2-a]pyrazin-8-yl)-cyclohexane-1,4-diamine;
hydrochloride (Example 84);
N-{3-[6-(2-Chloro-benzylamino)-pyridin-2-yl]-imidazo[1,2-a]pyrazin-8-yl}-cyclohexane-1,4-diamine; hydrochloride (Example 85);
N-{3-[6-(4-Chloro-benzylamino)-pyridin-2-yl]-imidazo[1,2-a]pyrazin-8-yl}-cyclohexane-1,4-diamine; hydrochloride (Example 86);
N-(3-{6-[(Thiophen-2-ylmethyl)-amino]-pyridin-2-yl}-imidazo[1,2-a]pyrazin-8-yl)-cyclohexane-1,4-diamine;
hydrochloride (Example 87);
{3-[2-(2-Chloro-benzylamino)-pyrimidin-4-yl]-imidazo[1,2-a]pyrazin-8-yl}-(2-morpholin-4-yl-ethyl)-amine;
hydrochloride (Example 88);
{3-[2-(3-Chloro-benzylamino)-pyrimidin-4-yl]-imidazo[1,2-a]pyrazin-8-yl}-(2-morpholin-4-yl-ethyl)-amine;
hydrochloride (Example 89);
1-(3-Chloro-phenyl)-N-1-{6-[8-(2-morpholin-4-yl-ethylamino)-imidazo[1,2-a]pyrazin-3-yl]-pyridin-2-yl}-propane-1,3-diamine hydrochloride (Example 90); and
1-(3-Chloro-phenyl)-N-1-{6-[8-(2-morpholin-4-yl-ethylamino)-imidazo[1,2-a]pyrazin-3-yl]-pyridin-2-yl}-ethane-1,2-diamine hydrochloride (Example 91);
and the pharmaceutically acceptable salts of the foregoing compounds.

The compounds of formula I, as well as their salts, that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the present invention are inhibitors of FLT3 and are useful in the treatment, amelioration or control of cell proliferative disorders, in particular chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are anticipated to be particularly useful in the treatment or control of acute myeloid leukemia (AML).

A "therapeutically effective amount" or "effective amount" of a compound in accordance with this invention means an amount of compound that is effective to alleviate, ameliorate or control symptoms of disease or prolong the survival of the subject being treated.

The therapeutically effective amount or dosage of a compound according to this invention can vary within wide limits. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

The pharmaceutical preparations of the invention can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

General Synthesis of the Compounds According to the Invention

The present invention also provides methods for the synthesis of imidazol[1,2-a]pyrazines of the invention.

The compounds of the invention can be prepared by processes known in the art. Suitable processes for synthesizing these compounds are also provided in the examples. Generally, compounds of formula I can be synthesized according to one of the below described synthetic routes.

The starting materials are either commercially available or can be synthesized by methods known in the art. Compounds of formula Ia where X is N can be synthesized starting from the known 3-bromo-8-chloro-imidazo[1,2-a]pyrazine (4). Lumma, Jr., W. C.; Randall, W. C.; Cresson, E. L.; Huff, J. R.; Hartman, R. D.; Lyon, T. F. *J. Med. Chem.* 1983, 26, 357-363. Meurer, L. C.; Tolman, R. L.; Chapin, E. W.; Saperstein, R.; Vicario, P. P.; Zrada, M. M.; MacCoss, M. *J. Med. Chem.* 1992, 35, 3845-3857. In accordance to Scheme 1 below, 2-amino-3-chloropyrazine (1) can be reacted with 2-bromo-1,1-dimethoxy-ethane (2) to give 8-chloro-imidazo[1,2-a]pyrazine (3) which can be brominated to give 3-bromo-8-chloro-imidazo[1,2-a]pyrazine (4). Compound 4 can be reacted with an appropriate amine (HNR$^1$R$^2$) either in excess or in the presence of another base, such as diisopropyl ethyl amine, in an appropriate solvent, such as ethanol or butanol, between room temperature to reflux to give compound 5. Compound 5 can than be condensed with 2-methylsulfanyl-4-tributylstannanyl-pyrimidine (6) in the presence of a suitable palladium catalyst to give intermediate 7.

In cases of certain amines that contained additional functional groups, appropriate protecting groups (for example tert-butoxy-carbonyl group) may be employed to facilitate synthesis. If such protecting groups are employed, the removal of such protecting groups to generate the compounds of the invention can be accomplished by standard methods known to those skilled in the art of organic synthesis.

Scheme 1

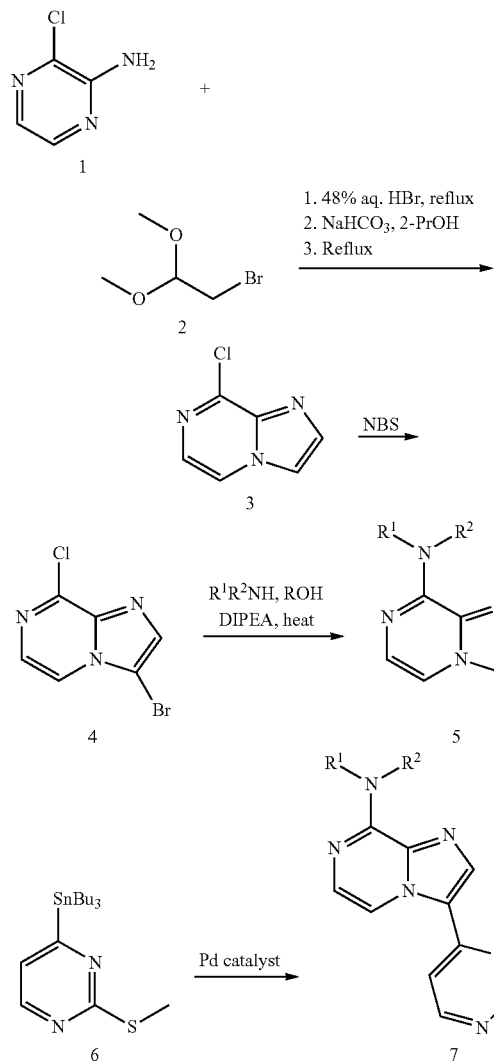

Scheme 2

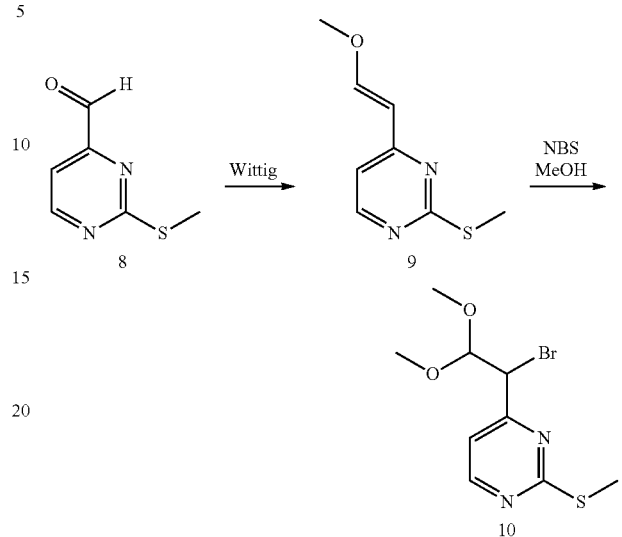

Scheme 3

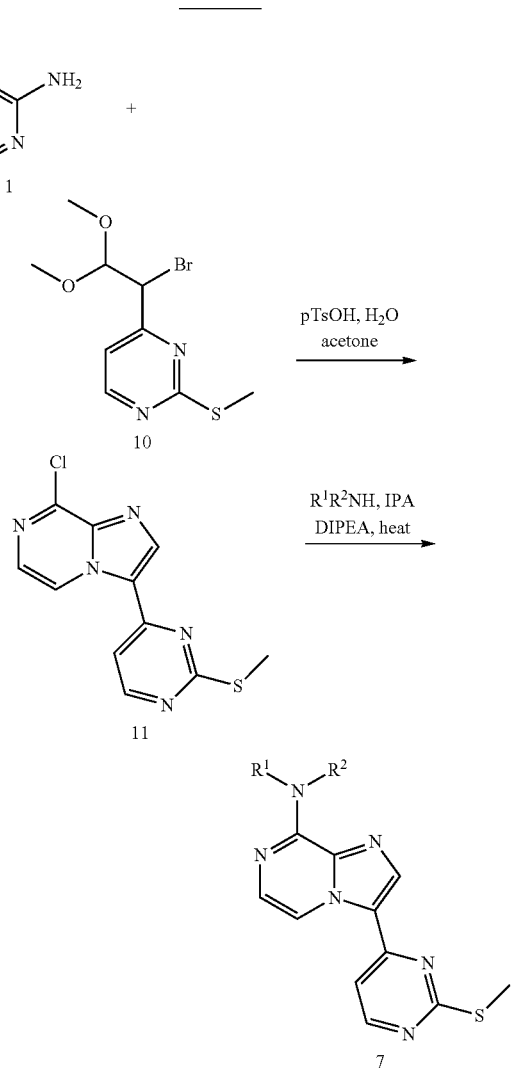

provides the ethyl homolog 10'. Homolog 10' can be converted to intermediate 7 in the same way as 10.

Alternatively, intermediate 7 used in the synthesis of compounds of formula Ia can be prepared according to Schemes 2-4 below. 2-Methylsulfanyl-pyrimidine-4-carbaldehyde (8) can be condensed with (methoxymethyl)triphenylphosphonium chloride (Wittig reaction) to give 4-(2-methoxy-vinyl)-2-methylsulfanyl-pyrimidine (9). Oxidation of (9) with N-bromosuccinimide in methanol provides 4-(1-bromo-2,2-dimethoxy-ethyl)-2-methylsulfanyl-pyrimidine (10). Condensation of (10) with 2-amino-3-chloropyrazine (1) in aqueous acid and a co-solvent such as acetone gives 8-chloro-3-(2-methylsulfanyl-pyrimidin-4-yl)-imidazo[1,2-a]pyrazine (11). Compound 11 can then be reacted with an appropriate amine ($HNR^1R^2$) either in excess or in the presence of another base, such as diisopropyl ethyl amine, in an appropriate solvent, such as ethanol or butanol, between room temperature to reflux to give the intermediate 7. Intermediate 7 can also be prepared via the ethyl homologs 9' and 10' according to Scheme 4 below. Compound 9' (the ethyl homolog) can be prepared by the reaction ethyl ethynyl ether (13) with borane—tetrahydrofuran complex followed by palladium catalyzed coupling with 4-chloro-2-(methylthio)pyrimidine (12). Oxidation of 9' with N-bromosuccinimide in ethanol

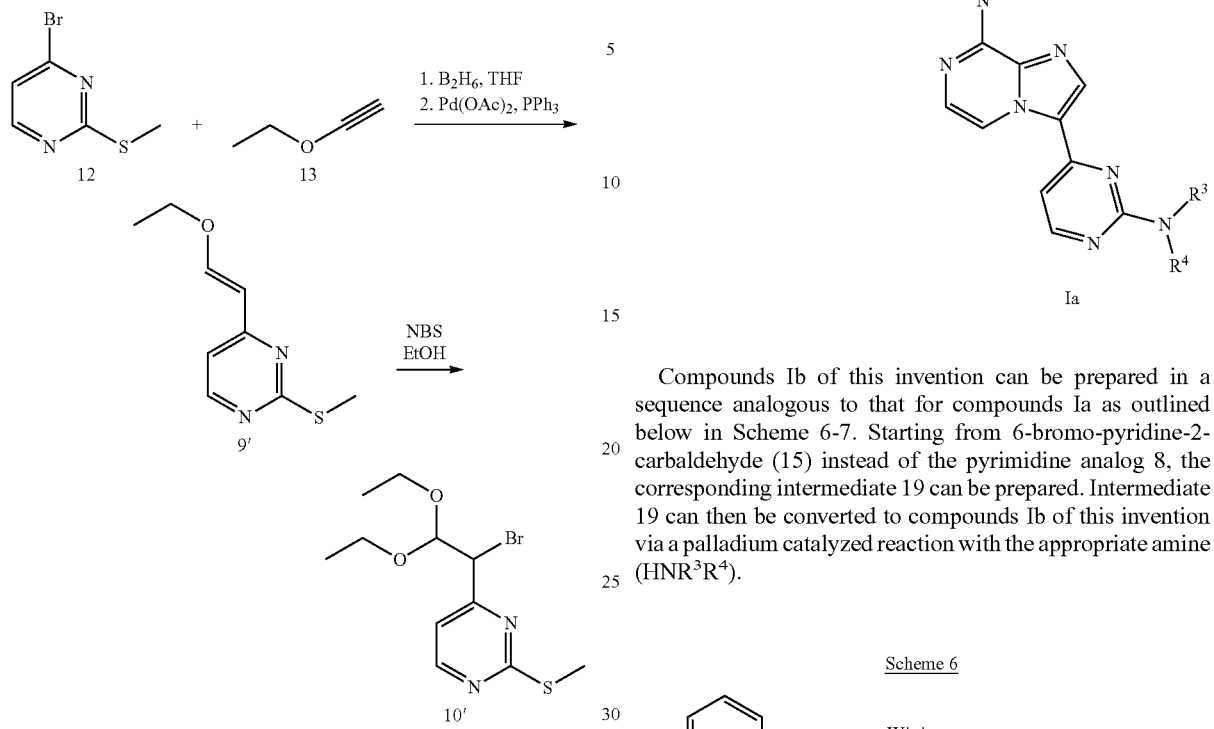

Intermediate 7 can be converted to compounds Ia of this invention by following Scheme 5 below. After oxidation with a suitable oxidant, such as a per acid or Oxone, to give either the sulfoxide (14, n=1) or sulfone (14, n=2), the resulting sulfoxide or sulfone 14 can be converted to compounds Ia of this invention by heating it with the appropriate amine ($HNR^3R^4$).

Compounds Ib of this invention can be prepared in a sequence analogous to that for compounds Ia as outlined below in Scheme 6-7. Starting from 6-bromo-pyridine-2-carbaldehyde (15) instead of the pyrimidine analog 8, the corresponding intermediate 19 can be prepared. Intermediate 19 can then be converted to compounds Ib of this invention via a palladium catalyzed reaction with the appropriate amine ($HNR^3R^4$).

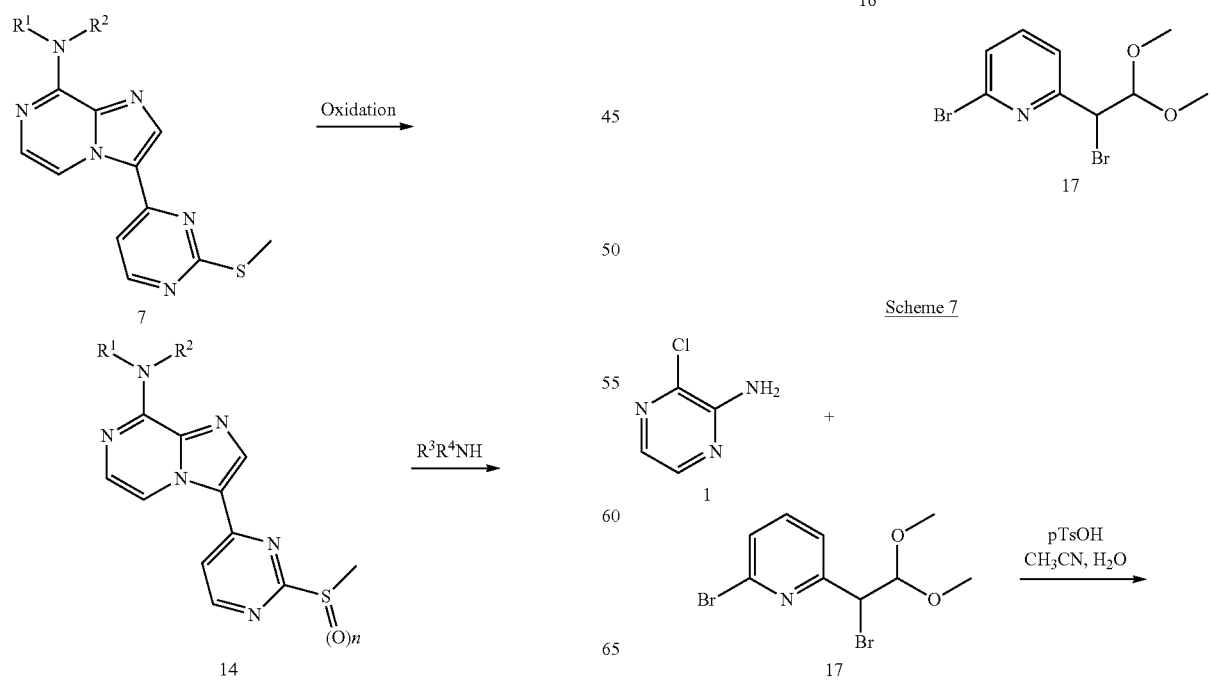

-continued

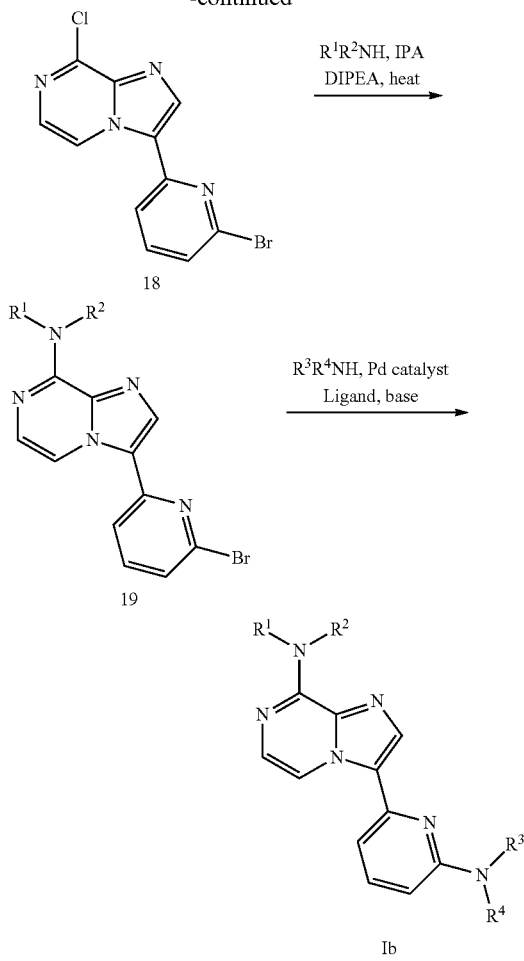

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2, (function in ISIS Draw, Elsevier/MDL), or AutoNom 2000 TT v4.01.305 (Elsevier/MDL), or functions available in ChemDraw Pro Control 11.0.2 (CambridgeSoft Corp.).

Abbreviations Used In The Examples
ATP adenosine triphosphate
Boc$_2$O di-tert-butyl dicarbonate
"BuOH n-butanol
CDCl$_3$ chloroform-d
CD$_3$OD deuterated methanol
CH$_2$Cl$_2$ dichloromethane
CH$_3$CN acetonitrile
CH$_3$OH methanol
CO$_2$ carbon dioxide
DCM dichloromethane
DEAD diethyl azodicarboxylate
DIPE diisopropyl ether
DIPEA N,N-diisopropylethylamine
DMAP 4-(dimethylamino)pyridine
DMF N,N-dimethylformamide
DMSO dimethylsulfoxide
DMSO-d$_6$ deuterated dimethylsulfoxide
Et$_3$N triethylamine
Et$_2$O diethyl ether
EtOAc ethyl acetate
EtOH ethanol
FBS fetal bovine serum
HCl hydrogen chloride
Concentrated HCl concentrated hydrochloric acid
H$_2$O water
HPLC high performance liquid chromatography
iPrOH 2-propanol
LAH lithium aluminum hydride
LC-MS liquid chromatography-mass spectroscopy
LDA lithium diisopropylamide
LiAlH$_4$ lithium aluminum hydride
KCN potassium cyanide
K$_2$CO$_3$ potassium carbonate
mCPBA meta-chloro-perbenzoic acid
MeCN acetonitrile
MeOH methanol
MgCl$_2$ magnesium chloride
MgSO$_4$ magnesium sulfate
N$_2$ nitrogen gas
NaHCO$_3$ sodium bicarbonate
NaOH sodium hydroxide
NaOtBu sodium t-butoxide
Na$_2$SO$_4$ sodium sulfate
NH$_3$ ammonia
Pd$_2$(dba)$_3$ tris(dibenzylideneacetone)dipalladium(0)
PPh$_3$ triphenylphosphine
TFA trifluoroacetic acid
THF tetrahydrofuran
TLC thin layer chromatography The following starting materials were purchased from the sources listed below.
LDA Sigma-Aldrich (Shanghai) Trading Co., Ltd
Ethyl ethynyl ether Alfa Aesar China (Tianjin) Co., Ltd.
borane tetrahedrofuran Alfa Aesar China (Tianjin) Co., Ltd.
Oxone Beijing huaxue shiji
(Methoxymethyl)triphenylphosphonium chloride Alfa Aesar China (Tianjin) Co., Ltd.
4-chloro-2-(methylthio)pyrimidine Alfa Aesar China (Tianjin) Co., Ltd.
1,1'-Bis(diphenylphosphino)ferrocene Shanghai Aopudishi
2-dicyclohexylphosphino-2(N,N-dimethylamino)biphenyl Alfa Aesar China (Tianjin) Co., Ltd.
X-Phos Alfa Aesar China (Tianjin) Co., Ltd.
1,1'-bis(diphenylphosphino)ferrocene)dichloropalladium Shanghai Aopudishi
2-Amino-3-chloropyrazine Alfa Aesar China (Tianjin) Co., Ltd.
2-Chlorobenzylamine Alfa Aesar China (Tianjin) Co., Ltd.
3-Chlorobenzylamine Alfa Aesar China (Tianjin) Co., Ltd.
4-Chlorobenzylamine Alfa Aesar China (Tianjin) Co., Ltd.
2-Thiophenemethylamine Alfa Aesar China (Tianjin) Co., Ltd.

2-Methylsulfanyl-pyrimidine-4-carbaldehyde Alfa Aesar China (Tianjin) Co., Ltd.
4-(2-Aminoethyl)morpholine Alfa Aesar China (Tianjin) Co., Ltd.
Triphenylphosphine Beijing huaxue shiji
N-Bromosuccinimide Beijing Ouhe
3-Chloroperoxybenzoic acid Beijing Ouhe
Phosphorus oxychloride Beijing Huagong
p-Toluenesulfonic acid Beijing Huagong
2-(Methylthio)-4-(tributylstannyl)pyrimidine Alfa Aesar Example 1

3-Bromo-8-chloro-imidazo[1,2-a]pyrazine

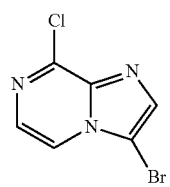 [SMILES: Clc1nccn2c(Br)cnc12]

3-Bromo-8-chloro-imidazo[1,2-a]pyrazine was prepared according to the procedures of Lumma, Jr., W. C.; Randall, W. C.; Cresson, E. L.; Huff, J. R.; Hartman, R. D.; Lyon, T. F. *J. Med. Chem.* 1983, 26, 357-363. Meurer, L. C.; Tolman, R. L.; Chapin, E. W.; Saperstein, R.; Vicario, P. P.; Zrada, M. M.; MacCoss, M. *J. Med. Chem.* 1992, 35, 3845-3857.

Example 2

2-(3-Bromo-imidazo[1,2-a]pyrazin-8-ylamino)-ethanol

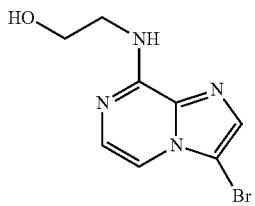 [SMILES: OCCNc1nccn2c(Br)cnc12]

3-Bromo-8-chloro-imidazo[1,2-a]pyrazine (0.70 g, 3.0 mmol) (from Example 1 supra) was stirred in ″BuOH (10 mL) and ethanolamine (0.22 mL, 3.65 mmol) followed by Hunig's base (1.04 mL, 6.0 mmol) Reaction mixture was then heated at 100° C. overnight. The mixture was concentrated to dryness and water was added (150 mL) followed by a saturated aqueous solution of NaHCO$_3$ (50 mL). The reaction was then extracted with EtOAc (3×20 mL) and the organic phases were combined, washed with water (2×20 mL), dried over MgSO$_4$ and concentrated to dryness to give 2-(3-bromo-imidazo[1, 2-a]pyrazin-8-ylamino)-ethanol. (Yield 0.59 g, 77%). $^1$H (400 MHz; DMSO-d$_6$) δ 3.52-3.56 (2 H, m), 3.58-3.62 (2 H, m), 4.79 (1 H, t, J=5.4 Hz), 7.42 (2 H, d, J=5 Hz), 7.56 (1 H, d, J=5 Hz), 7.66 (1 H, s).

Example 3

(3-Bromo-imidazo[1,2-a]pyrazin-8-yl)-(2-methylsulfanyl-ethyl)-amine

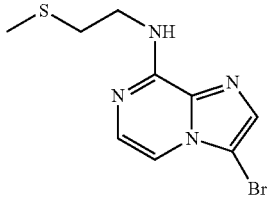

(3-Bromo-imidazo[1,2-a]pyrazin-8-yl)-(2-methylsulfanyl-ethyl)-amine was prepared by a process analogous to that described in Example 2 starting from 3-bromo-8-chloro-imidazo[1,2-a]pyrazine and 2-methylsulfanyl-ethylamine.

Example 4

(3-Bromo-imidazo[1,2-a]pyrazin-8-yl)-(2-methylsulfanyl-ethyl)-carbamic acid tert-butyl ester

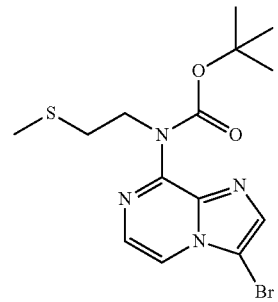 [SMILES: CSCCN(C(=O)OC(C)(C)C)c1nccn2c(Br)cnc12]

(3-Bromo-imidazo[1,2-a]pyrazin-8-yl)-(2-methylsulfanyl-ethyl)-amine (1.33 g, 4.63 mmol) (from Example 3 supra) was stirred in 1,4-dioxane (30 mL) and Boc$_2$O (1.00 g, 4.63 mmol) followed by DMAP (30 mg, 0.25 mmol) were added and the reaction was heated at 90° C. for 5 hours. After this time, additional Boc$_2$O (1.00 g, 4.63 mmol) was added and the reaction was stirred at 90° C. overnight. The reaction was concentrated to dryness and Et$_2$O (50 mL) added. The organic layer was washed with water (4×25 mL), dried over MgSO$_4$ and concentrated to dryness. The crude product was purified by column chromatography on silica gel (100% petroleum ether to 40% EtOAc in petroleum ether, TLC R$_f$=0.52, 30% EtOAc in petroleum ether) to give (3-bromo-imidazo[1,2-a] pyrazin-8-yl)-(2-methylsulfanyl-ethyl)-carbamic acid tert-butyl ester. (Yield 1.15 g, 64%). $^1$H (400 MHz; CDCl$_3$) δ 1.41 (9 H, s); 2.10 (3 H, s); 2.85-2.89 (2 H, m), 4.07-4.11 (2 H, m), 7.75 (1 H, s), 7.81 (1 H, d, J=5 Hz), 7.95 (1 H, d, J=5 Hz).

Example 5

(3-Bromo-imidazo[1,2-a]pyrazin-8-yl)-(2-methane-sulfonyl-ethyl)-carbamic acid tert-butyl ester

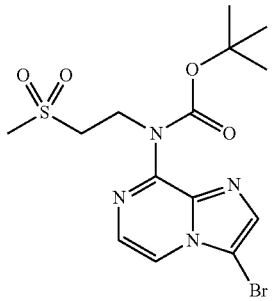 [SMILES: CC(C)(C)OC(=O)N(CCS(C)(=O)=O)c1nccn2c(Br)cnc12]

(3-Bromo-imidazo[1,2-a]pyrazin-8-yl)-(2-methylsulfanyl-ethyl)-carbamic acid tert-butyl ester (1.52 g, 3.93 mmol) (from Example 4 supra) was stirred in DCM (25 mL), cooled in ice and mCPBA (2.20 g, 77% max purity, 9.82 mmol) added portion-wise over 3 minutes. The reaction was stirred for 30 minutes then diluted with DCM (50 mL) and washed with 10% sodium metabisulphite (25 mL), 10% NaHCO$_3$ (3×25 mL), dried over MgSO$_4$ and concentrated to dryness. The residue was purified by column chromatography on silica gel (petroleum ether to EtOAc; TLC R$_f$=0.23, 60% EtOAc in petroleum ether) to give (3-bromo-imidazo[1,2-a]pyrazin-8-yl)-(2-methanesulfonyl-ethyl)-carbamic acid tert-butyl ester. (Yield 1.61 g, 98%).

$^1$H (400 MHz; CDCl$_3$) δ 1.40 (9 H, s), 3.04 (3 H, s), 3.61 (2 H, t, J=7 Hz), 4.31-4.35 (2 H, m), 7.74 (1 H, s), 7.83 (1 H, d, J=5 Hz), 7.99 (1 H, d, J=5 Hz).

Example 6

(3-Bromo-imidazo[1,2-a]pyrazin-8-yl)-methyl-amine

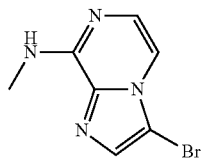

(3-Bromo-imidazo[1,2-a]pyrazin-8-yl)-methyl-amine was prepared by a process analogous to that described in Example 2 starting from 3-bromo-8-chloro-imidazo[1,2-a]pyrazine and excess methylamine (33% weight in EtOH) at room temperature in EtOH.

Example 7

(3-Bromo-imidazo[1,2-a]pyrazin-8-yl)-methyl-carbamic acid tert-butyl ester

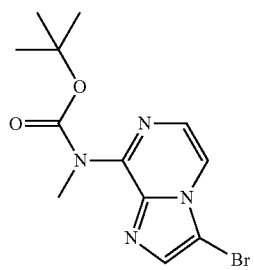 [SMILES: CN(C(=O)OC(C)(C)C)c1nccn2c(Br)cnc12]

(3-Bromo-imidazo[1,2-a]pyrazin-8-yl)-methyl-carbamic acid tert-butyl ester was prepared by a process analogous to that described in Example 4 starting from (3-bromo-imidazo[1,2-a]pyrazin-8-yl)-methyl-amine (from Example 6 supra).

Example 8

Methyl-[3-(2-methylsulfanyl-pyrimidin-4-yl)-imidazo[1,2-a]pyrazin-8-yl]-carbamic acid tert-butyl ester

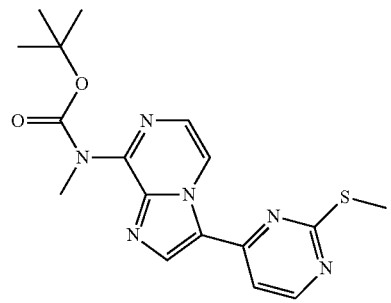 [SMILES: CSc1nccc(-c2cnc3c(N(C)C(=O)OC(C)(C)C)nccn23)n1]

2-Methylsulfanyl-4-tributylstannanyl-pyrimidine (19.1 g, 46.0 mmol) was stirred in degassed toluene (achieved by bubbling nitrogen though solvent for 2 hours) (200 mL) under nitrogen, then (3-bromo-imidazo[1,2-a]pyrazin-8-yl)-methyl-carbamic acid tert-butyl ester (13.1 g, 40.0 mmol) (from Example 7 supra) was added followed by bis(triphenylphosphine)palladium (II) chloride (1.12 g, 1.60 mmol) and the reaction was heated at reflux. The reaction was cooled to room temperature and concentrated to dryness. The residue was purified by column chromatography on silica gel (petroleum ether to EtOAc, TLC R$_f$=0.17, 20% EtOAc in petroleum ether) and then triturated with DIPE to give methyl-[3-(2-methylsulfanyl-pyrimidin-4-yl)-imidazo[1,2-a]pyrazin-8-yl]-carbamic acid tert-butyl ester. (Yield 8.00 g, 54%).

$^1$H (400 MHz; CDCl$_3$) δ 1.42 (9 H, s), 2.67 (3 H, s), 3.48 (3 H, s), 7.36 (1 H, d, J=4 Hz), 7.93 (1 H, d, J=4 Hz), 8.37 (1 H, s), 8.55 (1 H, d, J=4 Hz), 9.64 (1 H, d, J=4 Hz). LC-MS: [M+H]$^+$373.3.

Example 9

(3-Bromo-imidazo[1,2-a]pyrazin-8-yl)-isopropyl-amine

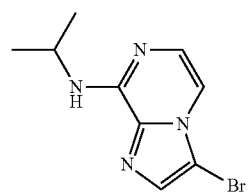

(3-Bromo-imidazo[1,2-a]pyrazin-8-yl)-isopropyl-amine was prepared by a process analogous to that described in Example 2 starting from 3-bromo-8-chloro-imidazo[1,2-a]pyrazine and isopropylamine.

Example 10

(3-Bromo-imidazo[1,2-a]pyrazin-8-yl)-isopropyl-carbamic acid tert-butyl ester

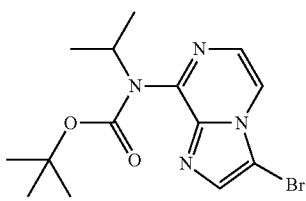 [SMILES: CC(C)N(C(=O)OC(C)(C)C)c1nccn2c(Br)cnc12]

(3-Bromo-imidazo[1,2-a]pyrazin-8-yl)-isopropyl-carbamic acid tert-butyl ester was prepared by a process analogous to that described in Example 4 starting from (3-bromo-imidazo[1,2-a]pyrazin-8-yl)-isopropyl-amine (from Example 9 supra).

Example 11

Isopropyl-[3-(2-methylsulfanyl-pyrimidin-4-yl)-imidazo[1,2-a]pyrazin-8-yl]-carbamic acid tert-butyl ester

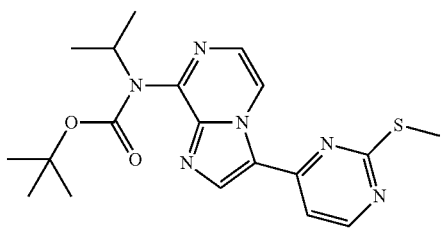 [SMILES: CSc1nccc(-c2cnc3c(N(C(=O)OC(C)(C)C)C(C)C)nccn23)n1]

Isopropyl-[3-(2-methylsulfanyl-pyrimidin-4-yl)-imidazo[1,2-a]pyrazin-8-yl]-carbamic acid tert-butyl ester was prepared by a process analogous to that described in Example 8 starting from (3-bromo-imidazo[1,2-a]pyrazin-8-yl)-isopropyl-carbamic acid tert-butyl ester (from Example 10 supra).

Example 12

Isopropyl-[3-(2-phenylamino-pyrimidin-4-yl)-imidazo[1,2-a]pyrazin-8-yl]-amine 345.41

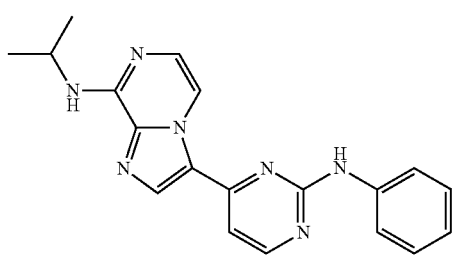

To isopropyl-[3-(2-methanesulfonyl-pyrimidin-4-yl)-imidazo[1,2-a]pyrazin-8-yl]-carbamic acid tert-butyl ester (117 mg, 0.27 mmol) (from Example 11 supra) was added aniline (38 µL, 0.42 mmol) in "BuOH (3 mL) followed by conc.HCl (38 µL, 0.46 mmol) and the reaction was shaken at 95° C. overnight. After this time the reaction was concentrated to dryness, dissolved in DMSO (1.8 mL) and then purified by preparative HPLC to give isopropyl-[3-(2-phenylamino-pyrimidin-4-yl)-imidazo[1,2-a]pyrazin-8-yl]-amine. (Yield 27.3 mg, 29%). LC-MS: [M+H]$^+$ 346.3.

Example 13

2-[3-(2-Phenylamino-pyrimidin-4-yl)-imidazo[1,2-a]pyrazin-8-ylamino]-ethanol 347.149

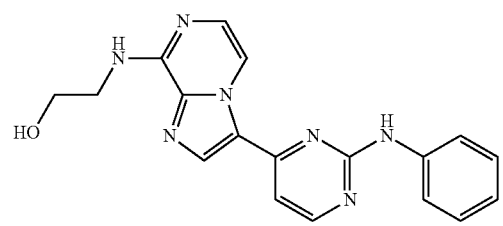

2-[3-(2-Phenylamino-pyrimidin-4-yl)-imidazo[1,2-a]pyrazin-8-ylamino]-ethanol was prepared by a process analogous to that described in Example 12 starting from 2-(3-bromo-imidazo[1,2-a]pyrazin-8-ylamino)-ethanol (from Example 2 supra), 2-methylsulfanyl-4-tributylstannanyl-pyrimidine, and aniline. LC-MS: [M+H]$^+$ 348.3.

Example 14

(2-Methanesulfonyl-ethyl)-{3-[2-(tetrahydro-pyran-4-ylamino)-pyrimidin-4-yl]-imidazo[1,2-a]pyrazin-8-yl}-amine 417.49

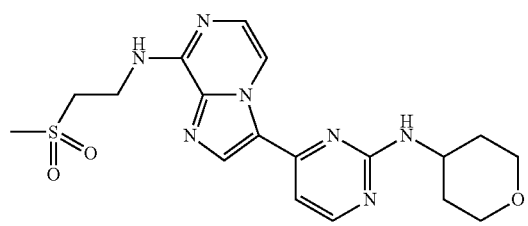

(2-Methanesulfonyl-ethyl)-{3-[2-(tetrahydro-pyran-4-ylamino)-pyrimidin-4-yl]-imidazo[1,2-a]pyrazin-8-yl}-amine was prepared by a process analogous to that described in Example 12 starting from (3-bromo-imidazo[1,2-a]pyrazin-8-yl)-(2-methanesulfonyl-ethyl)-carbamic acid tert-butyl ester (from Example 5 supra), 2-methylsulfanyl-4-tributylstannanyl-pyrimidine, and 4-amino-tetrahydropyran. LC-MS: [M+H]$^+$ 418.2.

Example 15

(2-Methanesulfonyl-ethyl)-[3-(2-morpholin-4-yl-pyrimidin-4-yl)-imidazo[1,2-a]pyrazin-8-yl]-amine

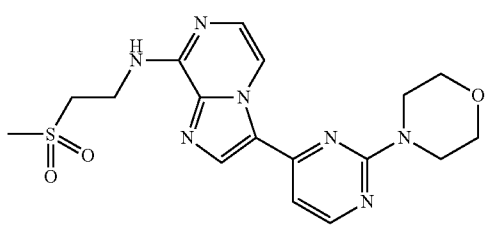

403.143

(2-Methanesulfonyl-ethyl)-[3-(2-morpholin-4-yl-pyrimidin-4-yl)-imidazo[1,2-a]pyrazin-8-yl]-amine was prepared by a process analogous to that described in Example 12 starting from (3-bromo-imidazo[1,2-a]pyrazin-8-yl)-(2-methanesulfonyl-ethyl)-carbamic acid tert-butyl ester (from Example 5 supra), 2-methylsulfanyl-4-tributylstannanyl-pyrimidine, and morpholine. LC-MS: [M+H]$^+$ 404.2.

Example 16

[3-(2-Isopropylamino-pyrimidin-4-yl)-imidazo[1,2-a]pyrazin-8-yl]-(2-methanesulfonyl-ethyl)-amine

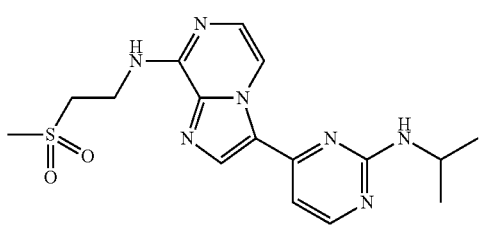

375.45

[3-(2-Isopropylamino-pyrimidin-4-yl)-imidazo[1,2-a]pyrazin-8-yl]-(2-methanesulfonyl-ethyl)-amine was prepared by a process analogous to that described in Example 12 starting from (3-bromo-imidazo[1,2-a]pyrazin-8-yl)-(2-methanesulfonyl-ethyl)-carbamic acid tert-butyl ester (from Example 5 supra), 2-methylsulfanyl-4-tributylstannanyl-pyrimidine, and isopropylamine. LC-MS: [M+H]$^+$ 376.3.

Example 17

4-[4-(8-Isopropylamino-imidazo[1,2-a]pyrazin-3-yl)-pyrimidin-2-ylamino]-cyclohexanol

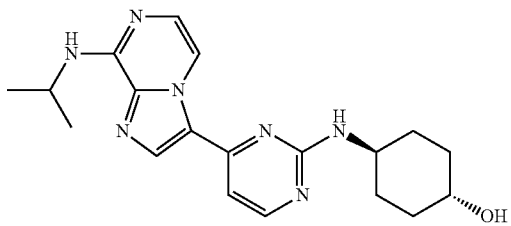

367.45

4-[4-(8-Isopropylamino-imidazo[1,2-a]pyrazin-3-yl)-pyrimidin-2-ylamino]-cyclohexanol was prepared by a process analogous to that described in Example 12 starting from isopropyl-[3-(2-methylsulfanyl-pyrimidin-4-yl)-imidazo[1,2-a]pyrazin-8-yl]-carbamic acid tert-butyl ester (from Example 11 supra), and trans-4-amino-cyclohexanol. LC-MS: [M+H]$^+$ 368.3.

Example 18

Isopropyl-{3-[2-(tetrahydro-pyran-4-ylamino)-pyrimidin-4-yl]-imidazo[1,2-a]pyrazin-8-yl}-amine

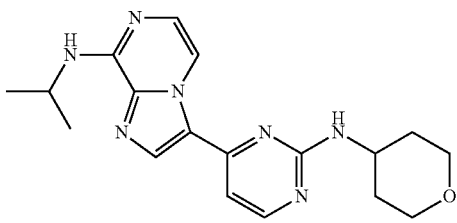

353.43

Isopropyl-{3-[2-(tetrahydro-pyran-4-ylamino)-pyrimidin-4-yl]-imidazo[1,2-a]pyrazin-8-yl}-amine was prepared by a process analogous to that described in Example 12 starting from isopropyl-[3-(2-methylsulfanyl-pyrimidin-4-yl)-imidazo[1,2-a]pyrazin-8-yl]-carbamic acid tert-butyl ester (from Example 11 supra), and 4-amino-tetrahydropyran. LC-MS: [M+H]$^+$ 354.3.

Example 19

Isopropyl-[3-(2-morpholin-4-yl-pyrimidin-4-yl)-imidazo[1,2-a]pyrazin-8-yl]-amine

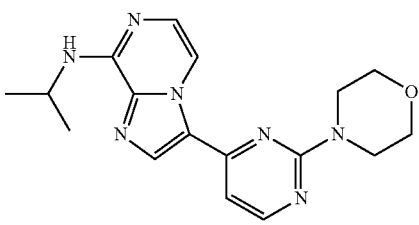

339.4

Isopropyl-[3-(2-morpholin-4-yl-pyrimidin-4-yl)-imidazo[1,2-a]pyrazin-8-yl]-amine was prepared by a process analogous to that described in Example 12 starting from isopropyl-[3-(2-methylsulfanyl-pyrimidin-4-yl)-imidazo[1,2-a]pyrazin-8-yl]-carbamic acid tert-butyl ester (from Example 11 supra), and morpholine. LC-MS: [M+H]$^+$ 340.3.

Example 20

Methyl-[3-(2-phenylamino-pyrimidin-4-yl)-imidazo[1,2-a]pyrazin-8-yl]-amine 317.35

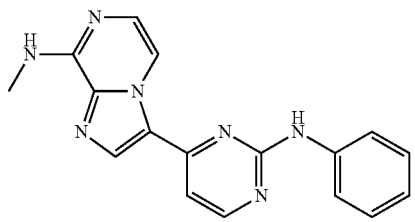

Methyl-[3-(2-phenylamino-pyrimidin-4-yl)-imidazo[1,2-a]pyrazin-8-yl]-amine was prepared by a process analogous to that described in Example 12 starting from methyl-[3-(2-methylsulfanyl-pyrimidin-4-yl)-imidazo[1,2-a]pyrazin-8-yl]-carbamic acid tert-butyl ester (from Example 8 supra), and aniline. LC-MS: [M+H]$^+$ 318.2.

Example 21

Methyl-[3-(2-morpholin-4-yl-pyrimidin-4-yl)-imidazo[1,2-a]pyrazin-8-yl]-amine 311.35

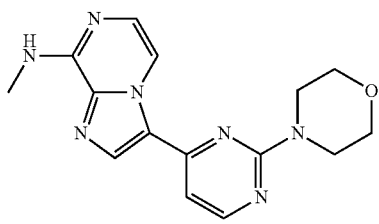

Methyl-[3-(2-morpholin-4-yl-pyrimidin-4-yl)-imidazo[1,2-a]pyrazin-8-yl]-amine was prepared by a process analogous to that described in Example 12 starting from methyl-[3-(2-methylsulfanyl-pyrimidin-4-yl)-imidazo[1,2-a]pyrazin-8-yl]-carbamic acid tert-butyl ester (from Example 8 supra), and morpholine. LC-MS: [M+H]$^+$ 312.3.

Example 22

Piperidin-4-yl-{3-[2-(tetrahydro-pyran-4-ylamino)-pyrimidin-4-yl]-imidazo[1,2-a]pyrazin-8-yl}-amine 394.48

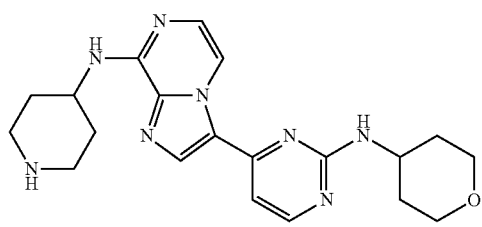

Piperidin-4-yl-{3-[2-(tetrahydro-pyran-4-ylamino)-pyrimidin-4-yl]-imidazo[1,2-a]pyrazin-8-yl}-amine was prepared by a process analogous to that described in Example 12 starting from 3-bromo-8-chloro-imidazo[1,2-a]pyrazine (from Example 1 supra), 4-amino-piperidine-1-carboxylic acid tert-butyl ester, 2-methylsulfanyl-4-tributylstannanyl-pyrimidine, and 4-amino-tetrahydropyran. LC-MS: [M+H]$^+$ 395.4.

Example 23

[3-(2-Morpholin-4-yl-pyrimidin-4-yl)-imidazo[1,2-a]pyrazin-8-yl]-piperidin-4-yl-amine 380.45

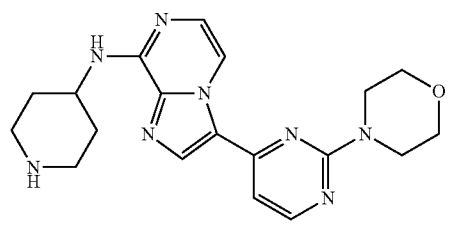

[3-(2-Morpholin-4-yl-pyrimidin-4-yl)-imidazo[1,2-a]pyrazin-8-yl]-piperidin-4-yl-amine was prepared by a process analogous to that described in Example 12 starting from 3-bromo-8-chloro-imidazo[1,2-a]pyrazine (from Example 1 supra), 4-amino-piperidine-1-carboxylic acid tert-butyl ester, 2-methylsulfanyl-4-tributylstannanyl-pyrimidine, and morpholine. LC-MS: [M+H]$^+$ 381.3.

Example 24

[3-(2-Isopropylamino-pyrimidin-4-yl)-imidazo[1,2-a]pyrazin-8-yl]-piperidin-4-yl-amine 352.44

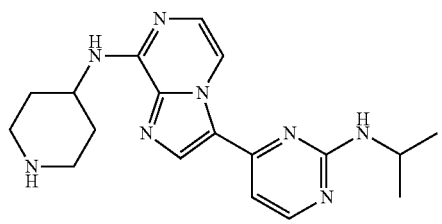

[3-(2-Isopropylamino-pyrimidin-4-yl)-imidazo[1,2-a]pyrazin-8-yl]-piperidin-4-yl-amine was prepared by a process analogous to that described in Example 12 starting from 3-bromo-8-chloro-imidazo[1,2-a]pyrazine (from Example 1 supra), 4-amino-piperidine-1-carboxylic acid tert-butyl ester, 2-methylsulfanyl-4-tributylstannanyl-pyrimidine, and isopropylamine. LC-MS: [M+H]$^+$ 353.3.

Example 25

Isopropyl-[3-(2-isopropylamino-pyrimidin-4-yl)-imidazo[1,2-a]pyrazin-8-yl]-amine 311.39

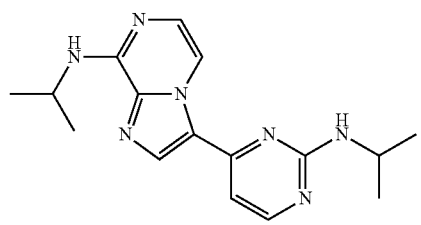

Isopropyl-[3-(2-isopropylamino-pyrimidin-4-yl)-imidazo[1,2-a]pyrazin-8-yl]-amine was prepared by a process analogous to that described in Example 12 starting from isopropyl-[3-(2-methylsulfanyl-pyrimidin-4-yl)-imidazo[1,2-a]

pyrazin-8-yl]-carbamic acid tert-butyl ester (from Example 11 supra), and isopropylamine. LC-MS: [M+H]⁺ 312.3.

Example 26

[3-(2-Methylamino-pyrimidin-4-yl)-imidazo[1,2-a]pyrazin-8-yl]-piperidin-4-yl-amine

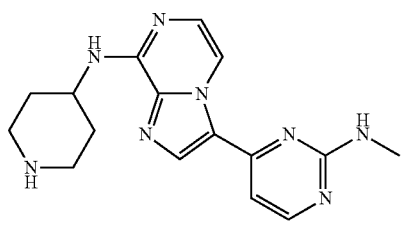

324.39

[3-(2-Methylamino-pyrimidin-4-yl)-imidazo[1,2-a]pyrazin-8-yl]-piperidin-4-yl-amine was prepared by a process analogous to that described in Example 12 starting from 3-bromo-8-chloro-imidazo[1,2-a]pyrazine (from Example 1 supra), 4-amino-piperidine-1-carboxylic acid tert-butyl ester, 2-methylsulfanyl-4-tributylstannanyl-pyrimidine, and methylamine. LC-MS: [M+H]⁺ 325.3.

Example 27

4-{4-[8-(2-Methanesulfonyl-ethylamino)-imidazo[1,2-a]pyrazin-3-yl]-pyrimidin-2-ylamino}-cyclohexanol

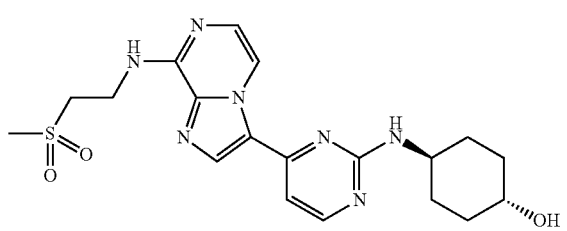

431.52

4-{4-[8-(2-Methanesulfonyl-ethylamino)-imidazo[1,2-a]pyrazin-3-yl]-pyrimidin-2-ylamino}-cyclohexanol was prepared by a process analogous to that described in Example 12 starting from (3-bromo-imidazo[1,2-a]pyrazin-8-yl)-(2-methanesulfonyl-ethyl)-carbamic acid tert-butyl ester (from Example 5 supra), 2-methylsulfanyl-4-tributylstannanyl-pyrimidine, and trans-4-amino-cyclohexanol. LC-MS: [M+H]⁺ 432.1.

Example 28

2-{3-[2-(Tetrahydro-pyran-4-ylamino)-pyrimidin-4-yl]-imidazo[1,2-a]pyrazin-8-ylamino}-ethanol

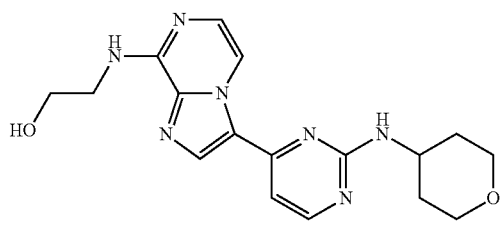

355.4

2-{3-[2-(Tetrahydro-pyran-4-ylamino)-pyrimidin-4-yl]-imidazo[1,2-a]pyrazin-8-ylamino}-ethanol was prepared by a process analogous to that described in Example 12 starting from 2-(3-bromo-imidazo[1,2-a]pyrazin-8-ylamino)-ethanol (from Example 2 supra), 2-methylsulfanyl-4-tributylstannanyl-pyrimidine, and 4-amino-tetrahydropyran. LC-MS: [M+H]⁺ 356.3.

Example 29

2-[3-(2-Morpholin-4-yl-pyrimidin-4-yl)-imidazo[1,2-a]pyrazin-8-ylamino]-ethanol

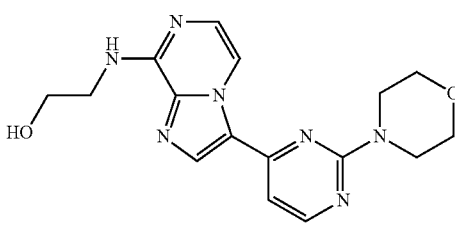

341.37

2-[3-(2-Morpholin-4-yl-pyrimidin-4-yl)-imidazo[1,2-a]pyrazin-8-ylamino]-ethanol was prepared by a process analogous to that described in Example 12 starting from 2-(3-bromo-imidazo[1,2-a]pyrazin-8-ylamino)-ethanol (from Example 2 supra), 2-methylsulfanyl-4-tributylstannanyl-pyrimidine, and morpholine. LC-MS: [M+H]⁺ 342.3.

Example 30

2-[3-(2-Isopropylamino-pyrimidin-4-yl)-imidazo[1,2-a]pyrazin-8-ylamino]-ethanol

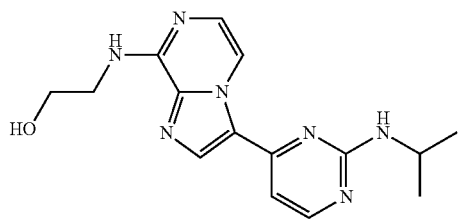

313.36

2-[3-(2-Isopropylamino-pyrimidin-4-yl)-imidazo[1,2-a]pyrazin-8-ylamino]-ethanol was prepared by a process analogous to that described in Example 12 starting from 2-(3-bromo-imidazo[1,2-a]pyrazin-8-ylamino)-ethanol (from Example 2 supra), 2-methylsulfanyl-4-tributylstannanyl-pyrimidine, and isopropylamine. LC-MS: [M+H]⁺ 314.3.

Example 31

2-[3-(2-Methylamino-pyrimidin-4-yl)-imidazo[1,2-a]pyrazin-8-ylamino]-ethanol

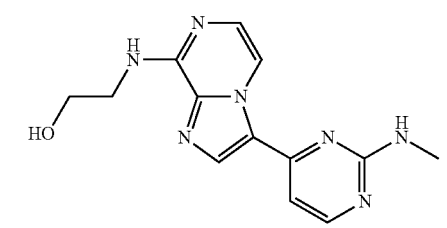

285.31

2-[3-(2-Methylamino-pyrimidin-4-yl)-imidazo[1,2-a]pyrazin-8-ylamino]-ethanol was prepared by a process analogous to that described in Example 12 starting from 2-(3- bromo-imidazo[1,2-a]pyrazin-8-ylamino)-ethanol (from Example 2 supra), 2-methylsulfanyl-4-tributylstannanyl-pyrimidine, and methylamine. LC-MS: [M+H]+ 286.2.

Example 32

Isopropyl-[3-(2-methylamino-pyrimidin-4-yl)-imidazo[1,2-a]pyrazin-8-yl]-amine

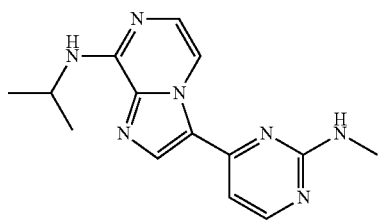

283.34

Isopropyl-[3-(2-methylamino-pyrimidin-4-yl)-imidazo[1,2-a]pyrazin-8-yl]-amine was prepared by a process analogous to that described in Example 12 starting from isopropyl-[3-(2-methylsulfanyl-pyrimidin-4-yl)-imidazo[1,2-a]pyrazin-8-yl]-carbamic acid tert-butyl ester (from Example 11 supra), and methylamine.
LC-MS: [M+H]+ 284.3.

Example 33

(2-Methanesulfonyl-ethyl)-[3-(2-methylamino-pyrimidin-4-yl)-imidazo[1,2-a]pyrazin-8-yl]-amine

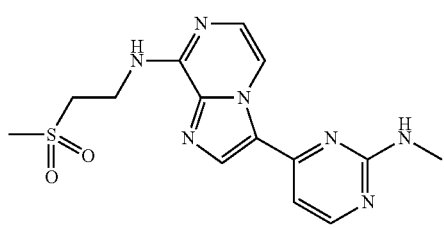

347.116

(2-Methanesulfonyl-ethyl)-[3-(2-methylamino-pyrimidin-4-yl)-imidazo[1,2-a]pyrazin-8-yl]-amine was prepared by a process analogous to that described in Example 12 starting from (3-bromo-imidazo[1,2-a]pyrazin-8-yl)-(2-methanesulfonyl-ethyl)-carbamic acid tert-butyl ester (from Example 5 supra), 2-methylsulfanyl-4-tributylstannanyl-pyrimidine, and methylamine. LC-MS: [M+H]+ 348.2.

Example 34

Methyl-{3-[2-(tetrahydro-pyran-4-ylamino)-pyrimidin-4-yl]-imidazo[1,2-a]pyrazin-8-yl}-amine

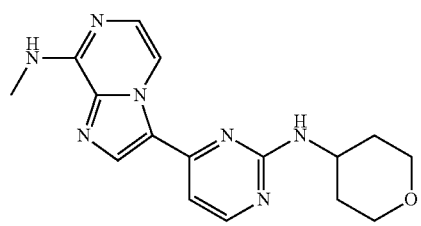

325.165

Methyl-{3-[2-(tetrahydro-pyran-4-ylamino)-pyrimidin-4-yl]-imidazo[1,2-a]pyrazin-8-yl}-amine was prepared by a process analogous to that described in Example 12 starting from methyl-[3-(2-methylsulfanyl-pyrimidin-4-yl)-imidazo[1,2-a]pyrazin-8-yl]-carbamic acid tert-butyl ester (from Example 8 supra), and 4-amino-tetrahydropyran.
LC-MS: [M+H]+ 326.3.

Example 35

Methyl-[3-(2-methylamino-pyrimidin-4-yl)-imidazo[1,2-a]pyrazin-8-yl]-amine

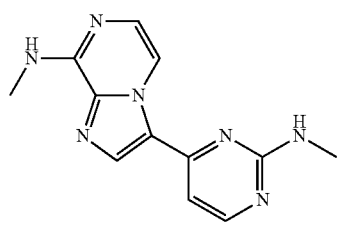

255.28

Methyl-[3-(2-methylamino-pyrimidin-4-yl)-imidazo[1,2-a]pyrazin-8-yl]-amine was prepared by a process analogous to that described in Example 12 starting from methyl-[3-(2-methylsulfanyl-pyrimidin-4-yl)-imidazo[1,2-a]pyrazin-8-yl]-carbamic acid tert-butyl ester (from Example 8 supra), and methylamine LC-MS: [M+H]+ 256.2.

Example 36

2-Bromo-6-(-2-methoxy-vinyl)-pyridine

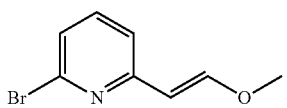

To a suspension of (methoxymethyl)triphenylphosphonium chloride (34.5 g, 100.6 mmol) in THF (500 mL) at −10° C. was added LDA (60 mL, 2 mol/L). The mixture was stirred at −10° C. for 1 hour before addition of 6-bromopicolinaldehyde (10 g, 53.8 mmol) in THF (200 mL). The reaction mixture was then allowed to warm to room temperature and stirred at room temperature for 12 hours. The solution was then partitioned between water and ether. The aqueous fraction was separated and extracted twice with ether. The organic layers were washed with brine and dried over Na$_2$SO$_4$ and filtered. The filtrate was concentrated under reduced pressure to give the crude product which was purified by chromatography (petroleum ether:ethyl acetate, 20:1) to give 2-bromo-6-(-2-methoxy-vinyl)-pyridine. (Yield 9.3 g, 80%). LC-MS: [M+H]+ 215.

Example 37

2-Bromo-6-(1-bromo-2,2-dimethoxy-ethyl)-pyridine

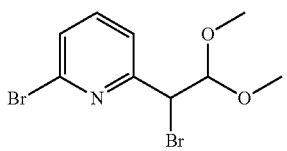

2-Bromo-6-(-2-methoxy-vinyl)-pyridine (from Example 36 supra) (9.3 g, 43.4 mmol) was dissolved in methanol (200 mL), and NBS (9.3 g, 52.3 mmol) was added to the solution at 0° C. After stirring at the same temperature for 30 minutes, water was added to the mixture. The obtained reaction solution was extracted with ethyl acetate. The organic layer was washed with brine, dried and filtered. The filtrate was concentrated under reduced pressure to give a residue which was purified by chromatography (petroleum ether:ethyl acetate, 20:1) to give 2-bromo-6-(1-bromo-2,2-dimethoxy-ethyl)-pyridine. (Yield 11.9 g, 84%). LC-MS: [M+H]$^+$ 324.

Example 38

3-(6-Bromo-pyridin-2-yl)-8-chloro-imidazo[1,2-a]pyrazine

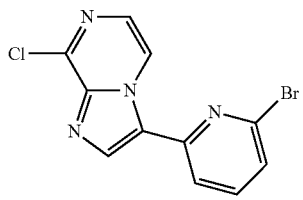 [SMILES: Clc1nccn2c(-c3cccc(Br)n3)cnc12]

A mixture of 2-bromo-6-(1-bromo-2,2-dimethoxy-ethyl)-pyridine (from Example 37 supra) (5.267 g, 16.2 mmol), 3-chloropyrazin-2-amine (2.1 g, 16.2 mmol), and pTsOH.H$_2$O (2.1 g, 11 mmol) in CH$_3$CN (900 mL) and water (90 mL) was stirred and heated at reflux overnight. The reaction mixture was then cooled to room temperature, concentrated under reduced pressure. The crude product was purified by chromatography (CH$_2$Cl$_2$:CH$_3$OH, 100:1) to give 3-(6-bromo-pyridin-2-yl)-8-chloro-imidazo[1,2-a]pyrazine. (Yield 4.86 g, 52%). LC-MS: [M+H]$^+$ 309.

Example 39

3-(6-Bromo-pyridin-2-yl)-8-(4-methyl-piperazin-1-yl)-imidazo[1,2-a]pyrazine

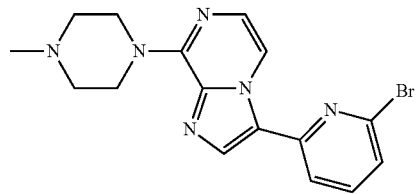 [SMILES: CN1CCN(c2nccn3c(-c4cccc(Br)n4)cnc23)CC1]

A mixture of 3-(6-bromo-pyridin-2-yl)-8-chloro-imidazo[1,2-a]pyrazine (from Example 38 supra) (1.44 g, 4.65 mmol), 1-methylpiperazine (2.1 g, 21 mmol), and diisopropylethylamine (2.7 g, 21 mmol) in 2-propanol (300 mL) was stirred and heated at reflux overnight. The solution was then cooled to room temperature, concentrated under reduced pressure. The resulted solid was washed with water, partitioned between CH$_2$Cl$_2$ and brine. The organic layer was dried over Na$_2$SO$_4$ and filtered. The filtrate was concentrated under reduced pressure. The crude product was purified by chromatography (CH$_2$Cl$_2$:CH$_3$OH, 100:1) to give 3-(6-bromo-pyridin-2-yl)-8-(4-methyl-piperazin-1-yl)-imidazo[1,2-a]pyrazine. (Yield 1.27 g, 73%).

LC-MS: [M+H]$^+$ 373.

Example 40

{4-[3-(6-Bromo-pyridin-2-yl)-imidazo[1,2-a]pyrazin-8-ylamino]-cyclohexyl}-carbamic acid tert-butyl ester

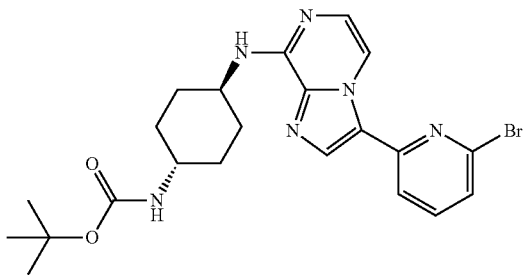

40629-136

A mixture of 3-(6-bromo-pyridin-2-yl)-8-chloro-imidazo[1,2-a]pyrazine (from Example 38 supra) (1.94 g, 6.27 mmol), trans-(4-amino-cyclohexyl)-carbamic acid tert-butyl ester (1.61 g, 7.52 mmol), K$_2$CO$_3$ (1.04 g, 7.52 mmol) in DMF (20 mL) was stirred at 140° C. for 15 hours. The solution was then cooled to room temperature and poured into water.

The resulted solid was filtered and washed with water. The crude product was purified by chromatography (CH$_2$Cl$_2$:CH$_3$OH, 100:1) to give {4-[3-(6-bromo-pyridin-2-yl)-imidazo[1,2-a]pyrazin-8-ylamino]-cyclohexyl}-carbamic acid tert-butyl ester. (Yield 0.512 g, 17%). LC-MS: [M+H]$^+$ 487.

Example 41

[3-(6-Bromo-pyridin-2-yl)-imidazo[1,2-a]pyrazin-8-yl]-(2-morpholin-4-yl-ethyl)-amine

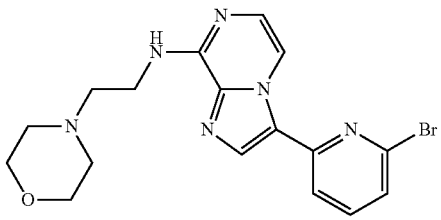 [SMILES: Brc1cccc(-c2cnc3c(NCCN4CCOCC4)nccn23)n1]

A mixture of 3-(6-bromo-pyridin-2-yl)-8-chloro-imidazo[1,2-a]pyrazine (from Example 38 supra) (3.09 g, 10.0 mmol), 2-morpholin-4-yl-ethylamine (2.6 g, 20.0 mmol), NEt$_3$ (2.02 g, 20.0 mmol) in 2-propanol (300 mL) was stirred and heated at reflux for 16 hours. The solution was then cooled to room temperature and poured into water. The resulted solid was filtered and washed with water. The crude product was purified by chromatography (CH$_2$Cl$_2$:CH$_3$OH, 20:1) to give [3-(6-bromo-pyridin-2-yl)-imidazo[1,2-a]pyrazin-8-yl]-(2-morpholin-4-yl-ethyl)-amine. (Yield 2.5 g, 62%). LC-MS: [M+H]$^+$ 403.

Example 42

4-(2-Methoxy-vinyl)-2-methylsulfanyl-pyrimidine

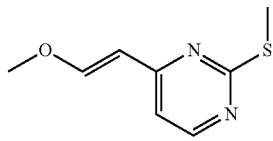

(Methoxymethyl)triphenylphosphonium chloride (68.6 g, 0.2 mol) was dissolved in THF (1000 mL), and lithium diisopropylamide (100 mL, 0.2 mol) was added to the solution at −20° C. After stirring at room temperature for 0.5 hour, the solution of 2-(methylthio)pyrimidine-4-carbaldehyde (15.4 g, 0.1 mol) in THF (400 mL) was added to the solution dropwise. The reaction mixture was stirred at room temperature overnight. Then saturated aqueous ammonium chloride solution (200 mL) was added to the mixture, extracted with ethyl acetate (1500 mL), and dried over with anhydrous sodium sulfate. The organic layer was concentrated and purified by chromatography (petroleum ether:ethyl acetate, 3:1) to give 4-(2-methoxy-vinyl)-2-methylsulfanyl-pyrimidine as a yellow solid. (Yield 11.2 g, 61.2%). LC-MS: [M+H]$^+$ 183.

Example 43

4-(1-Bromo-2,2-dimethoxy-ethyl)-2-methylsulfanyl-pyrimidine

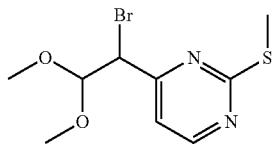

To a stirred solution of 4-(2-methoxy-vinyl)-2-methylsulfanyl-pyrimidine (from Example 42 supra) (11.2 g, 61.2 mmol) in methanol (100 mL) was added N-bromosuccinimide (12 g, 67.3 mmol) at 0° C. After stirring at room temperature for 1 hour, water (100 mL) was added to the mixture, extracted with ethyl acetate (200 mL), and the organic layer dried over with anhydrous sodium sulfate and filtered. Then the filtrate was concentrated and purified by chromatography (petroleum ether:ethyl acetate, 5:1) to give 4-(1-bromo-2,2-dimethoxy-ethyl)-2-methylsulfanyl-pyrimidine as a yellow oil. (Yield 11.5 g, 64.1%). LC-MS: [M+H]$^+$ 293.

Example 44

8-Chloro-3-(2-methylsulfanyl-pyrimidin-4-yl)-imidazo[1,2-a]pyrazine

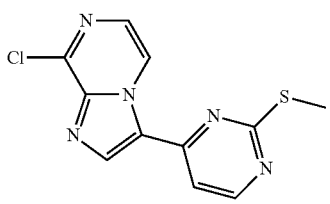 [SMILES: CSc1nccc(-c2cnc3c(Cl)nccn23)n1]

The mixture of 4-(1-bromo-2,2-dimethoxy-ethyl)-2-methylsulfanyl-pyrimidine (from Example 43 supra) (7.5 g, 25.6 mmol), 3-chloropyrazin-2-amine (3.96 g, 30.7 mmol) and p-toluenesulfonic acid (1.594 g, 9.22 mmol) in the mix solvent of acetonitrile/water (120 mL:6 mL) was heated at reflux for 6 hours. The reaction mixture was concentrated and purified by chromatography (dichloromethane:methanol, 20:1) to give 8-chloro-3-(2-methylsulfanyl-pyrimidin-4-yl)-imidazo[1,2-a]pyrazine as a white solid. (Yield 2.3 g, 32.4%). LC-MS: [M+H]$^+$ 278.

Example 45

8-(4-Methyl-piperazin-1-yl)-3-(2-methylsulfanyl-pyrimidin-4-yl)-imidazo[1,2-a]pyrazine

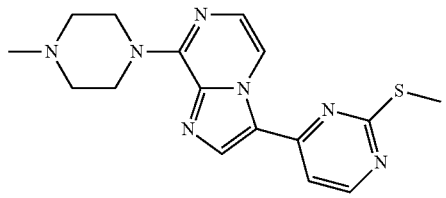

To a solution of 8-chloro-3-(2-methylsulfanyl-pyrimidin-4-yl)-imidazo[1,2-a]pyrazine (from Example 44 supra) (1.36 g, 4.91 mmol) in iPrOH (100 mL) was added 1-methylpiperazine (0.64 g, 6.38 mmol) followed by diisopropylethylamine (0.82 g, 6.38 mmol). The reaction mixture was stirred at reflux for 15 hours and the solvent was removed under reduced pressure. The residue was extracted with dichloromethane (150 mL) and washed with water (3×25 mL), dried over anhydrous sodium sulfate, filtered, and concentrated to afford 8-(4-methyl-piperazin-1-yl)-3-(2-methylsulfanyl-pyrimidin-4-yl)-imidazo[1,2-a]pyrazine. (Yield 1.4 g, 83.7%). LC-MS: [M+H]$^+$ 342.

Example 46

3-(2-Methanesulfonyl-pyrimidin-4-yl)-8-(4-methyl-piperazin-1-yl)-imidazo[1,2-a]pyrazine

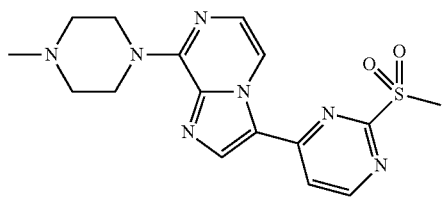

8-(4-Methyl-piperazin-1-yl)-3-(2-methylsulfanyl-pyrimidin-4-yl)-imidazo[1,2-a]pyrazine (from Example 45 supra) (0.9 g, 2.64 mmol) was dissolved in dichloromethane (40 mL), m-CPBA (1.07 g, 5.28 mmol) was added slowly. The reaction mixture was stirred at 0° C. for 2 hours. Solvent was removed under reduced pressure and the solid was purified by column chromatography (silica, 20 g, 200~300 mesh, eluting with dichloromethane:methanol, 1:1) to afford 3-(2-methanesulfonyl-pyrimidin-4-yl)-8-(4-methyl-piperazin-1-yl)-imidazo[1,2-a]pyrazine. (Yield 0.9 g, 91.4%). LC-MS: [M+H]$^+$ 374.

Example 47

{4-[3-(2-Methylsulfanyl-pyrimidin-4-yl)-imidazo[1,2-a]pyrazin-8-ylamino]-cyclohexyl}-carbamic acid tert-butyl ester

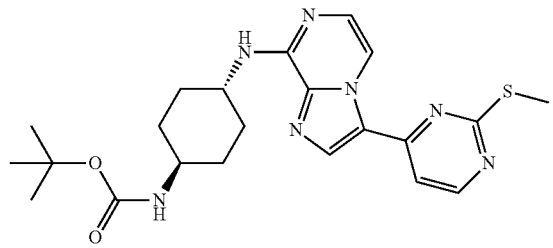 [SMILES: CSc1nccc(-c2cnc3c(N[C@H]4CC[C@H](NC(=O)OC(C)(C)C)CC4)nccn23)n1]

To a solution of 8-chloro-3-(2-methylsulfanyl-pyrimidin-4-yl)-imidazo[1,2-a]pyrazine (from Example 44 supra) (0.9 g, 3.24 mmol) in DMF (25 mL) was added trans-(4-aminocyclohexyl)-carbamic acid tert-butyl ester (1.04 g, 4.86 mmol) followed by diisopropylethylamine (0.63 g, 4.86 mmol). The reaction mixture was stirred at 95° C. for 15 hours and the mixture was poured into water. The precipitate formed was filtered, and. the obtained solid was purified by chromatography (silica gel, 10 g, 200-300 mesh, eluting with dichloromethane:methanol, 50:1) to afford {4-[3-(2-methylsulfanyl-pyrimidin-4-yl)-imidazo[1,2-a]pyrazin-8-ylamino]-cyclohexyl}-carbamic acid tert-butyl ester. (Yield 1.23 g, 83.4%). LC-MS: [M+H]+ 456.

Example 48

{4-[3-(2-Methanesulfinyl-pyrimidin-4-yl)-imidazo[1,2-a]pyrazin-8-ylamino]-cyclohexyl}-carbamic acid tert-butyl ester

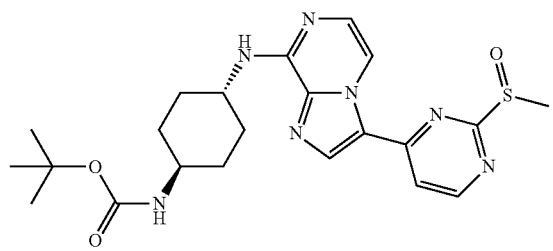 [SMILES: CS(=O)c1nccc(-c2cnc3c(N[C@H]4CC[C@H](NC(=O)OC(C)(C)C)CC4)nccn23)n1]

{4-[3-(2-Methylsulfanyl-pyrimidin-4-yl)-imidazo[1,2-a]pyrazin-8-ylamino]-cyclohexyl}-carbamic acid tert-butyl ester (from Example 47 supra) (150 mg, 0.323 mmol) was dissolved in dichloromethane (20 mL), then m-CPBA (134 mg, 0.659 mmol) was added slowly. The reaction mixture was stirred at 0° C. for 2 hours. The solvent was removed under reduced pressure and the solid was purified by chromatography (silica gel, 10 g, 200-300 mesh, eluting with dichloromethane:methanol, 20:1) to afford {4-[3-(2-methanesulfinyl-pyrimidin-4-yl)-imidazo[1,2-a]pyrazin-8-ylamino]-cyclohexyl}-carbamic acid tert-butyl ester. (Yield 110 mg, 70.8%). LC-MS: [M+H]+ 472.

Example 49

[3-(2-Methylsulfanyl-pyrimidin-4-yl)-imidazo[1,2-a]pyrazin-8-yl]-(2-morpholin-4-yl-ethyl)-amine

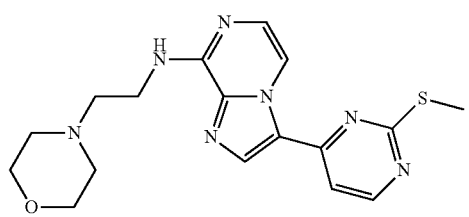 [SMILES: CSc1nccc(-c2cnc3c(NCCN4CCOCC4)nccn23)n1]

To a solution of 8-chloro-3-(2-methylsulfanyl-pyrimidin-4-yl)-imidazo[1,2-a]pyrazine (from Example 44 supra) (400 mg, 1.44 mmol) in iPrOH (20 mL) was added 2-morpholinoethanamine (244 mg, 1.88 mmol) followed by diisopropylethylamine (242 mg, 1.88 mmol). The reaction mixture was stirred at reflux for 15 hours and the solvent was removed under reduced pressure. The residue was extracted with dichloromethane (150 mL) and washed with water (3×25 mL), dried over anhydrous sodium sulfate and concentrated to afford [3-(2-methylsulfanyl-pyrimidin-4-yl)-imidazo[1,2-a]pyrazin-8-yl]-(2-morpholin-4-yl-ethyl)-amine. (Yield 410 g, 76.8%). LC-MS: [M+H]+ 372.

Example 50

[3-(2-Methanesulfonyl-pyrimidin-4-yl)-imidazo[1,2-a]pyrazin-8-yl]-(2-morpholin-4-yl-ethyl)-amine

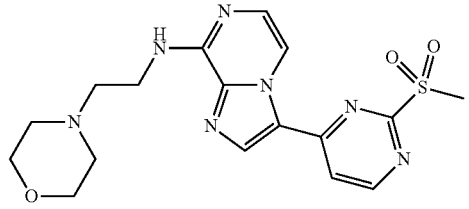 [SMILES: CS(=O)(=O)c1nccc(-c2cnc3c(NCCN4CCOCC4)nccn23)n1]

[3-(2-Methylsulfanyl-pyrimidin-4-yl)-imidazo[1,2-a]pyrazin-8-yl]-(2-morpholin-4-yl-ethyl)-amine (from Example 49 supra) (410 mg, 1.11 mmol) was dissolved in dichloromethane (20 mL). m-CPBA (449 mg, 2.21 mmol) was added slowly. The reaction mixture was stirred at 0° C. for 2 hours. Solvent was then removed under reduced pressure and the solid was purified by column chromatography (silica gel, 10 g, 200-300 mesh, eluting with dichloromethane:methanol, 1:3) to afford [3-(2-methanesulfonyl-pyrimidin-4-yl)-imidazo[1,2-a]pyrazin-8-yl]-(2-morpholin-4-yl-ethyl)-amine. (Yield 300 mg, 67.4%). LC-MS: [M+H]+ 404.

Example 51

(2-Amino-2-phenyl-ethyl)-carbamic acid tert-butyl ester

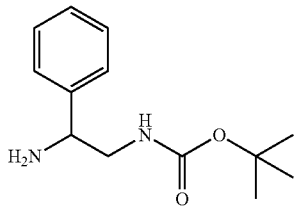

(2-Amino-2-phenyl-ethyl)-carbamic acid tert-butyl ester was prepared according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A (2-Hydroxy-2-phenyl-ethyl)-carbamic acid tert-butyl ester

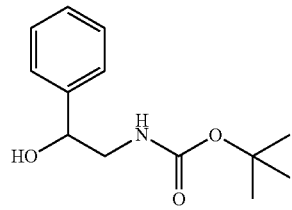 [SMILES: CC(C)(C)OC(=O)NCC(O)c1ccccc1]

To a stirred solution of 2-amino-1-phenylethanol (20 g, 145.8 mmol) in THF (300 mL) was added the solution of $Boc_2O$ (31.1 g, 153.1 mmol) in THF (100 mL) at 0° C. After addition, the mixture was stirred at room temperature for 0.5 hour. This mixture was concentrated to give the pure (2-hydroxy-2-phenyl-ethyl)-carbamic acid tert-butyl ester as a white solid. (Yield 34.4 g, 100%).

Step B

[2-(1,3-Dioxo-1,3-dihydro-isoindol-2-yl)-2-phenyl-ethyl]-carbamic acid tert-butyl ester

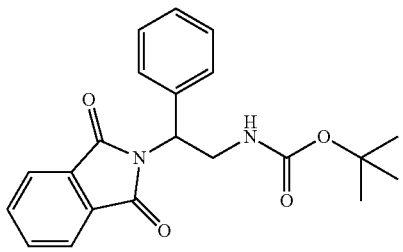 [SMILES: CC(C)(C)OC(=O)NCC(c1ccccc1)N1C(=O)c2ccccc2C1=O]

To a solution of (2-hydroxy-2-phenyl-ethyl)-carbamic acid tert-butyl ester (34.4 g, 145.0 mmol), phthalimide (21.3 g, 145 mmol), and $PPh_3$ (49.4 g, 188.5 mmol) was added dropwise DEAD (32.8 g, 188.5 mmol) under stirring at 0° C. After addition, the mixture was stirred at room temperature for an additional 1 hour. The mixture was concentrated under reduced pressure. The residue was purified by column chromatography on silica gel (petroleum ether:ethyl acetate, 20:1 to 5:1) to give [2-(1,3-dioxo-1,3-dihydro-isoindol-2-yl)-2-phenyl-ethyl]-carbamic acid tert-butyl ester as a white solid. (Yield 39 g, 74%) $^1$H NMR (300 MHz, $CDCl_3$): δ 7.88-7.80 (m, 2H), 7.74-7.68 (m, 2H), 7.49-7.47 (m, 2H), 7.38-7.26 (m, 3H), 5.56-5.50 (m, 1H), 4.83 (brs, 1H), 4.28-4.22 (m, 1H), 3.93-3.87 (m, 1H), 1.35 (s, 9H). LC-MS: $[M-Boc+H]^+$ 267.

Step C (2-Amino-2-phenyl-ethyl)-carbamic acid tert-butyl ester

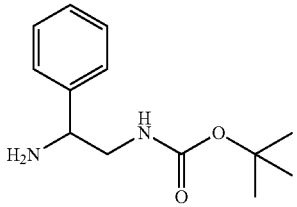 [SMILES: CC(C)(C)OC(=O)NCC(N)c1ccccc1]

To a solution of [2-(1,3-dioxo-1,3-dihydro-isoindol-2-yl)-2-phenyl-ethyl]-carbamic acid tert-butyl ester (23 g, 63 mmol) in THF (180 mL) and MeOH (180 mL) was added 85% hydrazine hydrate (37 mL, 630 mmol) slowly. The resulting mixture was heated to 65° C. for 15 hours. The reaction mixture was cooled to room temperature, then concentrated to dryness. The residue was purified by column chromatography on silica gel (dichloromethane:MeOH, 100:1, 1% $NH_3 \cdot H_2O$) to give (2-amino-2-phenyl-ethyl)-carbamic acid tert-butyl ester as a white solid. (Yield 7.4 g, 50%). $^1$H NMR (300 MHz, $CDCl_3$): δ 7.35-7.24 (m, 5H), 4.81 (brs, 1H), 4.08-4.03 (m, 1H), 3.38-3.21 (m, 2H), 1.44 (s, 9H). LC-MS: $[M+H]^+$ 237.

Example 52

N1-{4-[8-(4-Methyl-piperazin-1-yl)-imidazo[1,2-a]pyrazin-3-yl]-pyrimidin-2-yl}-1-phenyl-ethane-1,2-diamine; hydrochloride

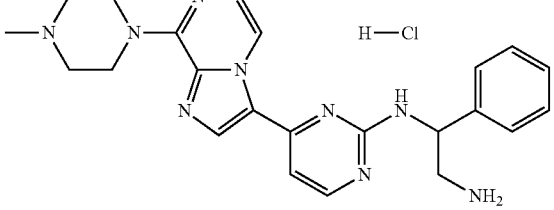

465.99

Step A (2-{4-[8-(4-Methyl-piperazin-1-yl)-imidazo[1,2-a]pyrazin-3-yl]-pyrimidin-2-ylamino}-2-phenyl-ethyl)-carbamic acid tert-butyl ester

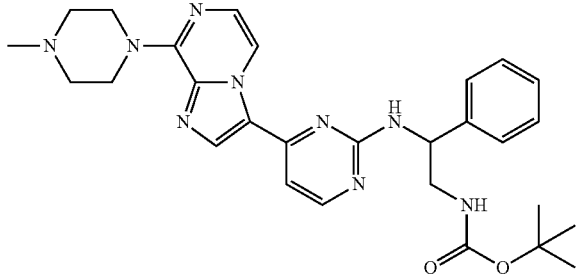 [SMILES: CN1CCN(c2nccn3c(-c4ccnc(NC(CNC(=O)OC(C)(C)C)c5ccccc5)n4)cnc23)CC1]

The mixture of 3-(2-methanesulfonyl-pyrimidin-4-yl)-8-(4-methyl-piperazin-1-yl)-imidazo[1,2-a]pyrazine (from Example 46 supra) (120 mg, 0.32 mmol) and (2-amino-2-phenyl-ethyl)-carbamic acid tert-butyl ester (from Example 51 supra) (305 mg, 1.29 mmol) was heated at 140° C. with stirring for 2 hours. The oil was purified by chromatography (silica gel, 10 g, 200-300 mesh, eluting with dichloromethane:methanol, 50:1 to 20:1) to afford crude (2-{4-[8-(4-methyl-piperazin-1-yl)-imidazo[1,2-a]pyrazin-3-yl]-pyrimidin-2-ylamino}-2-phenyl-ethyl)-carbamic acid tert-butyl ester (Yield 44 mg).

LC-MS: [M+H]+ 530.

Step B

N1-{4-[8-(4-Methyl-piperazin-1-yl)-imidazo[1,2-a]pyrazin-3-yl]-pyrimidin-2-yl}-1-phenyl-ethane-1,2-diamine; hydrochloride

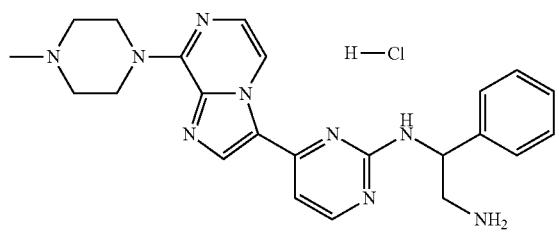 [SMILES: CN1CCN(c2nccn3c(-c4ccnc(NC(CN)c5ccccc5)n4)cnc23)CC1 ; Cl]

To a solution of crude (2-{4-[8-(4-methyl-piperazin-1-yl)-imidazo[1,2-a]pyrazin-3-yl]-pyrimidin-2-ylamino}-2-phenyl-ethyl)-carbamic acid tert-butyl ester (44 mg, 0.083 mmol) in ethanol (3 mL) was added concentrated hydrochloric acid (3 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N1-{4-[4-(4-methyl-piperazin-1-yl)-imidazo[1,2-a]pyrazin-3-yl]-pyrimidin-2-yl}-1-phenyl-ethane-1,2-diamine; hydrochloride (Yield 41 mg, 100%).

1H NMR (300 MHz, D2O): δ 8.49 (s, 1H), 8.31 (s, 1H), 8.15 (d, 1H, J=6.3 Hz), 7.47-7.23 (m, 7H), 5.45 (brs, 1H), 4.96-4.94 (m, 2H), 3.61-3.46 (m, 6H), 3.26-3.22 (m, 2H), 2.86 (s, 3H).

LC-MS: [M+H]+ 430.

Example 53

(3-Amino-3-phenyl-propyl)-carbamic acid tert-butyl ester

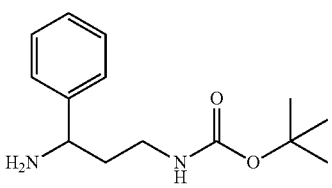 [SMILES: CC(C)(C)OC(=O)NCCC(N)c1ccccc1]

(3-Amino-3-phenyl-propyl)-carbamic acid tert-butyl ester was prepared according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-phenyl-propan-1-ol

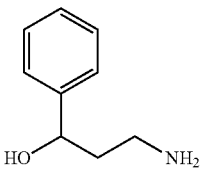

To a stirred suspension of LAH (20 g, 517 mmol) in dry THF (500 mL) was added a solution of 3-oxo-3-phenylpropanenitrile (30 g, 207 mmol) in dry THF (300 mL) drop-wise at 0° C. under nitrogen atmosphere. The mixture was warmed to 25° C. and then heated at 70° C. for 2 hours. After cooling to 0° C., a saturated solution of sodium hydroxide was added drop-wise and extracted with dichloromethane (200 mL). The organic solution was dried over anhydrous sodium sulfate and concentrated to dryness. The residue was purified by column chromatography (methanol:dichloromethane, 1:10) to afford crude 3-amino-1-phenyl-propan-1-ol. (Yield 30 g). LC-MS: [M+H]+ 152.

Step B (3-Hydroxy-3-phenyl-propyl)-carbamic acid tert-butyl ester

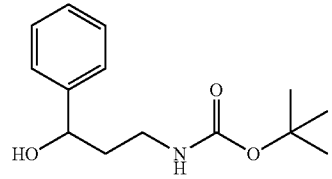 [SMILES: CC(C)(C)OC(=O)NCCC(O)c1ccccc1]

Et3N (1.36 g, 14 mmol) was added to a solution of 3-amino-1-phenyl-propan-1-ol (1.7 g, 11.3 mmol) in THF (20 mL) under stirring. Boc2O (3.0 g, 13.7 mmol) in THF (20 mL) was added dropwise to the solution at 0° C. Then the resulting mixture was warmed to room temperature and stirred for an additional 2 hours. The mixture was concentrated under reduced pressure. The residue was purified by column chromatography on silica gel (petroleum ether:ethyl acetate, 3:1) to give (3-hydroxy-3-phenyl-propyl)-carbamic acid tert-butyl ester. (Yield 1.7 g, 60%). LC-MS: [M+23]+ 274.

Step C

[3-(1,3-Dioxo-1,3-dihydro-isoindol-2-yl)-3-phenyl-propyl]-carbamic acid tert-butyl ester

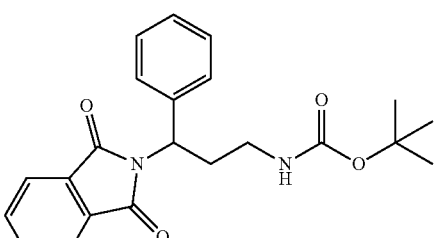

To a solution of (3-hydroxy-3-phenyl-propyl)-carbamic acid tert-butyl ester (10.4 g, 41.4 mmol), phthalimide (5.2 g, 36.6 mmol), and PPh3 (14.6 g, 55.5 mmol) in THF (204 mL) was added dropwise DEAD (8.9 mL, 55 mmol) with stirring at 0° C. Then the resulting mixture was warmed to room temperature for an additional 2 hours. The mixture was concentrated under reduced pressure. The residue was purified by column chromatography on silica gel (petroleum ether:ethyl acetate, 3:1) to give [3-(1,3-dioxo-1,3-dihydro-isoindol-2-yl)-3-phenyl-propyl]-carbamic acid tert-butyl ester. (Yield 10.5 g, 66.8%). ¹H NMR (300 MHz, CDCl₃): δ 7.81-7.75 (m, 2H), 7.69-7.64 (m, 2H), 7.53-7.50 (m, 2H), 7.34-7.23 (m, 3H), 5.44-5.38 (m, 1H), 4.74 (brs, 1H), 3.29-3.07 (m, 2H), 2.83-2.75 (m, 1H), 2.51-2.42 (m, 1H), 1.42 (s, 9H). LC-MS: [M-Boc+H]⁺ 281.

Step D (3-Amino-3-phenyl-propyl)-carbamic acid tert-butyl ester

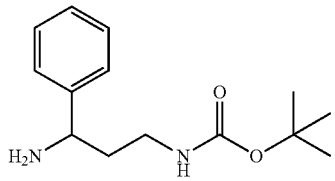

Hydrazine hydrate (85%, 5.1 mL, 74 mmol) was added to a solution of [3-(1,3-dioxo-1,3-dihydro-isoindol-2-yl)-3-phenyl-propyl]-carbamic acid tert-butyl ester (2.8 g, 7.4 mmol) in THF (25 mL) and MeOH (25 mL). The resulting mixture was heated to 65° C. for 6 hours. Then the precipitate was filtered, and the filtrate was concentrated under reduced pressure to give crude product which was purified by column chromatography on silica gel (dichloromethane:MeOH, 100:1, 1% NH₃ H₂O) to give (3-amino-3-phenyl-propyl)-carbamic acid tert-butyl ester as an off-white solid. (Yield 1.7 g, 92%). ¹H NMR (300 MHz, CDCl₃): δ 7.31-7.18 (m, 5H), 6.82 (brs, 1H), 3.78-3.74 (m, 1H), 2.92 (brs, 2H), 1.82 (s, 2H), 1.63-1.61 (m, 2H), 1.37 (s, 9H). LC-MS: [M+H]⁺ 251.

Example 54

N1-{4-[8-(4-Methyl-piperazin-1-yl)-imidazo[1,2-a]pyrazin-3-yl]-pyrimidin-2-yl}-1-phenyl-propane-1,3-diamine; hydrochloride 480.02

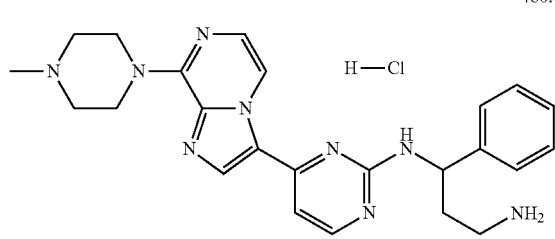

Step A (3-{4-[8-(4-Methyl-piperazin-1-yl)-imidazo[1,2-a]pyrazin-3-yl]-pyrimidin-2-ylamino}-3-phenyl-propyl)-carbamic acid tert-butyl ester

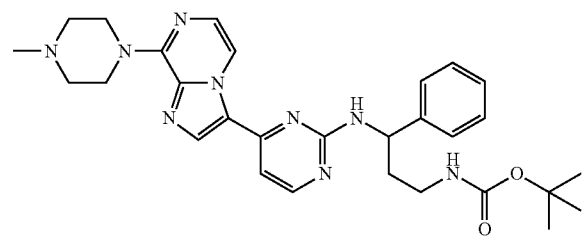 [SMILES: CN1CCN(c2nccn3c(-c4ccnc(NC(CCNC(=O)OC(C)(C)C)c5ccccc5)n4)cnc23)CC1]

The mixture of 3-(2-methanesulfonyl-pyrimidin-4-yl)-8-(4-methyl-piperazin-1-yl)-imidazo[1,2-a]pyrazine (from Example 46 supra) (120 mg, 0.32 mmol) and compound (3-amino-3-phenyl-propyl)-carbamic acid tert-butyl ester (from Example 53 supra) (322 mg, 1.29 mmol) was heated at 140° C. with stirring for 2 hours. The oil was purified by chromatography (silica gel, 10 g, 200-300 mesh, eluting with dichloromethane:methanol, 50:1 to 20:1) to afford crude (3-{4-[8-(4-methyl-piperazin-1-yl)-imidazo[1,2-a]pyrazin-3-yl]-pyrimidin-2-ylamino}-3-phenyl-propyl)-carbamic acid tert-butyl ester. (Yield 51 mg).

LC-MS: [M+H]⁺ 544.

Step B

N1-{4-[8-(4-Methyl-piperazin-1-yl)-imidazo[1,2-a]pyrazin-3-yl]-pyrimidin-2-yl}-1-phenyl-propane-1,3-diamine; hydrochloride

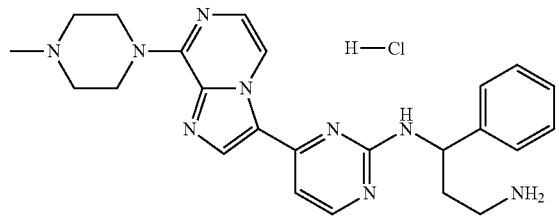 [SMILES: CN1CCN(c2nccn3c(-c4ccnc(NC(CCN)c5ccccc5)n4)cnc23)CC1 ; Cl]

To a solution of crude (3-{4-[8-(4-methyl-piperazin-1-yl)-imidazo[1,2-a]pyrazin-3-yl]-pyrimidin-2-ylamino}-3-phenyl-propyl)-carbamic acid tert-butyl ester (51 mg, 0.094 mmol) in ethanol (3 mL) was added concentrated hydrochloric acid (3 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N1-{4-[8-(4-methyl-piperazin-1-yl)-imidazo[1,2-a]pyrazin-3-yl]-pyrimidin-2-yl}-1-phenyl-propane-1,3-diamine; hydrochloride. (Yield 59 mg, 100%).

¹H NMR (300 MHz, D₂O): δ 8.31 (brs, 1H), 8.29 (s, 1H), 8.09 (brs, 1H), 7.45-7.16 (m, 6H), 5.15 (brs, 1H), 4.99-4.94 (m, 2H), 3.62-3.26 (m, 4H), 3.26-3.02 (m, 4H), 2.87 (s, 3H), 2.28-2.21 (m, 2H). LC-MS: [M+H]⁺ 444.

Example 55

N1-{6-[8-(4-Methyl-piperazin-1-yl)-imidazo[1,2-a]pyrazin-3-yl]-pyridin-2-yl}-1-phenyl-ethane-1,2-diamine; hydrochloride

465

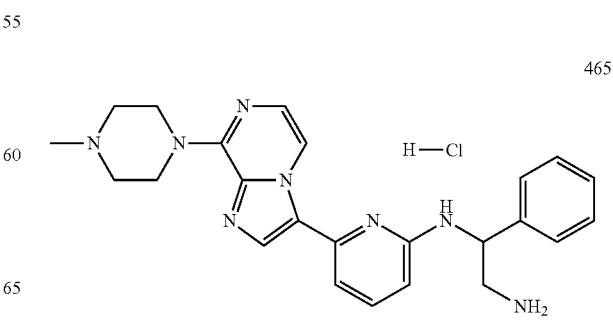

Step A (2-{6-[8-(4-Methyl-piperazin-1-yl)-imidazo[1,2-a]pyrazin-3-yl]-pyridin-2-ylamino}-2-phenyl-ethyl)-carbamic acid tert-butyl ester

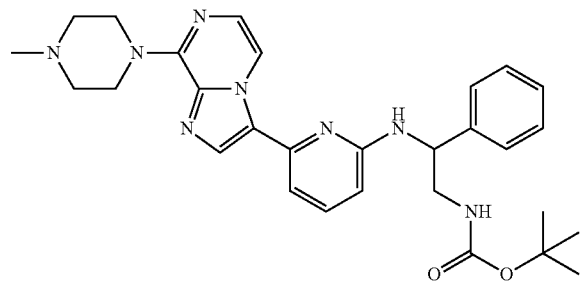

A mixture of 3-(6-bromo-pyridin-2-yl)-8-(4-methyl-piperazin-1-yl)-imidazo[1,2-a]pyrazine (from Example 39 supra) (0.56 g, 1.5 mmol), (2-amino-2-phenyl-ethyl)-carbamic acid tert-butyl ester (from Example 51 supra) (0.425 g, 1.8 mmol), Pd$_2$(dba)$_3$ (90 mg), Davephos (120 mg), K$_2$CO$_3$ (0.25 g, 1.8 mmol) in dioxane (40 mL) in a sealed tube was bubbled with N$_2$ for several minutes and then heated under N$_2$ at 130° C. overnight. The mixture was then cooled to room temperature and filtered. The filtrate was concentrated under reduced pressure. The residue was first purified by chromatography (CH$_2$Cl$_2$:CH$_3$OH, 100:1), then by preparative-HPLC to give (2-{6-[8-(4-methyl-piperazin-1-yl)-imidazo[1,2-a]pyrazin-3-yl]-pyridin-2-ylamino}-2-phenyl-ethyl)-carbamic acid tert-butyl ester. (Yield 30 mg, 3.8%). LC-MS: [M+H]$^+$ 529.

Step B

N1-{6-[8-(4-Methyl-piperazin-1-yl)-imidazo[1,2-a]pyrazin-3-yl]-pyridin-2-yl}-1-phenyl-ethane-1,2-diamine; hydrochloride

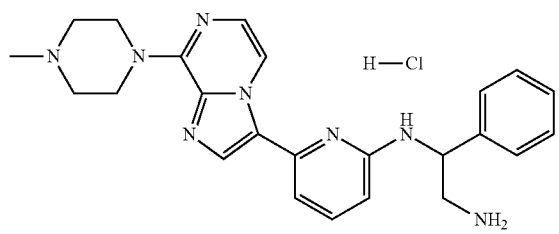 [SMILES: CN1CCN(c2nccn3c(-c4cccc(NC(CN)c5ccccc5)n4)cnc23)CC1 ; Cl]

The mixture of (2-{6-[8-(4-methyl-piperazin-1-yl)-imidazo[1,2-a]pyrazin-3-yl]-pyridin-2-ylamino}-2-phenyl-ethyl)-carbamic acid tert-butyl ester (30 mg, 0.06 mmol) and concentrated HCl (3 mL) in ethanol (3 mL) was stirred at room temperature for 15 hours. The reaction mixture was then concentrated under reduced pressure to give N1-{6-[8-(4-methyl-piperazin-1-yl)-imidazo[1,2-a]pyrazin-3-yl]-pyridin-2-yl}-1-phenyl-ethane-1,2-diamine; hydrochloride. (Yield 40 mg). $^1$HNMR (300 MHz, CD$_3$OD): δ 8.54 (brs, 1H), 8.13 (s, 1H), 7.64-7.46 (m, 3H), 7.31-7.10 (m, 5H), 6.92 (d, 1H, J=8.1 Hz), 5.44 (brs, 3H), 3.93 (brs, 2H), 3.72-3.69 (m, 2H), 3.52-3.34 (m, 4H), 2.92 (s, 3H). LC-MS: [M+H]$^+$ 429.

Example 56

Benzyl-{6-[8-(4-methyl-piperazin-1-yl)-imidazo[1,2-a]pyrazin-3-yl]-pyridin-2-yl}-amine

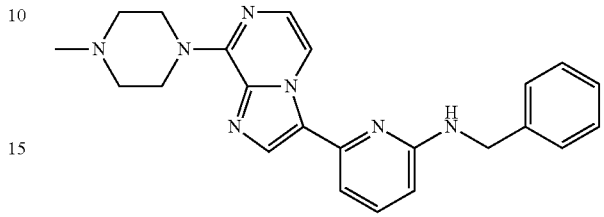

399.5

A mixture of 3-(6-bromo-pyridin-2-yl)-8-(4-methyl-piperazin-1-yl)-imidazo[1,2-a]pyrazine (from Example 39 supra) (0.187 g, 0.5 mmol), benzylamine (0.075 g, 0.7 mmol), Pd$_2$(dba)$_3$ (30 mg), Davephos (40 mg), NaOtBu (70 mg, 0.73 mmol) in dioxane (20 mL) was bubbled with N$_2$ for several minutes and then heated under N$_2$ at reflux overnight. The solution was then cooled to room temperature and filtered. The filtrate was concentrated under reduced pressure. The residue was purified firstly by chromatography (CH$_2$Cl$_2$: CH$_3$OH, 100:1), then by preparative-HPLC to give benzyl-{6-[8-(4-methyl-piperazin-1-yl)-imidazo[1,2-a]pyrazin-3-yl]-pyridin-2-yl}-amine. (Yield 70 mg, 35%). $^1$HNMR (300 MHz, CDCl$_3$): δ 8.70 (d, 1H, J=4.5 Hz), 7.88 (s, 1H), 7.51-7.24 (m, 7H), 7.02 (d, 1H, J=7.2 Hz), 6.37 (d, 1H, J=8.1 Hz), 5.03-5.02 (m, 1H), 4.62 (d, 2H, J=3.9 Hz), 4.24 (brs, 4H), 2.61-2.58 (m, 4H), 2.36 (s, 3H). LC-MS: [M+H]$^+$ 400.

Example 57

Benzyl-{4-[8-(4-methyl-piperazin-1-yl)-imidazo[1,2-a]pyrazin-3-yl]-pyrimidin-2-yl}-amine

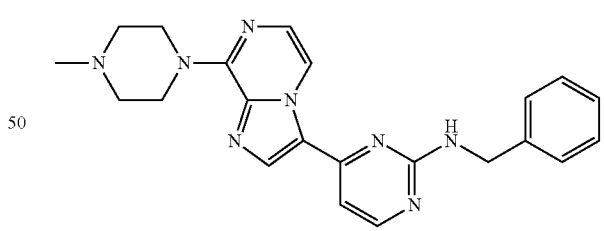

400.49

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and benzylamine (51.7 mg, 0.482 mmol) was heated at 140° C. with stirring for 2 hours. The resulting oil was purified by chromatography (silica gel, 10 g, 200~300 mesh, eluting with dichloromethane:methanol, 30:1 to 10:1) to afford the crude product which was purified by prep-HPLC and concentrated to afford benzyl-{4-[8-(4-methyl-piperazin-1-yl)-imidazo[1,2-a]pyrazin-3-yl]-pyrimidin-2-yl}-amine (Yield 25 mg, 15.5%). $^1$H NMR (300 MHz, CDCl$_3$): δ 8.71 (brs, 1H), 8.31 (d, 1H, J=4.8 Hz), 8.04 (s, 1H), 7.42-7.28 (m, 5H), 6.94 (d, 1H, J=5.4 Hz), 5.68 (brs, 1H), 4.71 (d, 2H, J=5.7 Hz), 4.24 (brs, 4H), 2.60-2.57 (m, 4 H), 2.36 (s, 3H). LC-MS: [M+H]+ 401.

Example 58

(2-Chloro-benzyl)-{4-[8-(4-methyl-piperazin-1-yl)-imidazo[1,2-a]pyrazin-3-yl]-pyrimidin-2-yl}-amine; hydrochloride

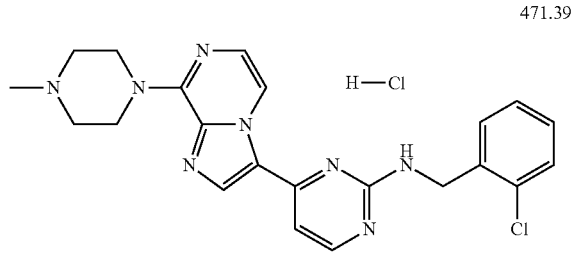 [SMILES: CN1CCN(c2nccn3c(-c4ccnc(NCc5ccccc5Cl)n4)cnc23)CC1 ; Cl]

471.39

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and 2-chlorobenzylamine (228 mg, 1.608 mmol) was heated at 140° C. with stirring for 2 hours. The oil was purified by chromatography (silica gel, 10 g, 200~300 mesh, eluting with dichloromethane:methanol, 30:1~10:1) to afford the crude product (90 mg). The crude product was purified by prep-HPLC. Several drops of concentrated HCl were added to the fractions with product. After sonicating for several minutes, solution was concentrated under reduced pressure to afford (2-chloro-benzyl)-{4-[8-(4-methyl-piperazin-1-yl)-imidazo[1,2-a]pyrazin-3-yl]-pyrimidin-2-yl}-amine; hydrochloride. (Yield 25 mg, 14.3%). 1H NMR (300 MHz, CD3OD): δ 8.62 (s, 1H), 8.58 (s, 1H), 8.25 (s, 1H), 7.52-7.38 (m, 4H), 7.23 (brs, 2H), 5.49-5.45 (m, 2H), 4.87 (brs, 2H), 3.56 (brs, 4H), 3.24 (brs, 2H), 2.87 (s, 3H). LC-MS: [M+H]+ 435.

Example 59

(4-Chloro-benzyl)-{4-[8-(4-methyl-piperazin-1-yl)-imidazo[1,2-a]pyrazin-3-yl]-pyrimidin-2-yl}-amine; hydrochloride

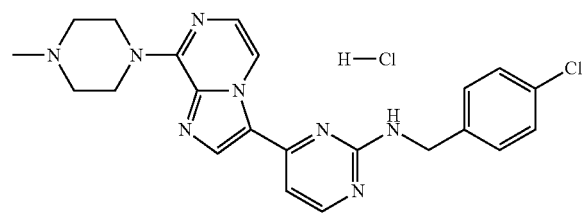

471.39

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and 4-chlorobenzylamine (228 mg, 1.608 mmol) was heated at 140° C. with stirring for 2 hours. The oil was purified by chromatography (silica gel, 10 g, 200~300 mesh, eluting with dichloromethane:methanol, 30:1~10:1) to afford the crude product (100 mg). The crude product was purified by prep-HPLC. Several drops of concentrated HCl were added to the fractions with product. After sonicating for several minutes, solution was concentrated under reduced pressure to afford (4-chloro-benzyl)-{4-[8-(4-methyl-piperazin-1-yl)-imidazo[1,2-a]pyrazin-3-yl]-pyrimidin-2-yl}-amine; hydrochloride. (Yield 38 mg, 21.8%). 1H NMR (300 MHz, CDCl3): δ 8.68 (s, 1H), 8.28 (s, 1H), 7.53 (d, 1H, J=6.9 Hz), 7.38-7.29 (m, 6H), 5.48-5.43 (m, 2H), 4.76 (brs, 2H), 3.68-3.61 (m, 4H), 3.34-3.27 (m, 4H), 2.89 (s, 3H). LC-MS: [M+H]+ 435.

Example 60

N1-{6-[8-(4-Methyl-piperazin-1-yl)-imidazo[1,2-a]pyrazin-3-yl]-pyridin-2-yl}-1-phenyl-propane-1,3-diamine; hydrochloride

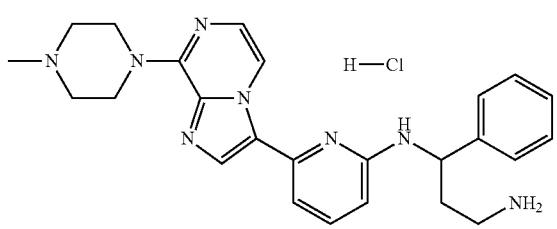

479.03

Step A (3-{6-[8-(4-Methyl-piperazin-1-yl)-imidazo[1,2-a]pyrazin-3-yl]-pyridin-2-ylamino}-3-phenyl-propyl)-carbamic acid tert-butyl ester

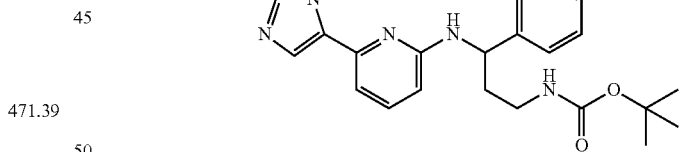

A mixture of 3-(6-bromo-pyridin-2-yl)-8-(4-methyl-piperazin-1-yl)-imidazo[1,2-a]pyrazine (from Example 39 supra) (0.56 g, 1.5 mmol), (3-amino-3-phenyl-propyl)-carbamic acid tert-butyl ester (from Example 53 supra) (0.45 g, 1.8 mmol), Pd2(dba)3 (90 mg), Davephos (120 mg), K2CO3 (0.25 g, 1.8 mmol) in dioxane (60 mL) in a sealed tube was bubbled with N2 for several minutes and then heated under N2 at 130° C. for 15 hours. The solution was then cooled to room temperature and filtered. The filtrate was concentrated under reduced pressure. The residue was purified first by chromatography (CH2Cl2:CH3OH, 100:1) then by preparative-HPLC to give (3-{6-[8-(4-methyl-piperazin-1-yl)-imidazo[1,2-a]pyrazin-3-yl]-pyridin-2-ylamino}-3-phenyl-propyl)-carbamic acid tert-butyl ester. (Yield 44 mg, 5.4%). LC-MS: [M+H]+ 543.

Step B

N1-{6-[8-(4-Methyl-piperazin-1-yl)-imidazo[1,2-a]pyrazin-3-yl]-pyridin-2-yl}-1-phenyl-propane-1,3-diamine; hydrochloride

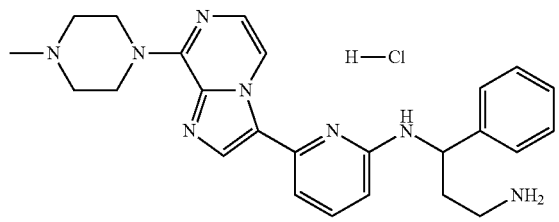 [SMILES: CN1CCN(c2nccn3c(-c4cccc(NC(CCN)c5ccccc5)n4)cnc23)CC1 ; Cl]

The solution of (3-{6-[8-(4-methyl-piperazin-1-yl)-imidazo[1,2-a]pyrazin-3-yl]-pyridin-2-ylamino}-3-phenyl-propyl)-carbamic acid tert-butyl ester (44 mg, 0.08 mmol) in ethanol (4 mL) and concentrated HCl (4 mL) was stirred at room temperature for 15 hours. The reaction mixture was then concentrated under reduced pressure. The residue was suspended in CH$_2$Cl$_2$ and concentrated under reduced pressure to give N1-{6-[8-(4-methyl-piperazin-1-yl)-imidazo[1,2-a]pyrazin-3-yl]-pyridin-2-yl}-1-phenyl-propane-1,3-diamine; hydrochloride. (Yield 25 mg). $^1$H NMR (300 MHz, CD$_3$OD): δ 8.39 (s, 1H), 8.15 (s, 1H), 7.61 (t, 1H, J=5.7 Hz), 7.40-7.48 (m, 7H), 6.78 (brs, 1H), 5.39 (brs, 1H), 5.01 (brs, 1H), 3.81-3.66 (m, 4H), 3.37 (brs, 2H), 3.12-2.91 (m, 7H), 2.16-2.14 (m, 2H). LC-MS: [M+H]$^+$ 443.

Example 61

{4-[8-(4-Methyl-piperazin-1-yl)-imidazo[1,2-a]pyrazin-3-yl]-pyrimidin-2-yl}-thiophen-3-ylmethyl-amine 406.52

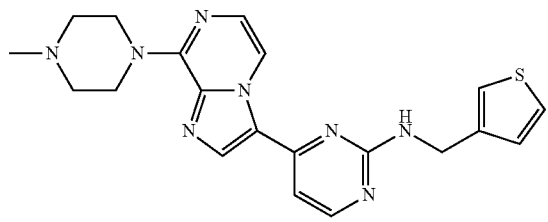

The mixture of 3-(2-methanesulfonyl-pyrimidin-4-yl)-8-(4-methyl-piperazin-1-yl)-imidazo[1,2-a]pyrazine (from Example 46 supra) (120 mg, 0.32 mmol) and thiophen-3-ylmethanamine (145 mg, 1.28 mmol) was heated at 140° C. with stirring for 2 hours. The oil was purified by chromatography (silica gel, 10 g, 200-300 mesh, eluting with dichloromethane:methanol, 30:1 to 10:1) to afford {4-[8-(4-methyl-piperazin-1-yl)-imidazo[1,2-a]pyrazin-3-yl]-pyrimidin-2-yl}-thiophen-3-ylmethyl-amine (Yield 69 mg, 52.8%). $^1$H NMR (300 MHz, DMSO-d$_6$): δ 8.41 (s, 1H), 8.35 (d, 1H, J=5.4 Hz), 7.94 (t, 1H, J=5.7 Hz), 7.51-7.34 (m, 3H), 7.20-7.12 (m, 2H), 4.56 (d, 2H, J=5.7 Hz), 4.17 (brs, 4H), 2.52-2.44 (m, 4H), 2.23 (s, 3H). LC-MS: [M+H]$^+$ 407.

Example 62

[3-Amino-3-(3-chloro-phenyl)-propyl]-carbamic acid tert-butyl ester

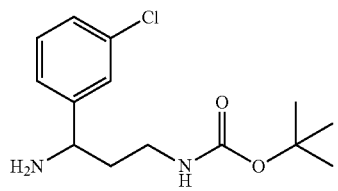 [SMILES: CC(C)(C)OC(=O)NCCC(N)c1cccc(Cl)c1]

[3-Amino-3-(3-chloro-phenyl)-propyl]-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-(3-chloro-phenyl)-propan-1-ol

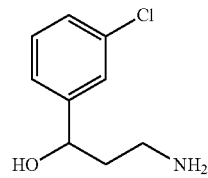

To a stirred suspension of LAH (16 g, 90 mmol) in dry THF (200 mL) was added a solution of 3-(3-chlorophenyl)-3-oxo-propanenitrile (10.4 g, 270 mmol) in dry THF (200 mL) dropwise at 0° C. under nitrogen atmosphere. The mixture was warmed to 25° C. and then heated at 60° C. for 3 hours. After cooling to 0° C., a saturated solution of sodium hydroxide was added dropwise and extracted with ethyl acetate (200 mL). The solution was dried over anhydrous sodium sulfate and concentrated to dryness. The crude 3-amino-1-(3-chlorophenyl)-propan-1-ol obtained was used in the next step without further purification. (Yield 14.5 g). LC-MS: [M+H]$^+$ 186.

Step B

[3-(3-Chloro-phenyl)-3-hydroxy-propyl]-carbamic acid tert-butyl ester

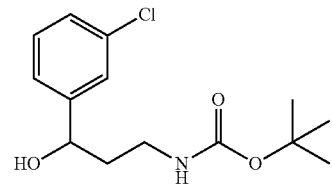 [SMILES: CC(C)(C)OC(=O)NCCC(O)c1cccc(Cl)c1]

To a stirred solution of crude 3-amino-1-(3-chloro-phenyl)-propan-1-ol (29 g, 156 mmol) in THF (300 mL) was added Boc$_2$O (40.5 g, 187 mmol). After 0.5 hour, the mixture was concentrated to dryness. The residue was purified by column chromatography (ethyl acetate:petroleum ether, 1:20) to afford [3-(3-chloro-phenyl)-3-hydroxy-propyl]-carbamic acid tert-butyl ester. (Yield 23 g, 52%). LC-MS: [M+Na]$^+$ 308.

Step C

[3-(3-Chloro-phenyl)-3-(1,3-di oxo-1,3-dihydro-isoindol-2-yl)-propyl]-carbamic acid tert-butyl ester

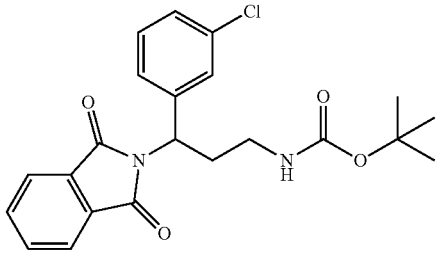 [SMILES: CC(C)(C)OC(=O)NCCC(c1cccc(Cl)c1)N1C(=O)c2ccccc2C1=O]

To a stirred solution of [3-(3-chloro-phenyl)-3-hydroxy-propyl]carbamic acid tert-butyl ester (12 g, 42 mmol), phthalimide (6.2 g, 42 mmol), and PPh₃ (14.3 g, 55 mmol) in THF (150 mL) was added DEAD (9.0 mL, 55 mmol) dropwise at about 5° C. After 1 hour, the mixture was concentrated to dryness. The residue was purified by column chromatography (ethyl acetate:petroleum ether, 1:8) to afford [3-(3-chloro-phenyl)-3-(1,3-dioxo-1,3-dihydro-isoindol-2-yl)-propyl]-carbamic acid tert-butyl ester. (Yield 15.65 g, 90%). LC-MS: [M+H]⁺ 415.

Step D

[3-Amino-3-(3-chloro-phenyl)-propyl]-carbamic acid tert-butyl ester

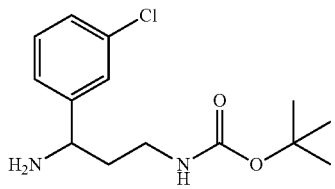 [SMILES: CC(C)(C)OC(=O)NCCC(N)c1cccc(Cl)c1]

To a stirred solution of [3-(3-chloro-phenyl)-3-(1,3-dioxo-1,3-dihydro-isoindol-2-yl)-propyl]-carbamic acid tert-butyl ester (0.15 g, 0.36 mmol) in THF (2 mL) and methanol (2 mL) was added hydrazine hydrate (0.18 g, 3.6 mmol). The mixture was heated to 55° C. for 2 hours. Then the reaction mixture was concentrated and extracted with ethyl acetate (10 mL). The organic mixture was washed with water (3×1 mL), brine (1 mL), dried over anhydrous sodium sulfate and concentrated to dryness. The residue was purified by column chromatography (methanol:dichloromethane, 1:100) to afford [3-amino-3-(3-chloro-phenyl)-propyl]-carbamic acid tert-butyl ester. (Yield 0.061 g, 60%). LC-MS: [M+H]⁺ 285.

Example 63

1-(3-Chloro-phenyl)-N-1-{4-[8-(4-methyl-piperazin-1-yl)-imidazo[1,2-a]pyrazin-3-yl]-pyrimidin-2-yl}-propane-1,3-diamine; hydrochloride 514.46

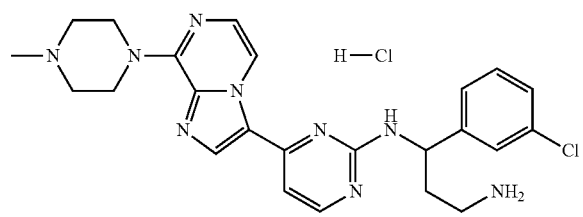 [SMILES: CN1CCN(c2nccn3c(-c4ccnc(NC(CCN)c5cccc(Cl)c5)n4)cnc23)CC1 ; Cl]

Step A (3-(3-Chloro-phenyl)-3-{4-[8-(4-methyl-piperazin-1-yl)-imidazo[1,2-a]pyrazin-3-yl]-pyrimidin-2-ylamino}-propyl)-carbamic acid tert-butyl ester

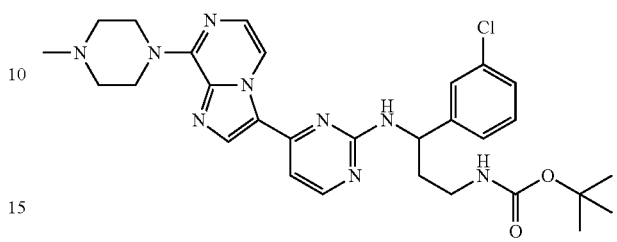

The mixture of 3-(2-methanesulfonyl-pyrimidin-4-yl)-8-(4-methyl-piperazin-1-yl)-imidazo[1,2-a]pyrazine (from Example 46 supra) (100 mg, 0.27 mmol) and [3-amino-3-(3-chloro-phenyl)-propyl]-carbamic acid tert-butyl ester (from Example 62 supra) (307 mg, 1.08 mmol) was heated at 140° C. with stirring for 2 hours. The oil was purified by chromatography (silica gel, 10 g, 200-300 mesh, eluting with dichloromethane:methanol, 50:1 to 20:1) to afford crude (3-(3-chloro-phenyl)-3-{4-[8-(4-methyl-piperazin-1-yl)-imidazo[1,2-a]pyrazin-3-yl]-pyrimidin-2-ylamino}-propyl)-carbamic acid tert-butyl ester. (Yield 123 mg). LC-MS: [M+H]⁺ 578.

Step B 1-(3-Chloro-phenyl)-N-1-{4-[8-(4-methyl-piperazin-1-yl)-imidazo[1,2-a]pyrazin-3-yl]-pyrimidin-2-yl}-propane-1,3-diamine; hydrochloride

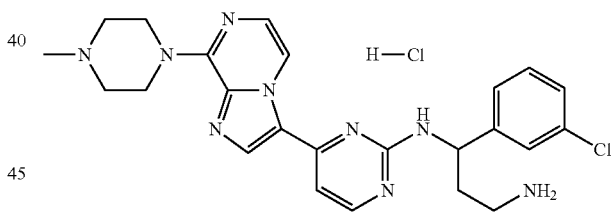

To a solution of crude (3-(3-chloro-phenyl)-3-{4-[8-(4-methyl-piperazin-1-yl)-imidazo[1,2-a]pyrazin-3-yl]-pyrimidin-2-ylamino}-propyl)-carbamic acid tert-butyl ester (120 mg, 0.21 mmol) in ethanol (3 mL) was added concentrated hydrochloric acid (3 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford 1-(3-chloro-phenyl)-N-1-{4-[8-(4-methyl-piperazin-1-yl)-imidazo[1,2-a]pyrazin-3-yl]-pyrimidin-2-yl}-propane-1,3-diamine; hydrochloride. (Yield 70 mg, 48.3%). ¹H NMR (300 MHz, D₂O): δ 8.28 (brs, 1H), 8.21 (s, 1H), 8.05 (brs, 1H), 7.44 (s, 1H), 7.36-7.12 (m, 5H), 5.08-4.88 (m, 3H), 3.56-3.38 (m, 4H), 3.20-2.95 (m, 4H), 2.91 (s, 3H), 2.25-2.10 (m, 2H). LC-MS: [M+H]⁺ 478.

Example 64

{4-[8-(4-Methyl-piperazin-1-yl)-imidazo[1,2-a]pyrazin-3-yl]-pyrimidin-2-yl}-thiophen-2-ylmethyl-amine; hydrochloride 441.989

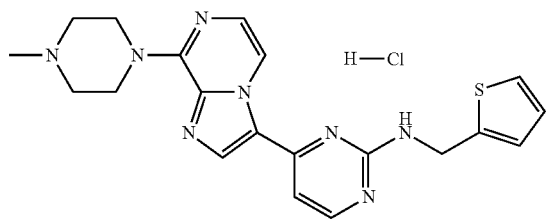

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and thiophen-2-ylmethanamine (182 mg, 1.608 mmol) was heated at 140° C. with stirring for 2 hours. The oil was purified by chromatography (silica gel, 10 g, 200-300 mesh, eluting with dichloromethane:methanol, 30:1 to 10:1) to afford the crude product (115 mg). The crude product was purified by prep-HPLC. Several drops of concentrated HCl were added to the fractions with product. After sonicating for several minutes, solution was concentrated under reduced pressure to afford {4-[8-(4-methyl-piperazin-1-yl)-imidazo [1,2-a]pyrazin-3-yl]-pyrimidin-2-yl}-thiophen-2-ylmethyl-amine; hydrochloride. (Yield 34 mg, 21.2%). $^1$H NMR (300 MHz, CD$_3$OD): δ 9.02 (brs, 1H), 8.84 (s, 1H), 8.39 (d, 1H, J=6.3 Hz), 7.69-7.63 (m, 2H), 7.40 (brs, 1H), 7.23 (s, 1H), 7.06-7.03 (m, 1H), 5.62-5.51 (m, 2H), 5.06-4.99 (m, 2H), 3.88-3.75 (m, 4H), 3.48-3.37 (m, 2H), 3.00 (s, 3H). LC-MS: [M+H]$^+$ 407.

Example 65

(2-Chloro-benzyl)-{6-[8-(4-methyl-piperazin-1-yl)-imidazo[1,2-a]pyrazin-3-yl]-pyridin-2-yl}-amine; hydrochloride 470.405

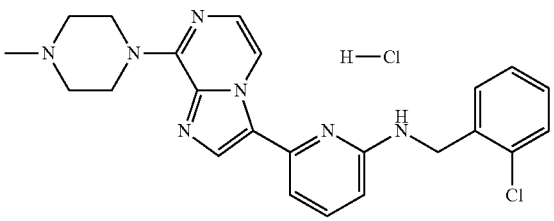

A mixture of 3-(6-bromo-pyridin-2-yl)-8-(4-methyl-piperazin-1-yl)-imidazo[1,2-a]pyrazine (from Example 39 supra) (0.187 g, 0.5 mmol), 2-chloro-benzylamine (71 mg, 0.5 mmol), Pd$_2$(dba)$_3$ (30 mg), Davephos (40 mg), NaOtBu (70 mg, 0.73 mmol) and dioxane (20 mL) in a sealed tube was bubbled with N$_2$ for several minutes and then heated under N$_2$ at 100° C. for 15 hours. The solution was then cooled to room temperature and filtered. The filtrate was concentrated under reduced pressure. The obtained crude product was purified by preparative-HPLC. The obtained product was dissolved in ethanol and then concentrated HCl (1 mL) was added and stirred for 1 h. The mixture was concentrated under reduced pressure. The resulting solid was suspended in dichloromethane and concentrated to give (2-chloro-benzyl)-{6-[8-(4-methyl-piperazin-1-yl)-imidazo[1,2-a]pyrazin-3-yl]-pyridin-2-yl]-amine; hydrochloride. (Yield 47 mg). $^1$HNMR (300 MHz, CD$_3$OD): δ 8.39 (d, 1H, J=5.4 Hz), 8.17 (s, 1H), 7.73 (t, 1H, J=7.8 Hz), 7.40-7.36 (m, 2H), 7.22-7.09 (m, 4H), 6.87 (d, 1H, J=8.4 Hz), 5.43 (brs, 2H), 4.64 (s, 2H), 3.86-3.66 (m, 4H), 3.41-3.37 (m, 2H), 2.91 (s, 3H). LC-MS: [M+H]$^+$ 435.

Example 66

(3-Chloro-benzyl)-{4-[8-(4-methyl-piperazin-1-yl)-imidazo[1,2-a]pyrazin-3-yl]-pyrimidin-2-yl}-amine; hydrochloride 470.405

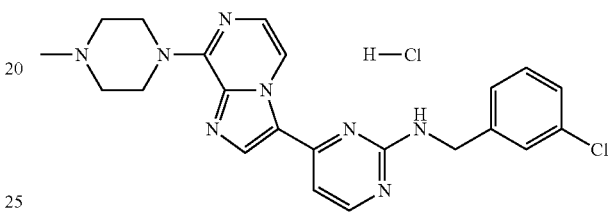

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and 3-chlorobenzylamine (228 mg, 1.608 mmol) was heated at 140° C. with stirring for 2 hours. The resulting oil was purified by chromatography (silica gel, 10 g, 200-300 mesh, eluting with dichloromethane:methanol, 30:1 to 10:1) to afford the crude product (120 mg). Then the crude product was purified by prep-HPLC. Several drops concentrated HCl were added to the fractions with product. After sonicating for several minutes, solution was concentrated under reduced pressure to afford (3-chloro-benzyl)-{4-[8-(4-methyl-piperazin-1-yl)-imidazo [1,2-a]pyrazin-3-yl]-pyrimidin-2-yl}-amine; hydrochloride. (Yield 45 mg, 25.8%).

$^1$H NMR (300 MHz, CD$_3$OD): δ 8.77 (s, 2H), 8.36 (brs, 1H), 7.64-7.36 (m, 6H), 5.59-5.55 (m, 3H), 4.98-4.96 (m, 1H), 3.69-3.63 (m, 4H), 3.41 (brs, 2H), 3.00 (s, 3H). LC-MS: [M+H]$^+$ 436.

Example 67

N-{3-[2-(3-Chloro-benzylamino)-pyrimidin-4-yl]-imidazo[1,2-a]pyrazin-8-yl}-cyclohexane-1,4-di-amine; hydrochloride 485.42

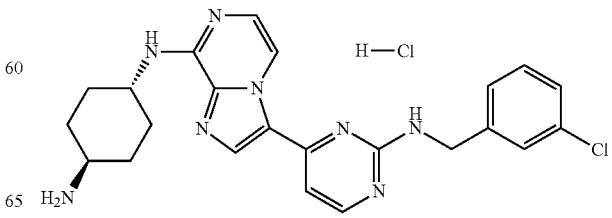

Step A (4-{3-[2-(3-Chloro-benzylamino)-pyrimidin-4-yl]-imidazo[1,2-a]pyrazin-8-ylamino}-cyclohexyl)-carbamic acid tert-butyl ester

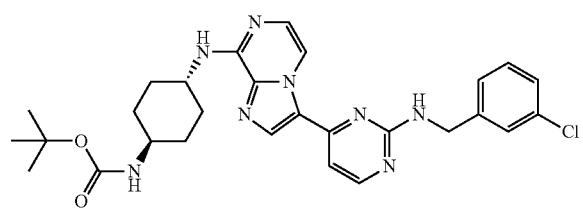 [SMILES: CC(C)(C)OC(=O)N[C@H]1CC[C@H](Nc2nccn3c(-c4ccnc(NCc5cccc(Cl)c5)n4)cnc23)CC1]

The mixture of {4-[3-(2-methanesulfinyl-pyrimidin-4-yl)-imidazo[1,2-a]pyrazin-8-ylamino]-cyclohexyl}-carbamic acid tert-butyl ester (from Example 48 supra) (100 mg, 0.212 mmol) and (3-chlorobenzylamine (120.3 mg, 0.849 mmol) was heated at 140° C. with stirring for 2 hours. The oil was purified by chromatography (silica gel, 10 g, 200-300 mesh, eluting with dichloromethane:methanol, 50:1 to 30:1) to afford crude (4-{3-[2-(3-chloro-benzylamino)-pyrimidin-4-yl]-imidazo[1,2-a]pyrazin-8-ylamino}-cyclohexyl)-carbamic acid tert-butyl ester. (Yield 80 mg). LC-MS: [M+H]+ 549.

Step B

N-{3-[2-(3-Chloro-benzylamino)-pyrimidin-4-yl]-imidazo[1,2-a]pyrazin-8-yl}-cyclohexane-1,4-diamine; hydrochloride

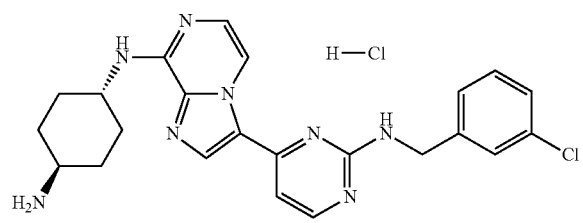 [SMILES: N[C@H]1CC[C@H](Nc2nccn3c(-c4ccnc(NCc5cccc(Cl)c5)n4)cnc23)CC1 ; Cl]

To a solution of crude (4-{3-[2-(3-chloro-benzylamino)-pyrimidin-4-yl]-imidazo[1,2-a]pyrazin-8-ylamino}-cyclohexyl)-carbamic acid tert-butyl ester (110 mg, 0.205 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N-{3-[2-(3-chloro-benzylamino)-pyrimidin-4-yl]-imidazo[1,2-a]pyrazin-8-yl}-cyclohexane-1,4-diamine; hydrochloride. (Yield 58 mg, 60.9%).

$^1$H NMR (300 MHz, CD$_3$OD): δ 8.75 (s, 1H), 8.45 (brs, 1H), 7.66-7.53 (m, 2H), 7.42-7.26 (m, 5H), 4.92 (brs, 2H), 4.07 (brs, 1H), 3.25 (brs, 1H), 2.23 (brs, 4H), 1.78-1.75 (m, 4H). LC-MS: [M+H]+ 450.

Example 68

N-[3-(2-Benzylamino-pyrimidin-4-yl)-imidazo[1,2-a]pyrazin-8-yl]-cyclohexane-1,4-diamine; hydrochloride 450.975

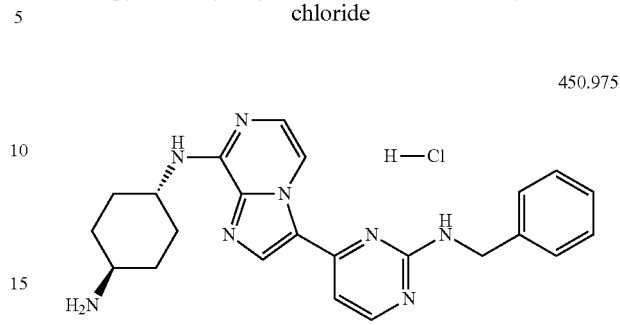

Step A

{4-[3-(2-Benzylamino-pyrimidin-4-yl)-imidazo[1,2-a]pyrazin-8-ylamino]-cyclohexyl}-carbamic acid tert-butyl ester

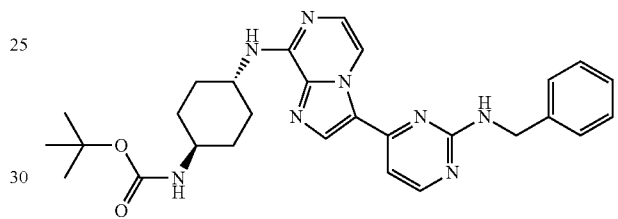

The mixture of {4-[3-(2-methanesulfinyl-pyrimidin-4-yl)-imidazo[1,2-a]pyrazin-8-ylamino]-cyclohexyl}-carbamic acid tert-butyl ester (from Example 48 supra) (130 mg, 0.276 mmol) and benzylamine (118.2 mg, 1.104 mmol) was heated at 140° C. with stirring for 2 hours. The oil was purified by chromatography (silica gel, 10 g, 200-300 mesh, eluting with dichloromethane:methanol, 50:1 to 30:1) to afford crude {4-[3-(2-benzylamino-pyrimidin-4-yl)-imidazo[1,2-a]pyrazin-8-ylamino]-cyclohexyl}-carbamic acid tert-butyl ester. (Yield 80 mg). LC-MS: [M+H]+ 515.

Step B

N-[3-(2-Benzylamino-pyrimidin-4-yl)-imidazo[1,2-a]pyrazin-8-yl]-cyclohexane-1,4-diamine; hydrochloride

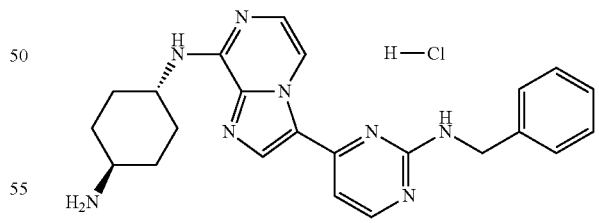

To a solution of crude {4-[3-(2-benzylamino-pyrimidin-4-yl)-imidazo[1,2-a]pyrazin-8-ylamino]-cyclohexyl}-carbamic acid tert-butyl ester (400 mg, 0.182 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N-[3-(2-benzylamino-pyrimidin-4-yl)-imidazo[1,2-a]pyrazin-8-yl]-cyclohexane-1,4-diamine; hydrochloride. (Yield 33 mg, 28.9%). ¹H NMR (300 MHz, CD₃OD): δ 8.73 (s, 1H), 8.45 (brs, 2H), 7.61-7.32 (m, 7H), 4.91 (brs, 2H), 4.11 (brs, 1H), 3.25 (brs, 1H), 2.23 (brs, 4H), 1.77-1.75 (m, 4H). LC-MS: [M+H]⁺ 415.

Example 69

(3-Amino-3-thiophen-3-yl-propyl)-carbamic acid tert-butyl ester

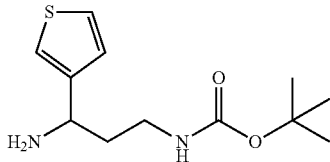 [SMILES: CC(C)(C)OC(=O)NCCC(N)c1ccsc1]

(3-Amino-3-thiophen-3-yl-propyl)-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A

3-Amino-1-thiophen-3-yl-propan-1-ol

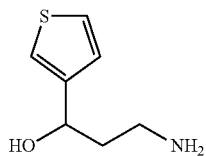

To a stirred suspension of LAH (1.45 g, 38.1 mmol) in dry THF (120 mL) was added a solution of 3-oxo-3-(thiophen-3-yl)propanenitrile (4.8 g, 31.8 mmol) in dry THF (40 mL) dropwise at 0° C. under nitrogen atmosphere. The mixture was warmed to 25° C. and then heated at 65° C. for 6 hours. After cooling to 0° C., a saturated solution of sodium hydroxide (2 mL) was added dropwise and the mixture was filtered. The filtrate was concentrated to dryness to give crude 3-amino-1-thiophen-3-yl-propan-1-ol which was used in next step without further purification. ¹H NMR (300 MHz, CDCl₃): δ 7.29-7.26 (m, 2H), 7.05 (dd, 1H, J₁=4.8 Hz, J₂=1.2 Hz), 5.04 (dd, 1H, J₁=8.1 Hz, J₂=3.0 Hz), 3.10-3.05 (m, 2H), 1.82-1.77 (m, 2H).

Step B (3-Hydroxy-3-thiophen-3-yl-propyl)-carbamic acid tert-butyl ester

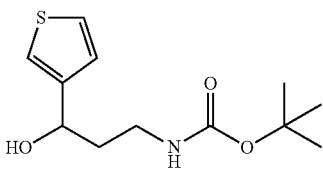 [SMILES: CC(C)(C)OC(=O)NCCC(O)c1ccsc1]

To a stirred solution of crude 3-amino-1-thiophen-3-yl-propan-1-ol (23 g) in THF (100 mL) was added Boc₂O (31.6 g, 146.3 mmol). The mixture was stirred at room temperature for 1 hour and then concentrated to dryness. The residue was purified by column chromatography (ethyl acetate:petroleum ether, 1:10) to afford (3-hydroxy-3-thiophen-3-yl-propyl)-carbamic acid tert-butyl ester. (Yield 21.5 g, 51% for two steps). ¹H NMR (300 MHz, CDCl₃): δ 8.08-8.06 (m, 1H), 7.55-7.53 (m, 1H), 7.34-7.30 (m, 1H), 5.10 (s, 1H), 3.52-3.48 (m, 2H), 3.13-3.09 (m, 2H), 1.42 (s, 9H). LC-MS: [M+Na]⁺ 280.

Step C 3-(1,3-Dioxo-1,3-dihydro-isoindol-2-yl)-3-thiophen-3-yl-propyl]-carbamic acid tert-butyl ester

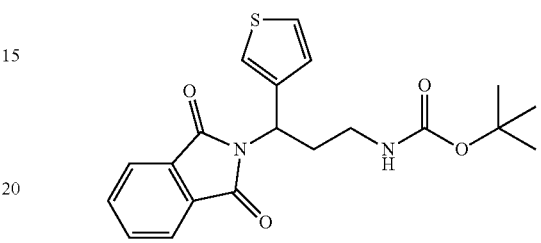

To a stirred solution of (3-hydroxy-3-thiophen-3-yl-propyl)-carbamic acid tert-butyl ester (21.5 g, 83.6 mmol), phthalimide (12.3 g, 83.6 mmol), and PPh₃ (28.5 g, 108.6 mmol) in THF (400 mL) was added DEAD (17.6 mL, 108.6 mmol) dropwise at 25° C. The mixture was stirred at room temperature for 14 hours, then concentrated. The residue was purified by column chromatography (ethyl acetate:petroleum ether, 1:6) to afford 3-(1,3-dioxo-1,3-dihydro-isoindol-2-yl)-3-thiophen-3-yl-propyl]-carbamic acid tert-butyl ester. (Yield 12 g, 38%).

¹H NMR (300 MHz, CDCl₃): δ 7.82-7.77 (m, 2H), 7.72-7.68 (m, 2H), 7.36 (d, 1H, J=1.8 Hz), 7.26-7.18 (m, 2H), 5.50 (dd, 1H, J₁=9.6 Hz, J₂=6 Hz), 4.65 (brs, 1H), 3.24-3.07 (m, 2H), 2.72-2.67 (m, 1H), 2.47-2.40 (m, 1H), 1.40 (s, 9H). LC-MS: [M+H−Boc]⁺ 287.

Step D (3-Amino-3-thiophen-3-yl-propyl)-carbamic acid tert-butyl ester

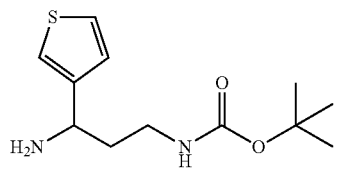 [SMILES: CC(C)(C)OC(=O)NCCC(N)c1ccsc1]

To a stirred solution of 3-(1,3-dioxo-1,3-dihydro-isoindol-2-yl)-3-thiophen-3-yl-propyl]-carbamic acid tert-butyl ester (12 g, 31.1 mmol) in methanol (150 mL) was added hydrazine hydrate (18 mL, 85% aqueous). The mixture was heated at reflux for 14 hours. After cooling to room temperature, the reaction mixture was filtered. The filtrate was concentrated and the residue was purified by column chromatography (methanol:dichloromethane, 1:50 to 1:20, 0.1% NH₃ H₂O) to afford (3-amino-3-thiophen-3-yl-propyl)-carbamic acid tert-butyl ester. (Yield 7.6 g, 95%). ¹H NMR (300 MHz, CDCl₃): δ 7.49 (s, 1H), 7.25-7.08 (m, 2H), 6.82 (brs, 1H), 3.85 (t, 1H, J=6.0 Hz), 3.18-2.95 (m, 4H), 1.75-1.62 (m, 2H), 1.37 (s, 9H). LC-MS: [M+H]⁺ 257.

Example 70

N1-{4-[8-(4-Methyl-piperazin-1-yl)-imidazo[1,2-a]pyrazin-3-yl]-pyrimidin-2-yl}-1-thiophen-3-yl-propane-1,3-diamine; hydrochloride 486.045

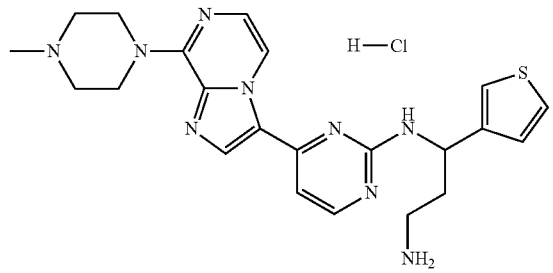

Step A (3-{4-[8-(4-Methyl-piperazin-1-yl)-imidazo[1,2-a]pyrazin-3-yl]-pyrimidin-2-ylamino}-3-thiophen-3-yl-propyl)-carbamic acid tert-butyl ester

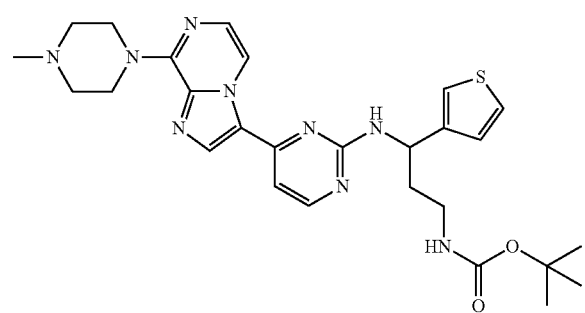 [SMILES: CN1CCN(c2nccn3c(-c4ccnc(NC(CCNC(=O)OC(C)(C)C)c5ccsc5)n4)cnc23)CC1]

The mixture of 3-(2-methanesulfonyl-pyrimidin-4-yl)-8-(4-methyl-piperazin-1-yl)-imidazo[1,2-a]pyrazine (from Example 46 supra) (150 mg, 0.402 mmol) and (3-amino-3-thiophen-3-yl-propyl)-carbamic acid tert-butyl ester (from Example 69 supra) (412 mg, 1.608 mmol) was heated at 140° C. with stirring for 2 hours. The oil was purified by chromatography (silica gel, 10 g, 200-300 mesh, eluting with dichloromethane:methanol, 50:1 to 20:1) to afford crude (3-{4-[8-(4-methyl-piperazin-1-yl)-imidazo[1,2-a]pyrazin-3-yl]-pyrimidin-2-ylamino}-3-thiophen-3-yl-propyl)-carbamic acid tert-butyl ester. (Yield 400 mg).

Step B

N1-{4-[8-(4-Methyl-piperazin-1-yl)-imidazo[1,2-a]pyrazin-3-yl]-pyrimidin-2-yl}-1-thiophen-3-yl-propane-1,3-diamine; hydrochloride

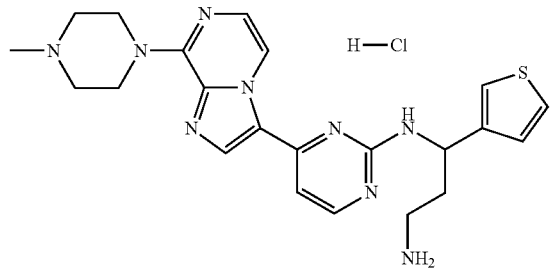 [SMILES: CN1CCN(c2nccn3c(-c4ccnc(NC(CCN)c5ccsc5)n4)cnc23)CC1 ; Cl]

To a solution of crude (3-{4-[8-(4-methyl-piperazin-1-yl)-imidazo[1,2-a]pyrazin-3-yl]-pyrimidin-2-ylamino}-3-thiophen-3-yl-propyl)-carbamic acid tert-butyl ester (400 mg, 0.182 mmol) in ethanol (3 mL) was added concentrated hydrochloric acid (3 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N1-{4-[8-(4-methyl-piperazin-1-yl)-imidazo[1,2-a]pyrazin-3-yl]-pyrimidin-2-yl}-1-thiophen-3-yl-propane-1,3-diamine; hydrochloride. (Yield 27 mg, 14.9%). $^1$H NMR (300 MHz, $CD_3OD$): δ 8.76 (s, 2H), 8.41 (brs, 1H), 7.68-7.52 (m, 4H), 7.32 (d, 1H, J=5.1 Hz), 5.55 (brs, 1H), 4.85 (brs, 2H), 3.75-3.72 (m, 4H), 3.40(brs, 2H), 3.18-3.15 (m, 2H), 3.00 (s, 3H), 2.44 (brs, 2H). LC-MS: [M+H]$^+$ 450.

Example 71

(4-Chloro-benzyl)-{6-[8-(4-methyl-piperazin-1-yl)-imidazo[1,2-a]pyrazin-3-yl]-pyridin-2-yl}-amine; hydrochloride 470.406

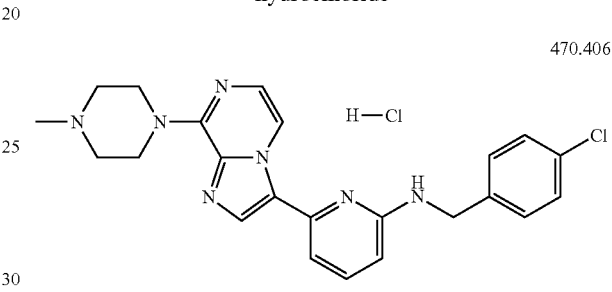

A mixture of 3-(6-bromo-pyridin-2-yl)-8-(4-methyl-piperazin-1-yl)-imidazo[1,2-a]pyrazine (from Example 39 supra) (0.373 g, 1.0 mmol), 4-chloro-benzylamine (0.14 g, 1.0 mmol), $Pd_2(dba)_3$ (60 mg), Davephos (80 mg), NaOtBu (140 mg, 1.46 mmol) suspended in dioxane (25 mL). The solution was bubbled with $N_2$ for several minutes and then heated under $N_2$ at 100° C. for 15 hours. The solution was then cooled to room temperature and filtered. The filtrate was concentrated under reduced pressure. The obtained crude product was purified by preparative-HPLC to give (4-chloro-benzyl)-{6-[8-(4-methyl-piperazin-1-yl)-imidazo[1,2-a]pyrazin-3-yl]-pyridin-2-yl}-amine; hydrochloride. (Yield 31 mg, 7.1%).
$^1$H NMR (300 MHz, $CD_3OD$): δ 8.54 (s, 1H), 8.23 (s, 1H), 7.76 (t, 1H, J=8.1 Hz), 7.42-7.35 (m, 4H), 7.25-7.20 (m, 2H), 6.88-6.85 (m, 1H), 5.50-5.46 (m, 2H), 4.65 (s, 2H), 3.78-3.74 (m, 4H), 3.42 (brs, 2H), 3.01 (s, 3H). LC-MS: [M+H]$^+$ 434.

Example 72

[3-(2-Benzylamino-pyrimidin-4-yl)-imidazo[1,2-a]pyrazin-8-yl]-(2-morpholin-4-yl-ethyl)-amine; hydrochloride 466.97

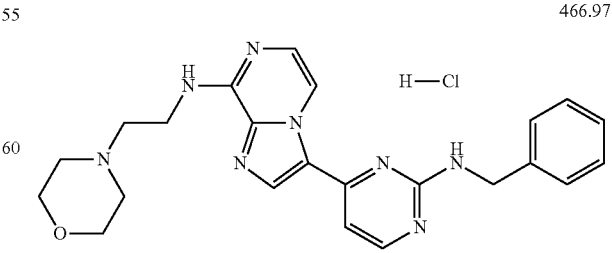

The mixture of [3-(2-methanesulfonyl-pyrimidin-4-yl)-imidazo[1,2-a]pyrazin-8-yl]-(2-morpholin-4-yl-ethyl)-amine (from Example 50 supra) (120 mg, 0.30 mmol) and benzylamine (128 mg, 1.19 mmol) was heated at 140° C. with stirring for 2 hours. The oil was purified by chromatography (silica gel, 10 g, 200-300 mesh, eluting with dichloromethane:methanol, 30:1 to 10:1) to afford the crude product (100 mg). The crude product was purified by prep-HPLC. Several drops of concentrated HCl were added to the fractions with product. After sonicating for several minutes, solution was concentrated under reduced pressure to afford [3-(2-benzylamino-pyrimidin-4-yl)-imidazo[1,2-a]pyrazin-8-yl]-(2-morpholin-4-yl-ethyl)-amine; hydrochloride. (Yield 25 mg, 19.5%). $^1$H NMR (300 MHz, CD$_3$OD): δ 8.77 (s, 1H), 8.57-8.38 (m, 2H), 7.62 (d, 1H, J=6.6 Hz), 7.48-7.34 (m, 6H), 4.82 (brs, 2H), 4.21 (brs, 2H), 3.99 (brs, 4H), 3.63-3.47 (m, 6H). LC-MS: [M+H]$^+$ 431.

Example 73

N-[3-(6-Benzylamino-pyridin-2-yl)-imidazo[1,2-a]pyrazin-8-yl]-cyclohexane-1,4-diamine; hydrochloride 449.99

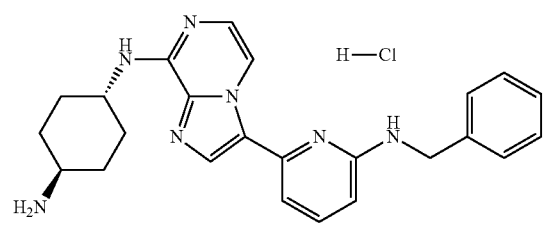

Step A

{4-[3-(6-Benzylamino-pyridin-2-yl)-imidazo[1,2-a]pyrazin-8-ylamino]-cyclohexyl}-carbamic acid tert-butyl ester

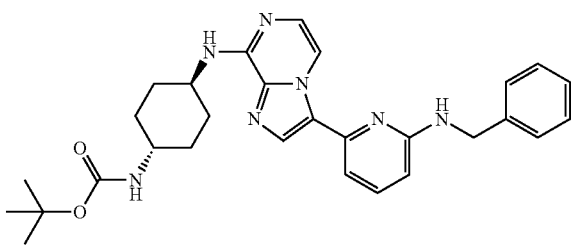 [SMILES: CC(C)(C)OC(=O)N[C@H]1CC[C@H](Nc2nccn3c(-c4cccc(NCc5ccccc5)n4)cnc23)CC1]

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.487 g, 1.0 mmol), benzylamine (0.214 g, 2.0 mmol), Pd$_2$(dba)$_3$ (60 mg), Davephos (80 mg), NaOtBu (140 mg, 1.46 mmol) in dioxane (25 mL) in a sealed tube was bubbled with N$_2$ for several minutes and then heated under N$_2$ at 110° C. for 15 hours. The solution was then cooled to room temperature and filtered. The filtrate was concentrated under reduced pressure. The obtained crude product was purified by preparative-HPLC to give {4-[3-(6-benzylamino-pyridin-2-yl)-imidazo[1,2-a]pyrazin-8-ylamino]-cyclohexyl}-carbamic acid tert-butyl ester. (Yield 80 mg). LC-MS: [M+H]$^+$ 514.

Step B

N-[3-(6-benzylamino-pyridin-2-yl)-imidazo[1,2-a]pyrazin-8-yl]-cyclohexane-1,4-diamine; hydrochloride

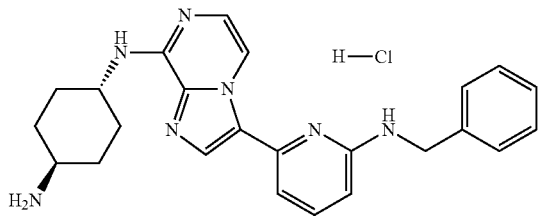 [SMILES: N[C@H]1CC[C@H](Nc2nccn3c(-c4cccc(NCc5ccccc5)n4)cnc23)CC1 ; Cl]

The mixture of {4-[3-(6-benzylamino-pyridin-2-yl)-imidazo[1,2-a]pyrazin-8-ylamino]-cyclohexyl}-carbamic acid tert-butyl ester (80 mg, 0.156 mmol) in ethanol (4 mL) and concentrated HCl (4 mL) was stirred at room temperature for 15 hours. The reaction mixture was then concentrated under reduced pressure. The obtained crude product was purified by preparative-HPLC to give N-[3-(6-benzylamino-pyridin-2-yl)-imidazo[1,2-a]pyrazin-8-yl]-cyclohexane-1,4-diamine; hydrochloride. (Yield 50 mg).
$^1$H NMR (300 MHz, CD$_3$OD): δ 8.16 (s, 1H), 8.06 (d, 1H, J=5.7 Hz), 7.93 (t, 1H, J=8.4 Hz), 7.45-7.17 (m, 7H), 7.09 (d, 1H, J=9.0 Hz), 4.70 (s, 2H), 4.04 (brs, 1H), 3.23 (brs, 1H), 2.22-2.15 (m, 4H), 1.80-1.75 (m, 4H). LC-MS: [M+H]$^+$ 414.

Example 74

(2-Amino-2-thiophen-3-yl-ethyl)-carbamic acid tert-butyl ester

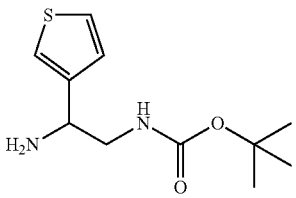 [SMILES: CC(C)(C)OC(=O)NCC(N)c1ccsc1]

(2-Amino-2-thiophen-3-yl-ethyl)-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.
Step A Hydroxy-thiophen-3-yl-acetonitrile

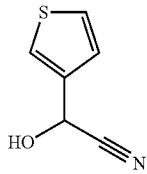

To a stirred suspension of KCN (18.6 g, 286 mmol) in methanol (100 mL) was added thiophene-3-carbaldehyde (20 mL, 178 mmol) at 0° C. under nitrogen atmosphere. Then acetic acid (4.4 mL) was added dropwise at 0° C. After 30 minutes, the mixture was warmed to 15° C. and stirred for 20 hours. NaHCO$_3$ (15 g) was added. The mixture was concentrated and extracted with ethyl acetate (200 mL). The organic mixture was washed with water (3×25 mL), brine (25 mL), dried over anhydrous sodium sulfate and concentrated to dryness. The residue was purified by column chromatography (ethyl acetate:petroleum ether, 1:10) to afford hydroxy-thiophen-3-yl-acetonitrile. (Yield 15 g, 60%). LC-MS: [M+Na]+ 162.
Step B 2-Amino-1-thiophen-3-yl-ethanol

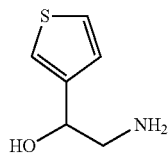

To a stirred suspension of LAH (8.7 g, 225 mmol) in dry THF (300 mL) was added a solution of hydroxy-thiophen-3-yl-acetonitrile (12.5 mL, 90 mmol) in dry THF (50 mL) dropwise at 0° C. under nitrogen atmosphere. Then the mixture was warmed to 25° C. and stirred overnight. After cooling to 10° C., H$_2$O (8.7 mL) was added to the solution, followed by NaOH solution (8.7 mL, 15%), then H$_2$O (26 mL). The reaction mixture was filtered and the filtrate was concentrated to dryness to afford crude 2-amino-1-thiophen-3-yl-ethanol. (Yield 12.9 g, crude). LC-MS: [M+H]+ 144.
Step C (2-Hydroxy-2-thiophen-3-yl-ethyl)-carbamic acid tert-butyl ester

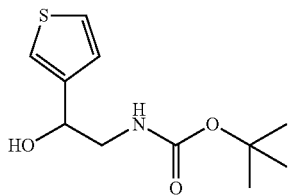 [SMILES: CC(C)(C)OC(=O)NCC(O)c1ccsc1]

To a stirred solution of crude 2-amino-1-thiophen-3-yl-ethanol (12.9 g, crude) in THF (150 mL) was added Boc$_2$O (21.6 g, 99 mmol). After stirring for 1 hour, the mixture was concentrated to dryness which was purified by column chromatography (ethyl acetate:petroleum ether, 1:5) to afford (2-hydroxy-2-thiophen-3-yl-ethyl)-carbamic acid tert-butyl ester. (Yield 15.3 g, 70%). LC-MS: [M+Na]+ 266.
Step D

[2-(1,3-Dioxo-1,3-dihydro-isoindol-2-yl)-2-thiophen-3-yl-ethyl]-carbamic acid tert-butyl ester

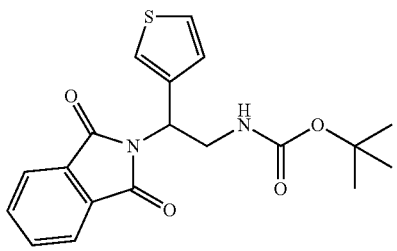 [SMILES: CC(C)(C)OC(=O)NCC(c1ccsc1)N1C(=O)c2ccccc2C1=O]

To a stirred solution of (2-hydroxy-2-thiophen-3-yl-ethyl)-carbamic acid tert-butyl ester (15.3 g, 63 mmol), pathalimide (9.5 g, 63 mmol), PPh$_3$ (21.4 g, 82 mmol) in THF (400 mL) was added DEAD (12.6 mL, 82 mmol) dropwise at 25° C. After 20 hours, the mixture was concentrated to dryness. The residue was purified by column chromatography (ethyl acetate:petroleum ether, 1:6) to afford crude [2-(1,3-dioxo-1,3-dihydro-isoindol-2-yl)-2-thiophen-3-yl-ethyl]-carbamic acid tert-butyl ester. (Yield 23 g).
LC-MS: [M+Na]+ 395.
Step E (2-Amino-2-thiophen-3-yl-ethyl)-carbamic acid tert-butyl ester

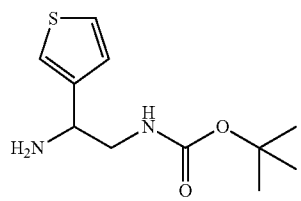 [SMILES: CC(C)(C)OC(=O)NCC(N)c1ccsc1]

To a stirred solution of [2-(1,3-dioxo-1,3-dihydro-isoindol-2-yl)-2-thiophen-3-yl-ethyl]-carbamic acid tert-butyl ester (23 g, crude) in THF (100 mL) and methanol (100 mL) was added hydrazine hydrate (63 g, 1.26 mol). The mixture was heated to 60° C. for 2 hours and then cooled to 20° C. The reaction mixture was filtered and the filtration was concentrated to dryness. The residue was purified by column chromatography (methanol:dichloromethane, 1:50) to afford (2-amino-2-thiophen-3-yl-ethyl)-carbamic acid tert-butyl ester. (Yield 8.6 g, 57% for the two steps). LC-MS: [M+H]+ 243.

Example 75

N1-{4-[8-(4-Methyl-piperazin-1-yl)-imidazo[1,2-a]pyrazin-3-yl]-pyrimidin-2-yl}-1-thiophen-3-yl-ethane-1,2-di amine; hydrochloride 472.02

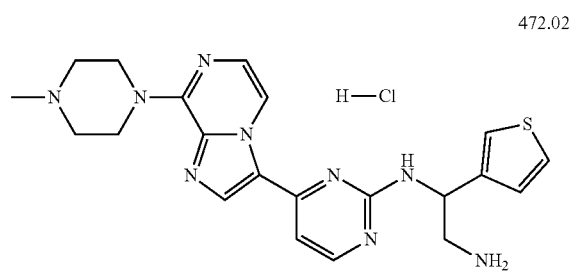 [SMILES: CN1CCN(c2nccn3c(-c4ccnc(NC(CN)c5ccsc5)n4)cnc23)CC1 ; Cl]

Step A (2-{4-[8-(4-Methyl-piperazin-1-yl)-imidazo[1,2-a]pyrazin-3-yl]-pyrimidin-2-ylamino}-2-thiophen-3-yl-ethyl)-carbamic acid tert-butyl ester

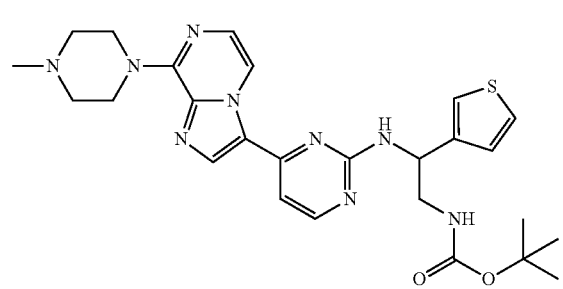 [SMILES: CN1CCN(c2nccn3c(-c4ccnc(NC(CNC(=O)OC(C)(C)C)c5ccsc5)n4)cnc23)CC1]

The mixture of 3-(2-methanesulfonyl-pyrimidin-4-yl)-8-(4-methyl-piperazin-1-yl)-imidazo[1,2-a]pyrazine (from Example 46 supra) (200 mg, 0.536 mmol) and (2-amino-2-thiophen-3-yl-ethyl)-carbamic acid tert-butyl ester (from Example 74 supra) (520 mg, 2.14 mmol) was heated at 140° C., with stirring for 2 hours. The oil was purified by chromatography (silica gel, 10 g, 200-300 mesh, eluting with dichloromethane:methanol, 10:1 to 4:1) to afford crude (2-{4-[8-(4-methyl-piperazin-1-yl)-imidazo[1,2-a]pyrazin-3-yl]-pyrimidin-2-ylamino}-2-thiophen-3-yl-ethyl)-carbamic acid tert-butyl ester. (yield 150 mg). LC-MS: [M+H]+ 536.

Step B

N1-{4-[8-(4-Methyl-piperazin-1-yl)-imidazo[1,2-a]pyrazin-3-yl]-pyrimidin-2-yl}-1-thiophen-3-yl-ethane-1,2-di amine; hydrochloride

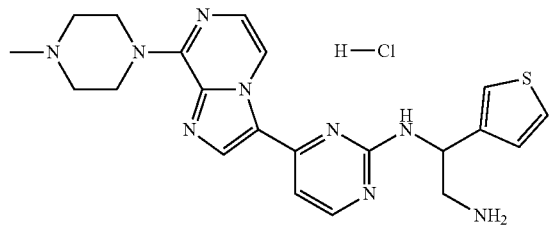 [SMILES: CN1CCN(c2nccn3c(-c4ccnc(NC(CN)c5ccsc5)n4)cnc23)CC1 ; Cl]

To a solution of crude (2-{4-[8-(4-methyl-piperazin-1-yl)-imidazo[1,2-a]pyrazin-3-yl]-pyrimidin-2-ylamino}-2-thiophen-3-yl-ethyl)-carbamic acid tert-butyl ester (150 mg, 0.280 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N1-{4-[8-(4-methyl-piperazin-1-yl)-imidazo[1,2-a]pyrazin-3-yl]-pyrimidin-2-yl}-1-thiophen-3-yl-ethane-1,2-diamine; hydrochloride. (Yield 13 mg, 5.57%). $^1$H NMR (300 MHz, CD$_3$OD): δ 8.81 (brs, 1H), 8.63 (s, 1H), 8.29 (d, 1H, J=6.0 Hz), 7.61-7.52 (m, 3H), 7.46-7.43 (m, 1H), 7.23 (d, 1H, J=5.1 Hz), 5.72 (brs, 1H), 5.47-5.43 (m, 2H), 3.63-3.60 (m, 4H), 3.50-3.48 (m, 2H), 3.29-3.26 (m, 2H), 2.89 (s, 3H). LC-MS: [M+H]+ 436.

Example 76

N-{3-[2-(3-Amino-1-phenyl-propylamino)-pyrimidin-4-yl]-imidazo[1,2-a]pyrazin-8-yl}-cyclohexane-1,4-diamine; hydrochloride 494.04

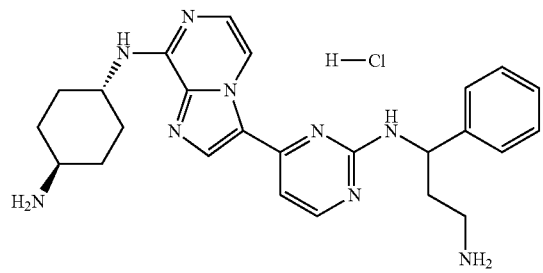 [SMILES: NCCC(Nc1nccc(-c2cnc3c(N[C@H]4CC[C@H](N)CC4)nccn23)n1)c1ccccc1 ; Cl]

Step A (4-{3-[2-(3-tert-Butoxycarbonylamino-1-phenyl-propylamino)-pyrimidin-4-yl]-imidazo[1,2-a]pyrazin-8-ylamino}-cyclohexyl)-carbamic acid tert-butyl ester

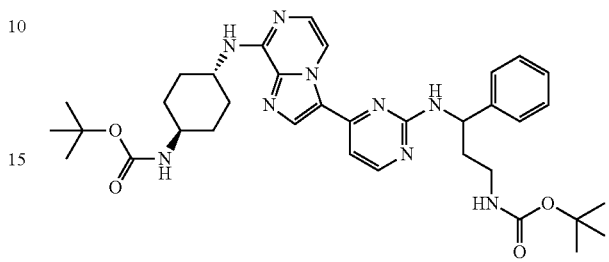

The mixture of {4-[3-(2-methanesulfinyl-pyrimidin-4-yl)-imidazo[1,2-a]pyrazin-8-ylamino]-cyclohexyl}-carbamic acid tert-butyl ester (from Example 48 supra) (170 mg, 0.36 mmol) and compound (3-amino-3-phenyl-propyl)-carbamic acid tert-butyl ester (from Example 53 supra) (361 mg, 1.44 mmol) was heated at 140° C. with stirring for 2 hours. The oil was purified by chromatography (silica gel, 10 g, 200-300 mesh, eluting with dichloromethane:methanol, 50:1 to 30:1) to afford crude (4-{3-[2-(3-tert-butoxycarbonylamino-1-phenyl-propylamino)-pyrimidin-4-yl]-imidazo[1,2-a]pyrazin-8-ylamino}-cyclohexyl)-carbamic acid tert-butyl ester. (Yield 110 mg).
LC-MS: [M+H]+ 658.

Step B

N-{3-[2-(3-Amino-1-phenyl-propylamino)-pyrimidin-4-yl]-imidazo[1,2-a]pyrazin-8-yl}-cyclohexane-1,4-diamine; hydrochloride

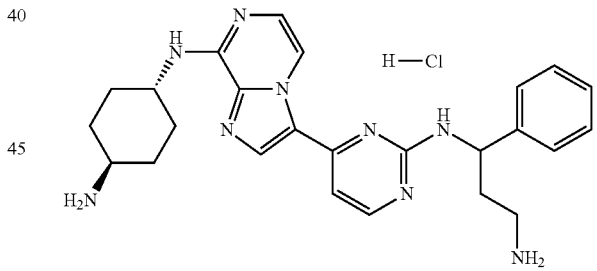

To a solution of crude (4-{3-[2-(3-tert-butoxycarbonylamino-1-phenyl-propylamino)-pyrimidin-4-yl]-imidazo[1,2-a]pyrazin-8-ylamino}-cyclohexyl)-carbamic acid tert-butyl ester (110 mg, 0.17 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N-{3-[2-(3-amino-1-phenyl-propylamino)-pyrimidin-4-yl]-imidazo[1,2-a]pyrazin-8-yl}-cyclohexane-1,4-diamine; hydrochloride. (Yield 27 mg, 16.4%). $^1$H NMR (300 MHz, CD$_3$OD): δ 8.67 (s, 2H), 8.43 (brs, 1H), 7.57-7.55(m, 3H), 7.44-7.31(m, 4H), 5.38 (s, 1H), 4.08 (brs, 1H), 3.21-3.16(m, 3H), 2.42-2.25(m, 6H), 1.75-1.73(m, 4H).
LC-MS: [M+H]+ 458.

Example 77

N-{3-[2-(2-Amino-1-phenyl-ethylamino)-pyrimidin-4-yl]-imidazo[1,2-a]pyrazin-8-yl}-cyclohexane-1,4-diamine; hydrochloride

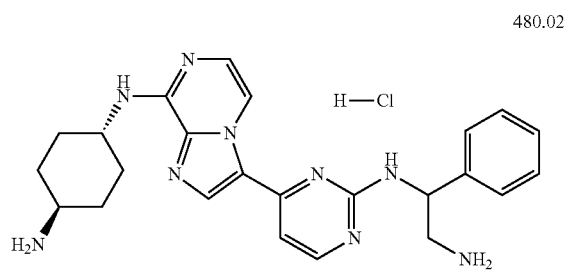 [SMILES: NCC(Nc1nccc(-c2cnc3c(N[C@H]4CC[C@H](N)CC4)nccn23)n1)c1ccccc1 ; Cl]

480.02

Step A (4-{3-[2-(2-tert-Butoxycarbonylamino-1-phenyl-ethylamino)-pyrimidin-4-yl]-imidazo[1,2-a]pyrazin-8-ylamino}-cyclohexyl)-carbamic acid tert-butyl ester

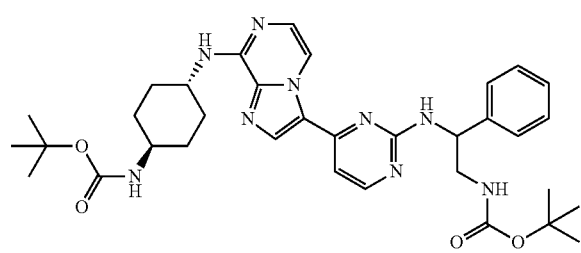 [SMILES: CC(C)(C)OC(=O)NCC(Nc1nccc(-c2cnc3c(N[C@H]4CC[C@H](NC(=O)OC(C)(C)C)CC4)nccn23)n1)c1ccccc1]

The mixture of {4-[3-(2-methanesulfinyl-pyrimidin-4-yl)-imidazo[1,2-a]pyrazin-8-ylamino]-cyclohexyl}-carbamic acid tert-butyl ester (from Example 48 supra) (170 mg, 0.36 mmol) and (2-amino-2-phenyl-ethyl)-carbamic acid tert-butyl ester (from Example 51 supra) (341 mg, 1.44 mmol) was heated at 140° C. with stirring for 2 hours. The oil was purified by chromatography (silica gel, 10 g, 200-300 mesh, eluting with dichloromethane:methanol, 50:1 to 30:1) to afford crude (4-{3-[2-(2-tert-butoxycarbonylamino-1-phenyl-ethylamino)-pyrimidin-4-yl]-imidazo[1,2-a]pyrazin-8-ylamino}-cyclohexyl)-carbamic acid tert-butyl ester. (Yield 100 mg). LC-MS: [M+H]$^+$ 644.

Step B

N-{3-[2-(2-Amino-1-phenyl-ethylamino)-pyrimidin-4-yl]-imidazo[1,2-a]pyrazin-8-yl}-cyclohexane-1,4-diamine; hydrochloride

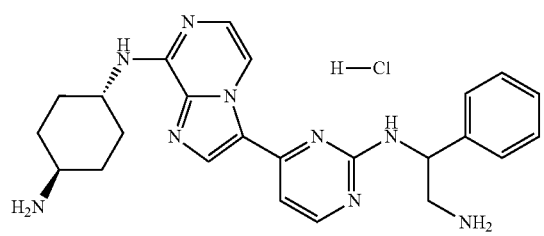 [SMILES: NCC(Nc1nccc(-c2cnc3c(N[C@H]4CC[C@H](N)CC4)nccn23)n1)c1ccccc1 ; Cl]

To a solution of crude (4-{3-[2-(2-tert-butoxycarbonylamino-1-phenyl-ethylamino)-pyrimidin-4-yl]-imidazo[1,2-a]pyrazin-8-ylamino}-cyclohexyl)-carbamic acid tert-butyl ester (100 mg, 0.16 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N-{3-[2-(2-amino-1-phenyl-ethylamino)-pyrimidin-4-yl]-imidazo[1,2-a]pyrazin-8-yl}-cyclohexane-1,4-diamine; hydrochloride. (Yield 26 mg, 16.3%). $^1$H NMR (300 MHz, CD$_3$OD): δ 8.68 (s, 2H), 8.46 (brs, 1H), 7.63-7.61(m, 3H), 7.46-7.32(m, 4H), 5.78 (s, 1H), 4.05 (brs, 1H), 3.61-3.48(m, 2H), 3.23 (brs, 1H), 2.22 (brs, 4H), 1.76-1.71(m, 4H).

LC-MS: [M+H]$^+$ 444.

Example 78

[2-Amino-2-(3-chloro-phenyl)-ethyl]-carbamic acid tert-butyl ester

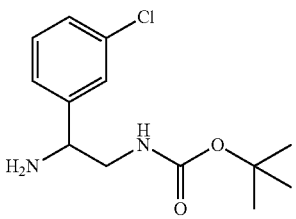 [SMILES: CC(C)(C)OC(=O)NCC(N)c1cccc(Cl)c1]

[2-Amino-2-(3-chloro-phenyl)-ethyl]-carbamic acid tert-butyl ester was prepared in an analogous process according to the literature procedure of Seefeld, M. A.; Rouse, M. B.; Heerding, D. A.; Peace, S.; Yamashita, D. S.; McNulty, K. C. WO 2008/098104, Aug. 14, 2008.

Step A (3-Chloro-phenyl)-hydroxy-acetonitrile

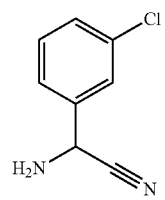 [SMILES: N#CC(N)c1cccc(Cl)c1]

To a stirred suspension of KCN (5.04 g, 78 mmol) in methanol (20 mL) was added 3-chlorobenzaldehyde (7.0 g, 50 mmol) at 0° C. under nitrogen atmosphere. Then acetic acid (4.4 mL) was added dropwise at 0° C. After 30 minutes, the mixture was warmed to 15° C. and stirred for 5 hours. Then the reaction mixture was concentrated to dryness and extracted with ethyl acetate (200 mL). The organic solution was washed with water (3×25 mL), brine (25 mL), dried over anhydrous sodium sulfate and concentrated to dryness. The resulting residue was purified by column chromatography (ethyl acetate:petroleum ether, 1:15) to afford (3-chloro-phenyl)-hydroxy-acetonitrile. (Yield 8.2 g, 97%). LC-MS: [M+Na]$^+$ 190.

Step B

2-Amino-1-(3-chloro-phenyl)-ethanol

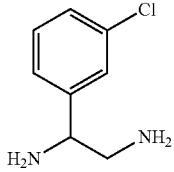

To a stirred suspension of LAH (2.36 g, 59 mmol) in dry THF (70 mL) was added a solution of (3-chloro-phenyl)-hydroxy-acetonitrile (4.0 g, 24 mmol) in dry THF (55 mL) dropwise at 0° C. under nitrogen atmosphere. The mixture was warmed to 25° C. and then heated at 60° C. for 2 hours. After cooling to 0° C., a saturated solution of sodium hydroxide was added dropwise and extracted with dichloromethane (200 mL). The organic solution was dried over anhydrous sodium sulfate and concentrated to dryness. The residue was purified by column chromatography (methanol:dichloromethane, 1:10) to afford 2-amino-1-(3-chloro-phenyl)-ethanol. (Yield 2.86 g, 70%). LC-MS: [M+H]$^+$ 172.

Step C

[2-(3-Chloro-phenyl)-2-hydroxy-ethyl]carbamic acid tert-butyl ester

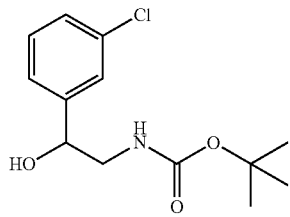 [SMILES: CC(C)(C)OC(=O)NCC(O)c1cccc(Cl)c1]

To a stirred solution of 2-amino-1-(3-chloro-phenyl)-ethanol (2.86 g, 16.7 mmol) in THF (100 mL) was added Boc$_2$O (4.3 g, 20 mmol). After 1 hour, the mixture was concentrated to dryness. The residue was purified by column chromatography (methanol:dichloromethane, 1:100) to afford [2-(3-chloro-phenyl)-2-hydroxy-ethyl]-carbamic acid tert-butyl ester. (Yield 3.9 g, 72%). LC-MS: [M+Na]$^+$ 294.

Step D

[2-(3-Chloro-phenyl)-2-(1,3-di oxo-1,3-dihydro-isoindol-2-yl)-ethyl]-carbamic acid tert-butyl ester

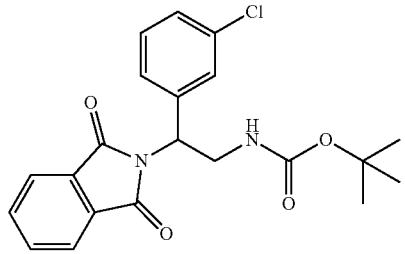 [SMILES: CC(C)(C)OC(=O)NCC(c1cccc(Cl)c1)N1C(=O)c2ccccc2C1=O]

To a stirred solution of [2-(3-chloro-phenyl)-2-hydroxy-ethyl]carbamic acid tert-butyl ester (20 g, 73.5 mmol), phthalimide (11.1 g, 73.5 mmol) and PPh$_3$ (25.1 g, 95.5 mmol) in THF (500 mL) was added DEAD (11.4 mL, 95.5 mmol) dropwise at −5 to 0° C. The reaction mixture was stirred at room temperature for 3 hours. Then the mixture was concentrated to dryness. The residue was purified by column chromatography (ethyl acetate:petroleum ether, 1:10) to afford [2-(3-chloro-phenyl)-2-(1,3-dioxo-1,3-dihydro-isoindol-2-yl)-ethyl]-carbamic acid tert-butyl ester. (Yield 20 g, 69%). LC-MS: [M+H]$^+$ 401.

Step E

[2-Amino-2-(3-chloro-phenyl)-ethyl]carbamic acid tert-butyl ester

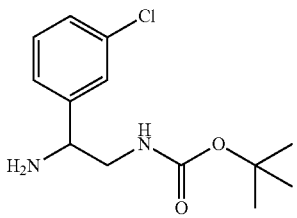 [SMILES: CC(C)(C)OC(=O)NCC(N)c1cccc(Cl)c1]

To a stirred solution of [2-(3-chloro-phenyl)-2-(1,3-dioxo-1,3-dihydro-isoindol-2-yl)-ethy]-carbamic acid tert-butyl ester (2.5 g, 6.2 mmol) in THF (10 mL) and methanol (10 mL) was added hydrazine hydrate (3.1 g, 62 mmol). The mixture was heated a 55° C. for 1 hour. Then it was concentrated to dryness, dissolved in H$_2$O (5 mL) and extracted with ethyl acetate (50 mL). The organic mixture was concentrated and purified by column chromatography (methanol:dichloromethane, 1:100) to afford [2-amino-2-(3-chloro-phenyl)-ethyl]-carbamic acid tert-butyl ester. (Yield 1.325 g, 79%). LC-MS: [M+H]$^+$ 271.

Example 79

1-(3-Chloro-phenyl)-N1-{4-[8-(4-methyl-piperazin-1-yl)-imidazo[1,2-a]pyrazin-3-yl]-pyrimidin-2-yl}-ethane-1,2-diamine; hydrochloride 500.44

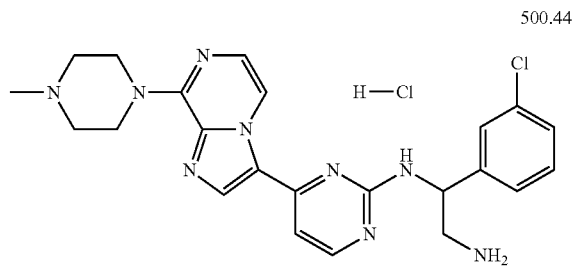 [SMILES: CN1CCN(c2nccn3c(-c4ccnc(NC(CN)c5cccc(Cl)c5)n4)cnc23)CC1 ; Cl]

Step A (2-(3-Chloro-phenyl)-2-{4-[8-(4-methyl-piperazin-1-yl)-imidazo[1,2-a]pyrazin-3-yl]-pyrimidin-2-ylamino}-ethyl)-carbamic acid tert-butyl ester

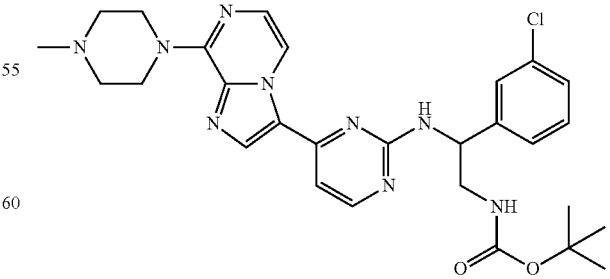

The mixture of 3-(2-methanesulfonyl-pyrimidin-4-yl)-8-(4-methyl-piperazin-1-yl)-imidazo[1,2-a]pyrazine (from Example 46 supra) (210 mg, 0.563 mmol) and [2-amino-2-(3-chloro-phenyl)-ethyl]-carbamic acid tert-butyl ester (from Example 78 supra) (611 mg, 2.25 mmol) was heated at 140° C. with stirring for 2 hours. The oil was purified by chromatography (silica gel, 10 g, 200-300 mesh, eluting with dichloromethane:methanol, 10:1 to 4:1) to afford crude (2-(3-chloro-phenyl)-2-{4-[8-(4-methyl-piperazin-1-yl)-imidazo[1,2-a]pyrazin-3-yl]-pyrimidin-2-ylamino}-ethyl)-carbamic acid tert-butyl ester. (Yield 150 mg). LC-MS: [M+H]+ 564.

Step B 1-(3-Chloro-phenyl)-N-1-{-4-[8-(4-methyl-piperazin-1-yl)-imidazo[1,2-a]pyrazin-3-yl]-pyrimidin-2-yl}-ethane-1,2-diamine; hydrochloride

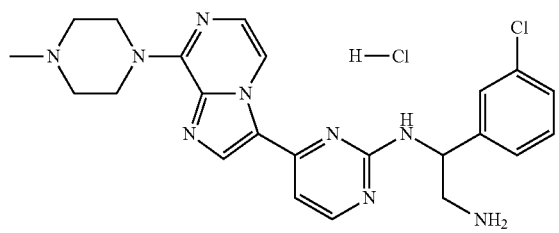 [SMILES: CN1CCN(c2nccn3c(-c4ccnc(NC(CN)c5cccc(Cl)c5)n4)cnc23)CC1 ; Cl]

To a solution of crude (2-(3-chloro-phenyl)-2-{4-[8-(4-methyl-piperazin-1-yl)-imidazo[1,2-a]pyrazin-3-yl]-pyrimidin-2-ylamino}-ethyl)-carbamic acid tert-butyl ester (150 mg, 0.266 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford 1-(3-chloro-phenyl)-N1-{4-[8-(4-methyl-piperazin-1-yl)-imidazo[1,2-a]pyrazin-3-yl]-pyrimidin-2-yl}-ethane-1,2-diamine; hydrochloride. (Yield 28 mg, 10.7%). $^1$H NMR (300 MHz, CD$_3$OD): δ 8.79 (brs, 1H), 8.59 (s, 1H), 8.30 (d, 1H, J=6.3 Hz), 7.59-7.45 (m, 4H), 7.37-7.27 (m, 2H), 5.62 (brs, 1H), 5.45 (brs, 2H), 3.64-3.60 (m, 4H), 3.48-3.38 (m, 4H), 2.89 (s, 3H). LC-MS: [M+H]+ 465.

Example 80

N-{3-[6-(2-Amino-1-phenyl-ethylamino)-pyridin-2-yl]-imidazo[1,2-a]pyrazin-8-yl}-cyclohexane-1,4-diamine; hydrochloride 479.03

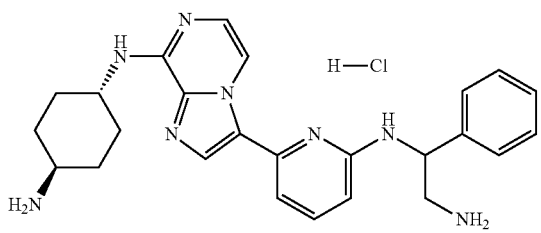 [SMILES: NCC(Nc1cccc(-c2cnc3c(N[C@H]4CC[C@H](N)CC4)nccn23)n1)c1ccccc1 ; Cl]

Step A (4-{3-[6-(2-tert-Butoxycarbonylamino-1-phenyl-ethylamino)-pyridin-2-yl]-imidazo[1,2-a]pyrazin-8-ylamino}-cyclohexyl)-carbamic acid tert-butyl ester

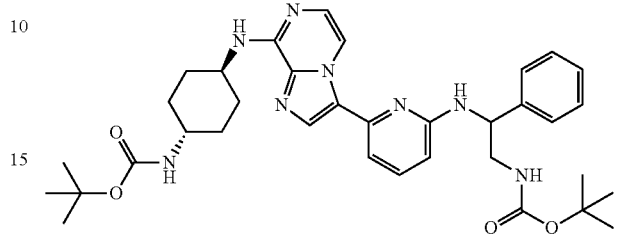

A sealed tube was charged with the mixture of {4-[3-(6-bromo-pyridin-2-yl)-imidazo[1,2-a]pyrazin-8-ylamino]-cyclohexyl}-carbamic acid tert-butyl ester (from Example 40 supra) (487 mg, 1.0 mmol), compound (2-amino-2-phenyl-ethyl)-carbamic acid tert-butyl ester (from Example 51 supra) (354 mg, 1.5 mmol), Pd$_2$(dba)$_3$ (46 mg, 0.05 mmol), Davephos (78 mg, 0.2 mmol), K$_2$CO$_3$ (207 mg, 1.5 mmol) and dioxane (20 mL). The mixture was bubbled with N$_2$ for several minutes and then heated under N$_2$ at 135° C. for 17 hours. The solution was then cooled to room temperature and filtered. The filtrate was concentrated under reduced pressure. The residue was purified by chromatography (CH$_2$Cl$_2$:MeOH, 100:1) to give crude (4-{3-[6-(2-tert-butoxycarbonylamino-1-phenyl-ethylamino)-pyridin-2-yl]-imidazo[1,2-a]pyrazin-8-ylamino}-cyclohexyl)-carbamic acid tert-butyl ester. (Yield 0.38 g).

Step B

N-{3-[6-(2-Amino-1-phenyl-ethylamino)-pyridin-2-yl]-imidazo[1,2-a]pyrazin-8-yl}-cyclohexane-1,4-diamine; hydrochloride

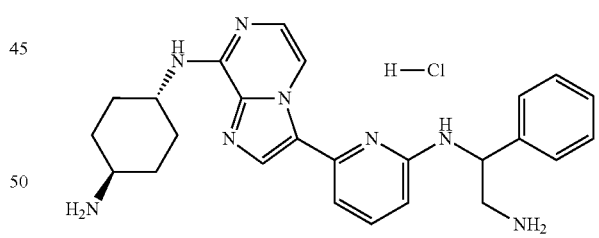

To a solution of (4-{3-[6-(2-tert-butoxycarbonylamino-1-phenyl-ethylamino)-pyridin-2-yl]-imidazo[1,2-a]pyrazin-8-ylamino}-cyclohexyl)-carbamic acid tert-butyl ester (0.38 g, crude) in ethanol (4 mL) was added concentrated HCl (8 mL). The reaction mixture was stirred at room temperature for 15 hour and then concentrated under reduced pressure. The residue was purified by prep-HPLC to give N-{3-[6-(2-amino-1-phenyl-ethylamino)-pyridin-2-yl]-imidazo[1,2-a]pyrazin-8-yl}-cyclohexane-1,4-diamine; hydrochloride. (Yield 47 mg). $^1$H NMR (300 MHz, CD$_3$OD): δ 8.45 (d, 1H, J=5.7 Hz), 8.13 (s, 1H), 7.65 (t, 1H, J=7.2 Hz), 7.53-7.51 (m, 2H), 7.43-7.06 (m, 5H), 6.85 (d, 1H, J=8.7 Hz), 5.47-5.41 (m, 1H), 4.03 (brs, 1H), 3.43-3.23 (m, 3H), 2.20 (brs, 4H), 1.73 (brs, 4H). LC-MS: [M+H]+ 443.

Example 81

N-{3-[6-(3-Amino-1-phenyl-propylamino)-pyridin-2-yl]-imidazo[1,2-a]pyrazin-8-yl}-cyclohexane-1,4-diamine; hydrochloride 493.06

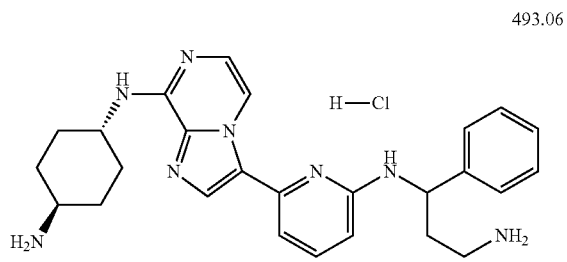 [SMILES: NCCC(Nc1cccc(-c2cnc3c(N[C@H]4CC[C@H](N)CC4)nccn23)n1)c1ccccc1 ; Cl]

Step A (4-{3-[6-(3-tert-Butoxycarbonylamino-1-phenyl-propylamino)-pyridin-2-yl]-imidazo[1,2-a]pyrazin-8-ylamino}-cyclohexyl)-carbamic acid tert-butyl ester

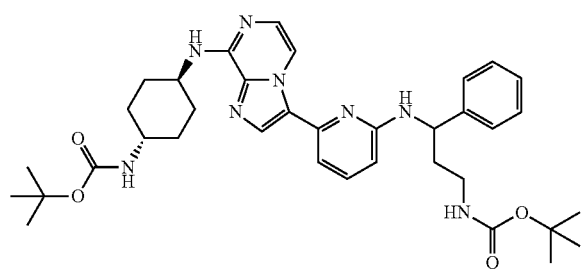 [SMILES: CC(C)(C)OC(=O)NCCC(Nc1cccc(-c2cnc3c(N[C@H]4CC[C@H](NC(=O)OC(C)(C)C)CC4)nccn23)n1)c1ccccc1]

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.487 g, 1.0 mmol), (3-amino-3-phenyl-propyl)-carbamic acid tert-butyl ester (from Example 53 supra) (0.375 g, 1.5 mmol), $Pd_2(dba)_3$ (60 mg), Davephos (80 mg), $K_2CO_3$ (207 mg, 1.5 mmol) in dioxane (25 mL) in a sealed tube was bubbled with $N_2$ for several minutes and then heated under $N_2$ at 130° C. for 15 hours. The solution was then cooled to room temperature and filtered. The filtrate was concentrated under reduced pressure. The residue was purified first by chromatography ($CH_2Cl_2$: MeOH, 100:1), then by preparative-HPLC to give (4-{3-[6-(3-tert-butoxycarbonylamino-1-phenyl-propylamino)-pyridin-2-yl]-imidazo[1,2-a]pyrazin-8-ylamino}-cyclohexyl)-carbamic acid tert-butyl ester. (Yield 250 mg). LC-MS: [M+H]$^+$ 657.

Step B

N-{3-[6-(3-Amino-1-phenyl-propylamino)-pyridin-2-yl]-imidazo[1,2-a]pyrazin-8-yl}-cyclohexane-1,4-diamine; hydrochloride

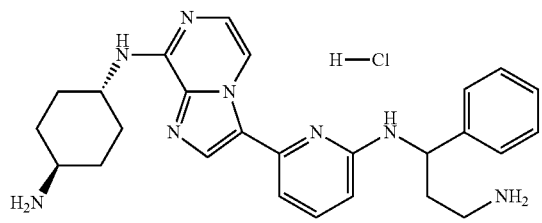 [SMILES: NCCC(Nc1cccc(-c2cnc3c(N[C@H]4CC[C@H](N)CC4)nccn23)n1)c1ccccc1 ; Cl]

The mixture of (4-{3-[6-(3-tert-butoxycarbonylamino-1-phenyl-propylamino)-pyridin-2-yl]-imidazo[1,2-a]pyrazin-8-ylamino}-cyclohexyl)-carbamic acid tert-butyl ester (250 mg, 0.38 mmol) in ethanol (4 mL) and concentrated HCl (4 mL) was stirred at room temperature overnight. The reaction mixture was then concentrated under reduced pressure. The residue was purified by preparative-HPLC to give N-{3-[6-(3-amino-1-phenyl-propylamino)-pyridin-2-yl]-imidazo[1,2-a]pyrazin-8-yl}-cyclohexane-1,4-diamine; hydrochloride. (Yield 18 mg).

$^1$H NMR (300 MHz, $CD_3OD$): δ 8.20 (brs, 1H), 8.13 (s, 1H), 7.74-7.70 (m, 1H), 7.50-7.37 (m, 4H), 7.32-7.30 (m, 1H), 7.17-7.07 (m, 2H), 6.89 (d, 1H, J=8.4 Hz), 5.13-5.10 (m, 1H), 4.05 (brs, 1H), 3.22-3.17 (m, 3H), 2.26-2.24 (m, 6H), 1.73 (brs, 4H). LC-MS: [M+H]$^+$ 457.

Example 82

N-{3-[6-(3-Chloro-benzylamino)-pyridin-2-yl]-imidazo[1,2-a]pyrazin-8-yl}-cyclohexane-1,4-diamine; hydrochloride 484.43

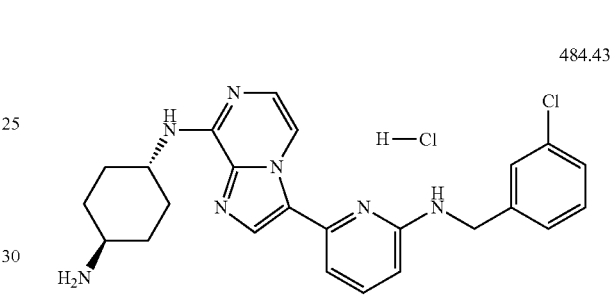

Step A (4-{3-[6-(3-Chloro-benzylamino)-pyridin-2-yl]-imidazo[1,2-a]pyrazin-8-ylamino}-cyclohexyl)-carbamic acid tert-butyl ester

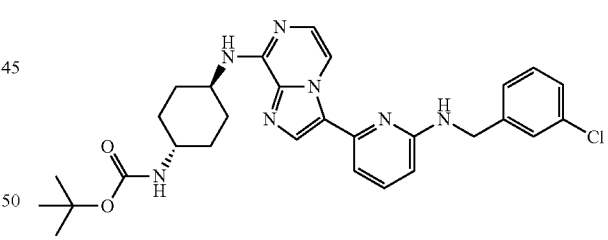

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.487 g, 1.0 mmol), 3-chlorobenzylamine (0.283 g, 2.0 mmol), $Pd_2(dba)_3$ (60 mg), Davephos (80 mg), NaOtBu (200 mg, 0.2 mmol) in dioxane (25 mL) in a sealed tube was bubbled with $N_2$ for several minutes and then heated under $N_2$ at 110° C. for 15 hours. The solution was then cooled to room temperature and filtered. The filtrate was concentrated under reduced pressure. The obtained crude product was purified by preparative-HPLC to give (4-{3-[6-(3-chloro-benzylamino)-pyridin-2-yl]-imidazo[1,2-a]pyrazin-8-ylamino}-cyclohexyl)-carbamic acid tert-butyl ester. (Yield 430 mg). LC-MS: [M+H]$^+$ 548.

Step B

N-{3-[6-(3-Chloro-benzylamino)-pyridin-2-yl]-imidazo[1,2-a]pyrazin-8-yl}-cyclohexane-1,4-diamine; hydrochloride

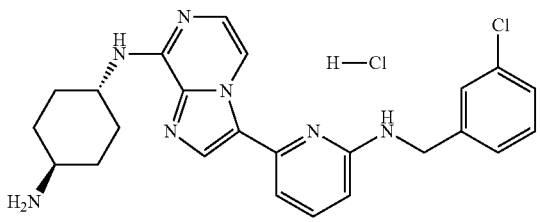 [SMILES: N[C@H]1CC[C@H](Nc2nccn3c(-c4cccc(NCc5cccc(Cl)c5)n4)cnc23)CC1 ; Cl]

The mixture of (4-{3-[6-(3-chloro-benzylamino)-pyridin-2-yl]-imidazo[1,2-a]pyrazin-8-ylamino}-cyclohexyl)-carbamic acid tert-butyl ester (430 mg, 0.78 mmol) in ethanol (4 mL) and concentrated HCl (4 mL) was stirred at room temperature overnight. The reaction mixture was then concentrated under reduced pressure. The obtained crude product was purified by preparative-HPLC to give N-{3-[6-(3-chloro-benzylamino)-pyridin-2-yl]-imidazo[1,2-a]pyrazin-8-yl}-cyclohexane-1,4-diamine; hydrochloride. (Yield 100 mg). $^1$H NMR (300 MHz, CD$_3$OD): δ 8.16-8.13 (m, 2H), 7.91 (t, 1H, J=8.1 Hz), 7.46 (s, 1H), 7.38-7.31 (m, 3H), 7.22-7.17 (m, 2H), 7.04 (d, 1H, J=8.7 Hz), 4.69 (s, 2H), 4.06 (s, 1H), 3.23 (brs, 1H), 2.21 (brs, 4H), 1.76-1.70 (m, 4H). LC-MS: [M+H]$^+$ 448.

Example 83

N-{3-[2-(2-Chloro-benzylamino)-pyrimidin-4-yl]-imidazo[1,2-a]pyrazin-8-yl}-cyclohexane-1,4-diamine; hydrochloride 485.42

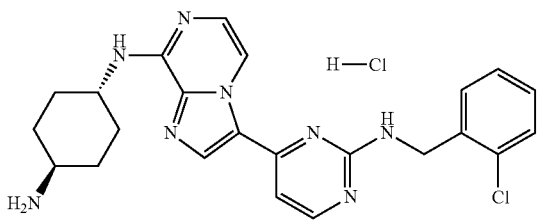

Step A (4-{3-[2-(2-Chloro-benzylamino)-pyrimidin-4-yl]-imidazo[1,2-a]pyrazin-8-ylamino}-cyclohexyl)-carbamic acid tert-butyl ester

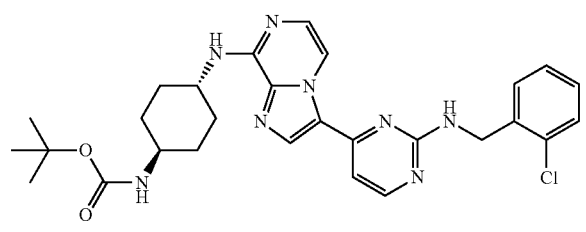 [SMILES: CC(C)(C)OC(=O)N[C@H]1CC[C@H](Nc2nccn3c(-c4ccnc(NCc5ccccc5Cl)n4)cnc23)CC1]

The mixture of {4-[3-(2-methanesulfinyl-pyrimidin-4-yl)-imidazo[1,2-a]pyrazin-8-ylamino]-cyclohexyl}-carbamic acid tert-butyl ester (from Example 48 supra) (100 mg, 0.21 mmol) and 2-chlorobenzylamine (120 mg, 0.84 mmol) was heated at 140° C. with stirring for 2 hours. The oil was purified by chromatography (silica gel, 10 g, 200-300 mesh, eluting with dichloromethane:methanol, 50:1 to 30:1) to afford crude (4-{3-[2-(2-chloro-benzylamino)-pyrimidin-4-yl]-imidazo[1,2-a]pyrazin-8-ylamino}-cyclohexyl)-carbamic acid tert-butyl ester. (Yield 60 mg).

Step B

N-{3-[2-(2-Chloro-benzylamino)-pyrimidin-4-yl]-imidazo[1,2-a]pyrazin-8-yl}-cyclohexane-1,4-diamine; hydrochloride

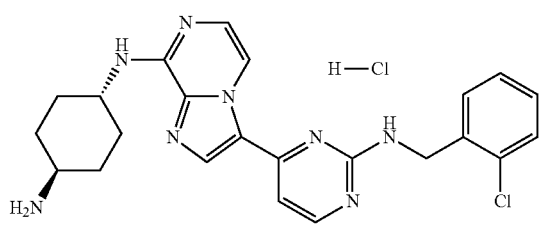 [SMILES: N[C@H]1CC[C@H](Nc2nccn3c(-c4ccnc(NCc5ccccc5Cl)n4)cnc23)CC1 ; Cl]

To a solution of crude (4-{3-[2-(2-chloro-benzylamino)-pyrimidin-4-yl]-imidazo[1,2-a]pyrazin-8-ylamino}-cyclohexyl)-carbamic acid tert-butyl ester (60 mg, 0.11 mmol) in ethanol (5 mL) was added concentrated hydrochloric acid (5 mL) slowly. The reaction mixture was stirred at room temperature for 15 hours. The solvent was removed under reduced pressure and then the solid was purified by prep-HPLC. Several drops of concentrated HCl were added to the fractions with product. After sonicating for several minutes, solution was concentrated under reduced pressure to afford N-{3-[2-(2-chloro-benzylamino)-pyrimidin-4-yl]-imidazo[1,2-a]pyrazin-8-yl}-cyclohexane-1,4-diamine; hydrochloride. (Yield 23 mg, 24.2%).

$^1$H NMR (300 MHz, CD$_3$OD): δ 8.70 (s, 1H), 8.44 (brs, 2H), 7.60-7.49 (m, 3H), 7.35 (brs, 2H), 7.15 (s, 1H), 4.84 (s, 2H), 4.06 (brs, 1H), 3.23 (s, 1H), 2.25-2.19 (m, 4H), 1.78-1.68 (m, 4H). LC-MS: [M+H]$^+$ 449.

Example 84

N-(3-{6-[(Thiophen-3-ylmethyl)-amino]-pyridin-2-yl}-imidazo[1,2-a]pyrazin-8-yl)-cyclohexane-1,4-diamine; hydrochloride 456.02

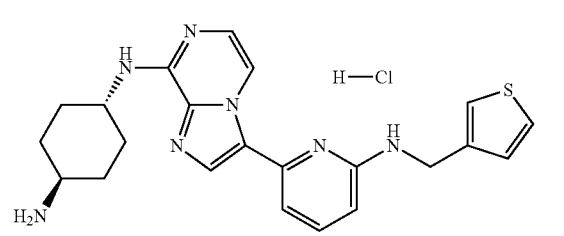

Step A

[4-(3-{6-[(Thiophen-3-ylmethyl)-amino]-pyridin-2-yl}-imidazo[1,2-a]pyrazin-8-ylamino)-cyclohexyl]-carbamic acid tert-butyl ester

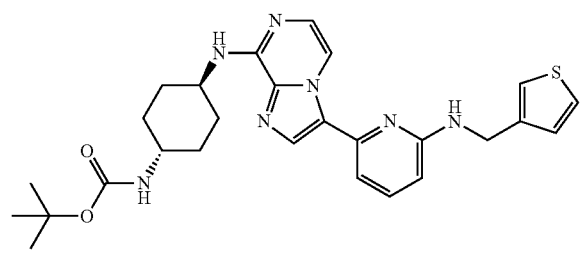 [SMILES: CC(C)(C)OC(=O)N[C@H]1CC[C@H](Nc2nccn3c(-c4cccc(NCc5ccsc5)n4)cnc23)CC1]

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.244 g, 0.5 mmol), compound thiophen-3-yl-methylamine (0.113 g, 1.0 mmol), Pd₂(dba)₃ (30 mg), Davephos (40 mg), NaOtBu (100 mg, 0.1 mmol) in dioxane (12 mL) in a sealed tube was bubbled with N₂ for several minutes and then heated under N₂ at 110° C. for 16 hours. The solution was then cooled to room temperature and filtered. The filtrate was concentrated under reduced pressure. The residue was purified by chromatography (CH₂Cl₂:MeOH, 100:1) to give [4-(3-{6-[(thiophen-3-ylmethyl)-amino]-pyridin-2-yl}-imidazo[1,2-a]pyrazin-8-ylamino)-cyclohexyl]-carbamic acid tert-butyl ester. (Yield 70 mg, 27%).

Step B

N-(3-{6-[(Thiophen-3-ylmethyl)-amino]-pyridin-2-yl}-imidazo[1,2-a]pyrazin-8-yl)-cyclohexane-1,4-diamine; hydrochloride

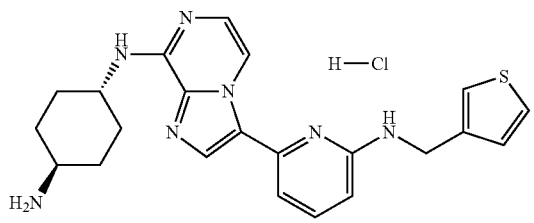 [SMILES: N[C@H]1CC[C@H](Nc2nccn3c(-c4cccc(NCc5ccsc5)n4)cnc23)CC1 ; Cl]

The mixture of [4-(3-{6-[(thiophen-3-ylmethyl)-amino]-pyridin-2-yl}-imidazo[1,2-a]pyrazin-8-ylamino)-cyclohexyl]-carbamic acid tert-butyl ester (70 mg, 0.135 mmol) in ethanol (4 mL) and concentrated HCl (4 mL) was stirred at room temperature for 15 h. The reaction mixture was then concentrated under reduced pressure to give N-(3-{6-[(thiophen-3-ylmethyl)-amino]-pyridin-2-yl}-imidazo[1,2-a]pyrazin-8-yl)-cyclohexane-1,4-diamine; hydrochloride. (Yield 83 mg). ¹HNMR (300 MHz, CD₃OD): δ 8.06 (s, 1H), 7.94 (d, 1H, J=5.4 Hz), 7.87 (t, 1H, J=8.7 Hz), 7.39-7.34 (m, 2H), 7.16-7.03 (m, 4H), 4.62 (s, 2H), 3.98 (brs, 1H), 3.14 (brs, 1H), 2.14-2.09 (brs, 4H), 1.70-1.60 (m, 4H). LC-MS: [M+H]⁺ 420.

Example 85

N-{3-[6-(2-Chloro-benzylamino)-pyridin-2-yl]-imidazo[1,2-a]pyrazin-8-yl}-cyclohexane-1,4-diamine; hydrochloride 484.43

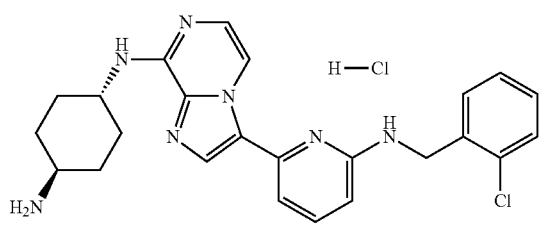 [SMILES: N[C@H]1CC[C@H](Nc2nccn3c(-c4cccc(NCc5ccccc5Cl)n4)cnc23)CC1 ; Cl]

Step A (4-{3-[6-(2-Chloro-benzylamino)-pyridin-2-yl]-imidazo[1,2-a]pyrazin-8-ylamino}-cyclohexyl)-carbamic acid tert-butyl ester A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.244 g, 0.5 mmol), 2-chloro-benzylamine (0.143 g, 1.0 mmol), Pd₂(dba)₃ (30 mg), Davephos (40 mg), NaOtBu (100 mg, 0.1 mmol) in dioxane (12 mL) in a sealed tube was bubbled with N₂ for several minutes and then heated under N₂ at 110° C. overnight. The solution was then cooled to room temperature and filtered. The filtrate was concentrated under reduced pressure. The residue was purified by chromatography (CH₂Cl₂:MeOH, 100:1) to give (4-{3-[6-(2-chloro-benzylamino)-pyridin-2-yl]-imidazo[1,2-a]pyrazin-8-ylamino}-cyclohexyl)-carbamic acid tert-butyl ester. (Yield 227 mg, 83%).

Step B

N-{3-[6-(2-Chloro-benzylamino)-pyridin-2-yl]-imidazo[1,2-a]pyrazin-8-yl}-cyclohexane-1,4-diamine; hydrochloride The mixture of (4-{3-[6-(2-chloro-benzylamino)-pyridin-2-yl]-imidazo[1,2-a]pyrazin-8-ylamino}-cyclohexyl)-carbamic acid tert-butyl ester (227 mg, 0.41 mmol) in ethanol (4 mL) and concentrated HCl (4 mL) was stirred at room temperature overnight. The reaction mixture was then concentrated under reduced pressure. The residue was purified by preparative-HPLC to give N-{3-[6-(2-chloro-benzylamino)-pyridin-2-yl]-imidazo[1,2-a]pyrazin-8-yl}-cyclohexane-1,4-diamine; hydrochloride. (Yield 60 mg). ¹HNMR (300 MHz, CD₃OD): δ 8.25 (d, 1H, J=5.7 Hz), 8.19 (s, 1H), 7.88 (t, 1H, J=8.7 Hz), 7.53-7.50 (m, 2H), 7.35-7.22 (m, 3H), 7.10 (d, 1H, J=5.7 Hz), 7.02 (d, 1H, J=8.7 Hz), 4.77 (s, 2H), 4.05 (brs, 1H), 3.32 (brs, 1H), 2.23 (brs, 4H), 1.81-1.74 (m, 4H). LC-MS: [M+H]⁺ 448.

Example 86

N-{3-[6-(4-Chloro-benzylamino)-pyridin-2-yl]-imidazo[1,2-a]pyrazin-8-yl}-cyclohexane-1,4-diamine; hydrochloride 484.43

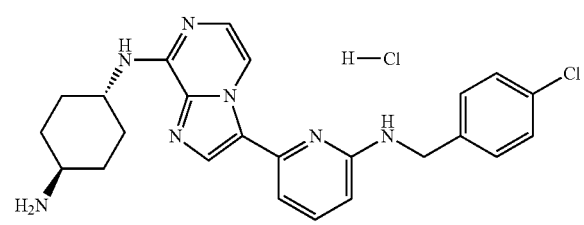

Step A (4-{3-[6-(4-Chloro-benzylamino)-pyridin-2-yl]-imidazo[1,2-a]pyrazin-8-ylamino}-cyclohexyl)-carbamic acid tert-butyl ester

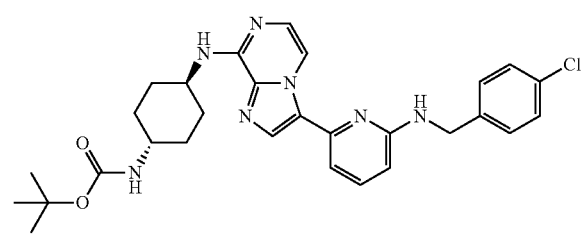 [SMILES: CC(C)(C)OC(=O)N[C@H]1CC[C@H](Nc2nccn3c(-c4cccc(NCc5ccc(Cl)cc5)n4)cnc23)CC1]

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.244 g, 0.5 mmol), 4-chlorobenzylamine (0.143 g, 1.0 mmol), Pd₂(dba)₃ (30 mg), Davephos (40 mg), NaOtBu (100 mg, 0.1 mmol) in dioxane (12 mL) in a sealed tube was bubbled with N₂ for several minutes and then heated under N₂ at 110° C. for 14 hours. The solution was then cooled to room temperature and filtered. The filtrate was concentrated under reduced pressure. The residue was purified by chromatography (CH₂Cl₂:MeOH, 100:1) to give (4-{3-[6-(4-chloro-benzylamino)-pyridin-2-yl]-imidazo[1,2-a]pyrazin-8-ylamino}-cyclohexyl)-carbamic acid tert-butyl ester. (Yield 214 mg, 78%).

Step B

N-{3-[6-(4-Chloro-benzylamino)-pyridin-2-yl]-imidazo[1,2-a]pyrazin-8-yl}-cyclohexane-1,4-diamine; hydrochloride

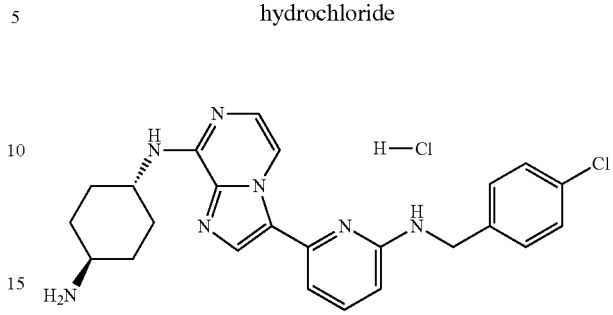

A mixture of (4-{3-[6-(4-chloro-benzylamino)-pyridin-2-yl]-imidazo[1,2-a]pyrazin-8-ylamino}-cyclohexyl)-carbamic acid tert-butyl ester (214 mg, 0.39 mmol) in ethanol (4 mL) and concentrated HCl (4 mL) was stirred at room temperature overnight. The reaction mixture was then concentrated under reduced pressure. The residue was purified by preparative-HPLC to give N-{3-[6-(4-chloro-benzylamino)-pyridin-2-yl]-imidazo[1,2-a]pyrazin-8-yl}-cyclohexane-1,4-diamine; hydrochloride. (Yield 80 mg). ¹HNMR (300 MHz, CD₃OD): δ 8.22 (d, 1H, J=5.7 Hz), 8.19 (s, 1H), 7.89 (t, 1H, J=8.7 Hz), 7.46-7.39 (m, 4H), 7.23 (d, 1H, J=6.9 Hz), 7.17 (d, 1H, J=5.7 Hz), 7.02 (d, 1H, J=8.7 Hz), 4.70 (s, 2H), 4.04 (brs, 1H), 3.25 (brs, 1H), 2.23 (brs, 4H), 1.81-1.71 (m, 4H). LC-MS: [M+H]⁺ 448.

Example 87

N-(3-{6-[(Thiophen-2-ylmethyl)-amino]-pyridin-2-yl}-imidazo[1,2-a]pyrazin-8-yl)-cyclohexane-1,4-diamine; hydrochloride

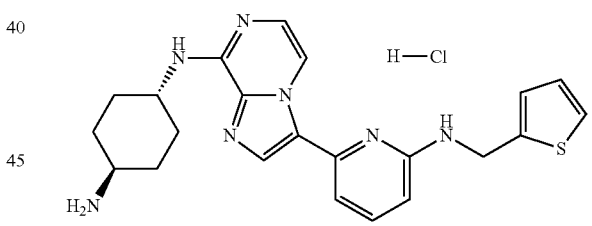

Step A

[4-(3-{6-[(Thiophen-2-ylmethyl)-amino]-pyridin-2-yl}-imidazo[1,2-a]pyrazin-8-ylamino)-cyclohexyl]-carbamic acid tert-butyl ester

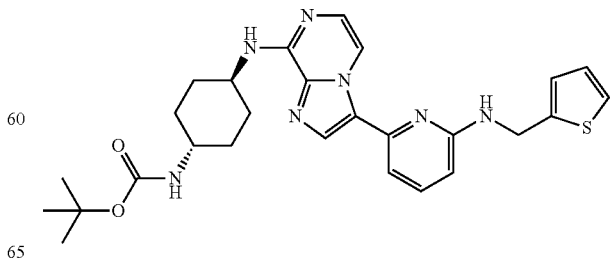

A mixture of {4-[3-(6-bromo-pyridin-2-yl)-imidazo[1,2-a]pyrazin-8-ylamino]-cyclohexyl}-carbamic acid tert-butyl ester (from Example 40 supra) (0.244 g, 0.5 mmol), thiophen-2-yl-methylamine (0.113 g, 1.0 mmol), Pd$_2$(dba)$_3$ (30 mg), Davephos (40 mg), NaOtBu (100 mg, 0.1 mmol) in dioxane (15 mL) in a sealed tube was bubbled with N$_2$ for several minutes and then heated under N$_2$ at 110° C. for 16 hour. The solution was then cooled to room temperature and filtered. The filtrate was concentrated under reduced pressure. The residue was purified first by chromatography (CH$_2$Cl$_2$: MeOH, 100:1), then by preparative-HPLC to give [4-(3-{6-[(thiophen-2-ylmethyl)-amino]-pyridin-2-yl}-imidazo[1,2-a]pyrazin-8-ylamino)-cyclohexyl]-carbamic acid tert-butyl ester. (Yield 100 mg, 38%). LC-MS: [M+H]$^+$ 520.

Step B

N-(3-{6-[(Thiophen-2-ylmethyl)-amino]-pyridin-2-yl}-imidazo[1,2-a]pyrazin-8-yl)-cyclohexane-1,4-diamine; hydrochloride

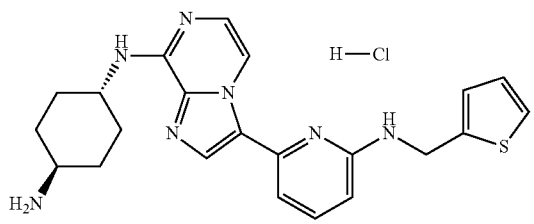 [SMILES: N[C@H]1CC[C@H](Nc2nccn3c(-c4cccc(NCc5cccs5)n4)cnc23)CC1 ; Cl]

The mixture of [4-(3-{6-[(thiophen-2-ylmethyl)-amino]-pyridin-2-yl}-imidazo[1,2-a]pyrazin-8-ylamino)-cyclohexyl]-carbamic acid tert-butyl ester (100 mg, 0.193 mmol) in ethanol (4 mL) and concentrated HCl (4 mL) was stirred at room temperature overnight. The reaction mixture was then concentrated under reduced pressure. The residue was purified by prepara-HPLC to give N-(3-{6-[(thiophen-2-ylmethyl)-amino]-pyridin-2-yl}-imidazo[1,2-a]pyrazin-8-yl)-cyclohexane-1,4-diamine; hydrochloride. (Yield 30 mg). $^1$HNMR (300 MHz, CD$_3$OD): δ 8.59-8.56 (m, 1H), 8.38 (brs, 1H), 7.82 (d, 1H, J=9.0 Hz), 7.42-7.34 (m, 1H), 7.16-7.04 (m, 2H), 6.98-6.85 (m, 2H), 6.43-6.39 (m, 1H), 4.70 (d, 2H, J=5.1 Hz), 3.89-3.85 (m, 1H), 3.23-3.07 (m, 1H), 2.20-2.05 (m, 4H), 1.60-1.37 (m, 4H). LC-MS: [M+H]$^+$ 420.

Example 88

{3-[2-(2-Chloro-benzylamino)-pyrimidin-4-yl]-imidazo[1,2-a]pyrazin-8-yl}-(2-morpholin-4-yl-ethyl)-amine; hydrochloride

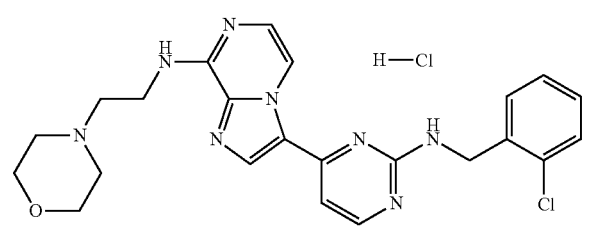

501.42

A mixture of [3-(2-methanesulfonyl-pyrimidin-4-yl)-imidazo[1,2-a]pyrazin-8-yl]-(2-morpholin-4-yl-ethyl)-amine (from Example 50 supra) (200 mg, 0.50 mmol) and 2-chlorobenzylamine (281 mg, 1.99 mmol) was heated at 140° C. with stirring for 2 hours. The oil was purified by chromatography (silica gel, 10 g, 200-300 mesh, eluting with dichloromethane:methanol 50:1 to 20:1) to afford the crude product (110 mg). Then the crude product was purified by prep-HPLC. Several drops of concentrated HCl were added to the fractions with product. After sonicating for several minutes, solution was concentrated under reduced pressure to afford {3-[2-(2-chloro-benzylamino)-pyrimidin-4-yl]-imidazo[1,2-a]pyrazin-8-yl}-(2-morpholin-4-yl-ethyl)-amine; hydrochloride. (Yield 58 mg, 25.1%). $^1$H NMR (300 MHz, CD$_3$OD): δ 8.72 (s, 1H), 8.51 (s, 1H), 8.35 (s, 1H), 7.59 (d, 1H, J=6.9 Hz), 7.46-7.28 (m, 5H), 4.75 (brs, 2H), 4.17 (brs, 2H), 3.93 (brs, 4H), 3.59-3.28 (m, 5H). LC-MS: [M+H]$^+$ 466.

Example 89

{3-[2-(3-Chloro-benzylamino)-pyrimidin-4-yl]-imidazo[1,2-a]pyrazin-8-yl}-(2-morpholin-4-yl-ethyl)-amine; hydrochloride

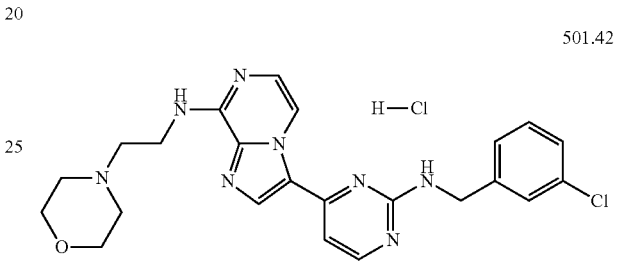

501.42

The mixture of [3-(2-methanesulfonyl-pyrimidin-4-yl)-imidazo[1,2-a]pyrazin-8-yl]-(2-morpholin-4-yl-ethyl)-amine (from Example 50 supra) (200 mg, 0.50 mmol) and 3-chlorobenzylamine (281 mg, 1.99 mmol) was heated at 140° C. with stirring for 2 hours. The oil was purified by chromatography (silica gel, 10 g, 200-300 mesh, eluting with dichloromethane:methanol, 50:1~20:1) to afford the crude product (125 mg). Then the crude product was purified by prep-HPLC. Several drops of concentrated HCl were added to the fractions with product. After sonicating for several minutes, solution was concentrated under reduced pressure to afford {3-[2-(3-chloro-benzylamino)-pyrimidin-4-yl]-imidazo[1,2-a]pyrazin-8-yl}-(2-morpholin-4-yl-ethyl)-amine; hydrochloride. (Yield 60 mg, 26.0%). $^1$H NMR (300 MHz, CD$_3$OD): δ 8.71 (s, 1H), 8.42 (s, 1H), 8.38 (s, 1H), 7.59 (d, 1H, J=6.6 Hz), 7.49-7.28 (m, 5H), 4.87 (brs, 2H), 4.16 (brs, 2H), 3.93 (brs, 4H), 3.58-3.28 (m, 5H). LC-MS: [M+H]$^+$ 466.

Example 90

1-(3-Chloro-phenyl)-N-1-{6-[8-(2-morpholin-4-yl-ethylamino)-imidazo[1,2-a]pyrazin-3-yl]-pyridin-2-yl}-propane-1,3-diamine hydrochloride

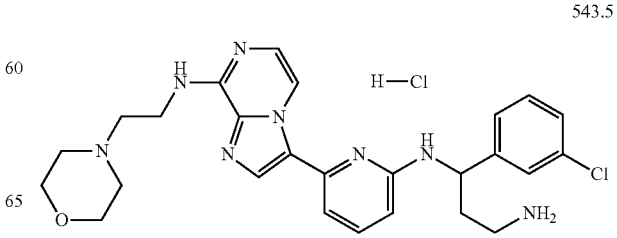

543.5

Step A (3-(3-Chloro-phenyl)-3-{6-[8-(2-morpholin-4-yl-ethylamino)-imidazo[1,2-a]pyrazin-3-yl]-pyridin-2-ylamino}-propyl)-carbamic acid tert-butyl ester

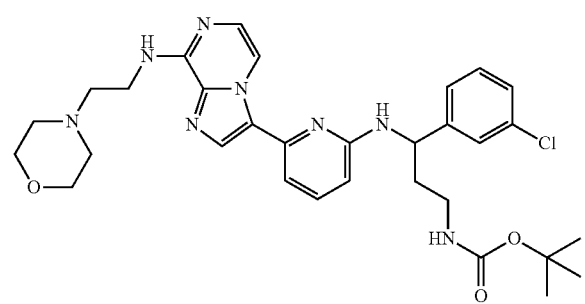 [SMILES: CC(C)(C)OC(=O)NCCC(Nc1cccc(-c2cnc3c(NCCN4CCOCC4)nccn23)n1)c1cccc(Cl)c1]

A mixture of [3-(6-bromo-pyridin-2-yl)-imidazo[1,2-a]pyrazin-8-yl]-(2-morpholin-4-yl-ethyl)-amine (from Example 41 supra) (0.403 g, 1.0 mmol), [3-amino-3-(3-chloro-phenyl)-propyl]-carbamic acid tert-butyl ester (from Example 62 supra) (0.427 g, 1.5 mmol), $Pd_2(dba)_3$ (60 mg), Davephos (80 mg), $K_2CO_3$ (207 mg, 1.5 mmol) in dioxane (25 mL) in a sealed tube was bubbled with $N_2$ for several minutes and then heated under $N_2$ at 130° C. overnight. The solution was then cooled to room temperature and filtered. The filtrate was concentrated under reduced pressure. The residue was purified by preparative-HPLC to give (3-(3-chloro-phenyl)-3-{6-[8-(2-morpholin-4-yl-ethylamino)-imidazo[1,2-a]pyrazin-3-yl]-pyridin-2-ylamino}-propyl)-carbamic acid tert-butyl ester. (Yield 50 mg). LC-MS: 607 $[M+H]^+$ 607.

Step B 1-(3-Chloro-phenyl)-N-1-{6-[8-(2-morpholin-4-yl-ethylamino)-imidazo[1,2-a]pyrazin-3-yl]-pyridin-2-yl}-propane-1,3-diamine hydrochloride

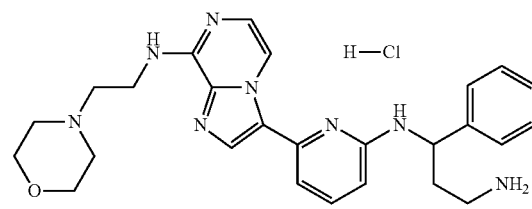

The mixture of (3-(3-chloro-phenyl)-3-{6-[8-(2-morpholin-4-yl-ethylamino)-imidazo[1,2-a]pyrazin-3-yl]-pyridin-2-ylamino}-propyl)-carbamic acid tert-butyl ester (50 mg, 0.08 mmol) in ethanol (4 mL) and concentrated HCl (4 mL) was stirred at room temperature overnight. The reaction mixture was then concentrated under reduced pressure to give 1-(3-chloro-phenyl)-N-1-{6-[8-(2-morpholin-4-yl-ethylamino)-imidazo[1,2-a]pyrazin-3-yl]-pyridin-2-yl}-propane-1,3-diamine hydrochloride. (Yield 50 mg). $^1$HNMR (300 MHz, $CD_3OD$): δ 8.51 (s, 1H), 8.24 (s, 1H), 7.66-7.63 (m, 1H), 7.54 (s, 1H), 7.45-7.19 (m, 5H), 6.84-6.80 (m, 1H), 5.11(brs, 1H), 4.24 (brs, 2H), 4.00 (brs, 4H), 3.65-3.49 (m, 6H), 3.24-3.10 (m, 2H), 2.23 (brs, 2H). LC-MS: 508 $[M+H]^+$ 508.

Example 91

1-(3-Chloro-phenyl)-N-1-{6-[8-(2-morpholin-4-yl-ethylamino)-imidazo[1,2-a]pyrazin-3-yl]-pyridin-2-yl}-ethane-1,2-diamine hydrochloride 529.47

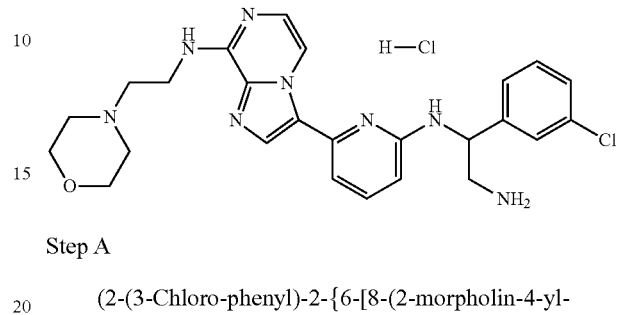

Step A (2-(3-Chloro-phenyl)-2-{6-[8-(2-morpholin-4-yl-ethylamino)-imidazo[1,2-a]pyrazin-3-yl]-pyridin-2-ylamino}-ethyl)-carbamic acid tert-butyl ester

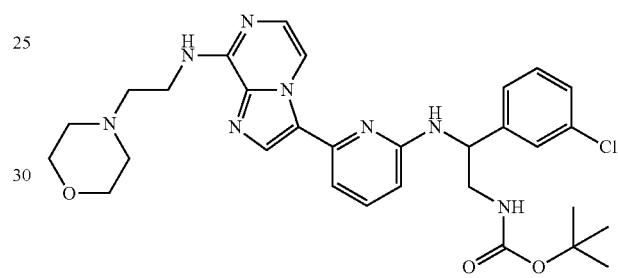

A mixture of [3-(6-bromo-pyridin-2-yl)-imidazo[1,2-a]pyrazin-8-yl]-(2-morpholin-4-yl-ethyl)-amine (from Example 41 supra) (0.403 g, 1.0 mmol), [2-amino-2-(3-chloro-phenyl)-ethyl]-carbamic acid tert-butyl ester (from Example 78 supra) (0.406 g, 1.5 mmol), $Pd_2(dba)_3$(60 mg), Davephos (80 mg), $K_2CO_3$ (207 mg, 1.5 mmol) in dioxane (25 mL) in a sealed tube was bubbled with $N_2$ for several minutes and then heated under $N_2$ at 130° C. overnight. The solution was then cooled to room temperature and filtered. The filtrate was concentrated under reduced pressure. The obtained residue was purified by chromatography ($CH_2Cl_2$: MeOH, 50:1 to 20:1) to give crude (2-(3-chloro-phenyl)-2-{6-[8-(2-morpholin-4-yl-ethylamino)-imidazo[1,2-a]pyrazin-3-yl]-pyridin-2-ylamino}-ethyl)-carbamic acid tert-butyl ester. (Yield 210 mg). LC-MS: $[M+H]^+$ 593.

Step B 1-(3-Chloro-phenyl)-N-1-{6-[8-(2-morpholin-4-yl-ethylamino)-imidazo[1,2-a]pyrazin-3-yl]-pyridin-2-yl}-ethane-1,2-diamine hydrochloride

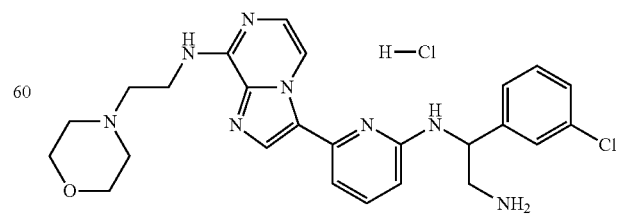

The mixture of crude (2-(3-chloro-phenyl)-2-{6-[8-(2-morpholin-4-yl-ethylamino)-imidazo[1,2-a]pyrazin-3-yl]- pyridin-2-ylamino}-ethyl)-carbamic acid tert-butyl ester (210 mg, 0.35 mmol) in ethanol (4 mL) and concentrated HCl (4 mL) was stirred at room temperature overnight. The reaction mixture was then concentrated under reduced pressure to give 1-(3-chloro-phenyl)-N-1-{6-[8-(2-morpholin-4-yl-ethylamino)-imidazo[1,2-a]pyrazin-3-yl]-pyridin-2-yl}-ethane-1,2-diamine hydrochloride. (Yield 150 mg). $^1$H NMR (300 MHz, CD$_3$OD): δ 8.58 (s, 1H), 8.27 (s, 1H), 7.68-7.63 (m, 2H), 7.51-7.39 (m, 3H), 7.31-7.27 (m, 2H), 6.73 (d, 1H, J=8.4 Hz), 5.48-5.41 (m, 1H), 3.99-3.92 (m, 6H), 3.53-3.24 (m, 8H). LC-MS: [M+H]$^+$ 493.

The pharmacological properties of the compounds of this invention may be confirmed by a number of pharmacological assays. The exemplified antiproliferative activity assays which follow have been carried out with compounds according to the invention.

Example 92

FLT3 Kinase Assay

FLT3 kinase assay was obtained from Claiper Life Sciences (Catalog #200-0423). The assay was carried out with human recombinant FLT3 (0.287 nM), fluoresce in labeled peptide substrate (with a peptide sequence of EAIYAAP-FAKKK, 1.5 µM) and test compounds (in serial dilution) using 384-well plates, quantified by Caliper technology. Kinase reaction was performed in 100 mM HEPES, pH 7.5, 4% DMSO, 0.003% Brij-35, 0.004% tween, 10 mM MgCl$_2$, and 100 µM ATP (for IC$_{50}$ determination), incubated at 28° C. for 90 minutes. After incubation, the reaction product was analyzed by electrophoretic mobility shift run on Caliper by manufacturer's protocol.

IC$_{50}$ is the amount of test compound that inhibits 50% of the activity of FLT3 in this assay. In some cases where the IC$_{50}$ values were not determined, then the % inhibition at 10 µM test compound concentration may be reported instead. The results of this assay for sample compounds of the invention are provided in Table I below.

Example 93

Cell Glo Viability Assay (Luminscence)

Molm13 cells, a human acute monocytic leukemia cell line, and MV4-11 cells, a human leukemia cell line known to express mutated FLT3 cells (both from ATCC) were seeded separately at 2000 cells per well in 90 µL of RPMI1640 medium supplemented with 10% FBS in 96-well black-walled plates (BD Falcon). Test compounds were diluted at ten times of assay concentrations, 10 µL was added into duplicate wells. Plates were incubated at 37° C. with 5% CO$_2$ for 5 days. Cell viability was assayed by CellTiter-Glo® Luminescent Cell Viability Assay (Promega) following manufacturer's protocol.

The results of this assay, given as EC$_{50}$ values, indicate the concentration of test compound that inhibits tumor cell proliferation by 50%. The results of this assay for sample compounds of the invention are also provided in Table I below.

TABLE I

| | Kinase enzyme and cellular activity | | |
|---|---|---|---|
| Example | Enzyme IC$_{50}$ (µM) FLT3 | Cellular EC$_{50}$ (µM) Molm13 | Cellular EC$_{50}$ (µM) MV4-11 |
| 12 | NT | NT | NT |
| 13 | NT | NT | NT |
| 14 | 0.045 | NT | NT |
| 15 | NT | NT | NT |
| 16 | NT | NT | NT |
| 17 | NT | NT | NT |
| 18 | NT | NT | NT |
| 19 | NT | NT | NT |
| 20 | <0.005 | 0.052 | 0.041 |
| 21 | 0.122 | NT | NT |
| 22 | NT | NT | NT |
| 23 | 1.29 | NT | NT |
| 24 | NT | NT | NT |
| 25 | NT | NT | NT |
| 26 | 0.105 | 2.557 | 1.118 |
| 27 | NT | NT | NT |
| 28 | NT | NT | NT |
| 29 | 0.589 | NT | NT |
| 30 | 0.166 | 2.188 | 0.745 |
| 31 | 0.218 | NT | NT |
| 32 | 0.102 | NT | NT |
| 33 | NT | NT | NT |
| 34 | NT | NT | NT |
| 35 | 0.025 | NT | NT |
| 52 | 0.539 | NT | NT |
| 54 | 4.93 | NT | NT |
| 55 | 0.54 | NT | NT |
| 56 | 7.155 | NT | NT |
| 57 | 1.281 | NT | NT |
| 58 | 1.355 | NT | NT |
| 59 | 29.2% | NT | NT |
| 60 | 5.78 | NT | NT |
| 61 | 1.096 | NT | NT |
| 63 | 1.83 | NT | NT |
| 64 | 33.5% | NT | NT |
| 65 | 1.33 | NT | NT |
| 66 | 0.868 | NT | NT |
| 67 | <0.005 | 0.049 | 0.017 |
| 68 | <0.005 | 0.061 | 0.052 |
| 70 | 0.051 | NT | NT |
| 71 | 13.2% | NT | NT |
| 72 | 0.008 | 0.171 | 0.124 |
| 73 | 0.006 | 0.077 | 0.04 |
| 75 | 0.082 | 1.693 | 0.878 |
| 76 | <0.005 | 0.301 | 0.232 |
| 77 | <0.005 | 0.08 | 0.015 |
| 79 | 0.321 | 1.966 | 1.012 |
| 80 | <0.005 | 0.041 | <0.014 |
| 81 | 0.003 | 0.255 | 0.288 |
| 82 | 0.01 | 0.119 | 0.049 |
| 83 | <0.005 | 0.021 | 0.016 |
| 84 | <0.005 | 0.056 | 0.068 |
| 85 | <0.005 | <0.014 | <0.014 |
| 86 | 0.064 | 0.353 | 0.385 |
| 87 | 0.006 | 0.074 | 0.07 |
| 88 | 0.006 | 0.037 | 0.055 |
| 89 | 0.019 | 0.075 | 0.06 |
| 90 | <0.005 | 0.034 | <0.014 |
| 91 | <0.005 | <0.014 | <0.014 |

NT: not tested

What is claimed:
1. A compound of formula I

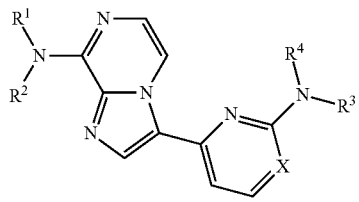

wherein
X is selected from CH or N,
R$^1$ and R$^2$ are independently selected from the group consisting of
(a) H,
(b) C$_{1-4}$ alkyl,
(c) C$_{1-4}$ alkyl substituted with up to 3 groups selected from cycloalkyl, heterocycle, OR$^5$, NR$^5$R$^6$, SO$_2$R$^7$ or CN,
(d) heterocycle,
(e) heterocycle substituted with up to three groups selected from C$_{1-4}$ alkyl, OR$^8$, NR$^8$R$^9$ or CN,
(f) cycloalkyl, and
(g) cycloalkyl substituted with up to three groups selected from C$_{1-4}$ alkyl, OR$^8$, NR$^8$R$^9$ or CN; or
alternatively, NR$^1$R$^2$ together can be a heterocycle that optionally may be substituted with C$_{1-4}$ alkyl;
R$^3$ is selected from the group consisting of
(a) C$_{1-6}$ alkyl
(b) C$_{1-6}$ alkyl substituted with up to 3 groups selected from
aryl,
aryl substituted with Cl, F, CH$_3$, or CF$_3$,
heteroaryl,
cycloalkyl,
heterocycle,
OH,
OCH$_3$,
NR$^8$R$^9$, and
CN;
(c) aryl,
(d) aryl substituted with Cl, F, C$_{1-4}$ alkyl or CF$_3$,
(e) heteroaryl,
(f) cycloalkyl optionally substituted with OR$^5$, and
(g) heterocycle;
R$^4$, R$^8$ and R$^9$ are independently selected from the group consisting of
(a) H, and
(b) C$_{1-4}$ alkyl; or
alternatively, NR$^3$R$^4$ together can be a heterocycle that optionally is substituted with C$_{1-4}$ alkyl;
R$^5$ and R$^6$ are independently selected from the group consisting of
(a) H, and
(b) C$_{1-4}$ alkyl; and
R$^7$ is selected from the group
(a) C$_{1-4}$ alkyl, and
(b) cycloalkyl;
or a pharmaceutically acceptable salt thereof.
2. The compound of claim 1 wherein either one of X is N, or a pharmaceutically acceptable salt thereof.
3. The compound of claim 1 wherein both X is CH, or a pharmaceutically acceptable salt thereof.
4. The compound of claim 1, wherein R$^1$ is C$_{1-4}$ alkyl, or a pharmaceutically acceptable salt thereof.
5. The compound of claim 4 wherein R$^1$ is C$_{1-4}$ alkyl that optionally is substituted with heterocycle, or a pharmaceutically acceptable salt thereof.
6. The compound of claim 4 wherein R$^1$ is C$_{1-4}$ alkyl that optionally is substituted with OH, or a pharmaceutically acceptable salt thereof.
7. The compound of claim 4 wherein R$^1$ is C$_{1-4}$ alkyl that optionally is substituted with SO$_2$R$^7$ and R$^7$ is C$_{1-4}$ alkyl, or a pharmaceutically acceptable salt thereof.
8. The compound of claim 1, wherein R$^1$ is cycolakyl that optionally is substituted with NR$^8$R$^9$, or a pharmaceutically acceptable salt thereof.
9. The compound of claim 8 wherein NR$^8$R$^9$ is NH$_2$, or a pharmaceutically acceptable salt thereof.
10. The compound of claim 1, wherein R$^1$ is a heterocycle, or a pharmaceutically acceptable salt thereof.
11. The compound of claim 10 wherein R$^1$ is piperazine or morpholine, or a pharmaceutically acceptable salt thereof.
12. The compound of claim 1, wherein R$^2$ is H, or a pharmaceutically acceptable salt thereof.
13. The compound of claim 1, wherein R$^2$ is C$_{1-4}$ alkyl, or a pharmaceutically acceptable salt thereof.
14. The compound of claim 1, wherein NR$^1$R$^2$ together are a heterocycle that optionally may be substituted with C$_{1-4}$ alkyl, or a pharmaceutically acceptable salt thereof.
15. The compound of claim 14 wherein NR$^1$R$^2$ is piperazine that optionally is substituted with methyl, or a pharmaceutically acceptable salt thereof.
16. The compound of claim 1, wherein R$^3$ is C$_{1-6}$ alkyl that optionally may be substituted with aryl, heteroaryl, or herterocycle, or a pharmaceutically acceptable salt thereof.
17. The compound of claim 16 wherein R$^3$ is C$_{1-6}$ alkyl that optionally is substituted with up to two groups selected from thiophene and phenyl, or a pharmaceutically acceptable salt thereof.
18. The compound of claim 1, wherein R$^3$ is cycloalkyl that optionally may be substituted with OR$^5$, or a pharmaceutically acceptable salt thereof.
19. The compound of claim 18 wherein R$^3$ is cyclohexane that optionally may be substituted with OH.
20. The compound of claim 1, wherein R$^3$ is aryl, or a pharmaceutically acceptable salt thereof.
21. The compound of claim 20 wherein R$^3$ is phenyl, or a pharmaceutically acceptable salt thereof.
22. The compound of claim 1, wherein R$^4$ is H, or a pharmaceutically acceptable salt thereof.
23. The compound of claim 1, wherein NR$^3$R$^4$ together are a heterocycle that optionally is substituted with C$_{1-4}$ alkyl, or a pharmaceutically acceptable salt thereof.
24. The compound of claim 23 wherein NR$^3$R$^4$ is morpholine or piperazine that optionally may be substituted with methyl, or a pharmaceutically acceptable salt thereof.
25. The compound of claim 1, wherein R$^5$ and R$^6$ are independently H or CH$_3$, or a pharmaceutically acceptable salt thereof.
26. The compound of claim 1, wherein R$^7$, R$^8$ and R$^9$ are independently selected from an C$_{1-4}$ alkyl group, or a pharmaceutically acceptable salt thereof.
27. A compound selected from the group comprising:
Isopropyl-[3-(2-phenylamino-pyrimidin-4-yl)-imidazo[1,2-a]pyrazin-8-yl]-amine;
2-[3-(2-Phenylamino-pyrimidin-4-yl)-imidazo[1,2-a]pyrazin-8-ylamino]-ethanol;

(2-Methanesulfonyl-ethyl)-{3-[2-(tetrahydro-pyran-4-ylamino)-pyrimidin-4-yl]-imidazo[1,2-a]pyrazin-8-yl}-amine;
(2-Methanesulfonyl-ethyl)-[3-(2-morpholin-4-yl-pyrimidin-4-yl)-imidazo[1,2-a]pyrazin-8-yl]-amine;
[3-(2-Isopropylamino-pyrimidin-4-yl)-imidazo[1,2-a]pyrazin-8-yl]-(2-methanesulfonyl-ethyl)-amine;
4-[4-(8-Isopropylamino-imidazo[1,2-a]pyrazin-3-yl)-pyrimidin-2-ylamino]-cyclohexanol;
Isopropyl-{3-[2-(tetrahydro-pyran-4-ylamino)-pyrimidin-4-yl]-imidazo[1,2-a]pyrazin-8-yl}-amine;
Isopropyl-[3-(2-morpholin-4-yl-pyrimidin-4-yl)-imidazo[1,2-a]pyrazin-8-yl]-amine;
Methyl-[3-(2-phenylamino-pyrimidin-4-yl)-imidazo[1,2-a]pyrazin-8-yl]-amine;
Methyl-[3-(2-morpholin-4-yl-pyrimidin-4-yl)-imidazo[1,2-a]pyrazin-8-yl]-amine; and
Piperidin-4-yl-{3-[2-(tetrahydro-pyran-4-ylamino)-pyrimidin-4-yl]-imidazo[1,2-a]pyrazin-8-yl}-amine;
or a pharmaceutically acceptable salt of any of the foregoing compounds.

28. A compound selected from the group comprising:
[3-(2-Morpholin-4-yl-pyrimidin-4-yl)-imidazo[1,2-a]pyrazin-8-yl]-piperidin-4-yl-amine;
[3-(2-Isopropylamino-pyrimidin-4-yl)-imidazo[1,2-a]pyrazin-8-yl]-piperidin-4-yl-amine;
Isopropyl-[3-(2-isopropylamino-pyrimidin-4-yl)-imidazo[1,2-a]pyrazin-8-yl]-amine;
[3-(2-Methylamino-pyrimidin-4-yl)-imidazo[1,2-a]pyrazin-8-yl]-piperidin-4-yl-amine;
4-{4-[8-(2-Methanesulfonyl-ethylamino)-imidazo[1,2-a]pyrazin-3-yl]-pyrimidin-2-ylamino}-cyclohexanol;
2-{3-[2-(Tetrahydro-pyran-4-ylamino)-pyrimidin-4-yl]-imidazo[1,2-a]pyrazin-8-ylamino}-ethanol;
2-[3-(2-Morpholin-4-yl-pyrimidin-4-yl)-imidazo[1,2-a]pyrazin-8-ylamino]-ethanol;
2-[3-(2-Isopropylamino-pyrimidin-4-yl)-imidazo[1,2-a]pyrazin-8-ylamino]-ethanol;
2-[3-(2-Methylamino-pyrimidin-4-yl)-imidazo[1,2-a]pyrazin-8-ylamino]-ethanol;
Isopropyl-[3-(2-methylamino-pyrimidin-4-yl)-imidazo[1,2-a]pyrazin-8-yl]-amine; and
(2-Methanesulfonyl-ethyl)-[3-(2-methylamino-pyrimidin-4-yl)-imidazo[1,2-a]pyrazin-8-yl]-amine;
or a pharmaceutically acceptable salt of any of the foregoing compounds.

29. A compound selected from the group comprising:
Methyl-{3-[2-(tetrahydro-pyran-4-ylamino)-pyrimidin-4-yl]-imidazo[1,2-a]pyrazin-8-yl}-amine;
Methyl-[3-(2-methylamino-pyrimidin-4-yl)-imidazo[1,2-a]pyrazin-8-yl]-amine;
N1-{4-[8-(4-Methyl-piperazin-1-yl)-imidazo[1,2-a]pyrazin-3-yl]-pyrimidin-2-yl}-1-phenyl-ethane-1,2-diamine; hydrochloride;
N1-{4-[8-(4-Methyl-piperazin-1-yl)-imidazo[1,2-a]pyrazin-3-yl]-pyrimidin-2-yl}-1-phenyl-propane-1,3-diamine; hydrochloride;
N1-{6-[8-(4-Methyl-piperazin-1-yl)-imidazo[1,2-a]pyrazin-3-yl]-pyridin-2-yl}-1-phenyl-ethane-1,2-diamine; hydrochloride;
Benzyl-{6-[8-(4-methyl-piperazin-1-yl)-imidazo[1,2-a]pyrazin-3-yl]-pyridin-2-yl}-amine;
Benzyl-{4-[8-(4-methyl-piperazin-1-yl)-imidazo[1,2-a]pyrazin-3-yl]-pyrimidin-2-yl}-amine;
(2-Chloro-benzyl)-{4-[8-(4-methyl-piperazin-1-yl)-imidazo[1,2-a]pyrazin-3-yl]-pyrimidin-2-yl}-amine; hydrochloride;
(4-Chloro-benzyl)-{4-[8-(4-methyl-piperazin-1-yl)-imidazo[1,2-a]pyrazin-3-yl]-pyrimidin-2-yl}-amine; hydrochloride;
N1-{6-[8-(4-Methyl-piperazin-1-yl)-imidazo[1,2-a]pyrazin-3-yl]-pyridin-2-yl}-1-phenyl-propane-1,3-diamine; hydrochloride; and
{4-[8-(4-Methyl-piperazin-1-yl)-imidazo[1,2-a]pyrazin-3-yl]-pyrimidin-2-yl}-thiophen-3-ylmethyl-amine;
or a pharmaceutically acceptable salt of any of the foregoing compounds.

30. A compound selected from the group comprising:
1-(3-Chloro-phenyl)-N-1-{4-[8-(4-methyl-piperazin-1-yl)-imidazo[1,2-a]pyrazin-3-yl]-pyrimidin-2-yl}-propane-1,3-diamine; hydrochloride;
{4-[8-(4-Methyl-piperazin-1-yl)-imidazo[1,2-a]pyrazin-3-yl]-pyrimidin-2-yl}-thiophen-2-ylmethyl-amine; hydrochloride;
(2-Chloro-benzyl)-{6-[8-(4-methyl-piperazin-1-yl)-imidazo[1,2-a]pyrazin-3-yl]-pyridin-2-yl}-amine; hydrochloride;
(3-Chloro-benzyl)-{4-[8-(4-methyl-piperazin-1-yl)-imidazo[1,2-a]pyrazin-3-yl]-pyrimidin-2-yl}-amine; hydrochloride;
N-{3-[2-(3-Chloro-benzylamino)-pyrimidin-4-yl]-imidazo[1,2-a]pyrazin-8-yl}-cyclohexane-1,4-diamine; hydrochloride;
N-[3-(2-Benzylamino-pyrimidin-4-yl)-imidazo[1,2-a]pyrazin-8-yl]-cyclohexane-1,4-diamine; hydrochloride;
N1-{4-[8-(4-Methyl-piperazin-1-yl)-imidazo[1,2-a]pyrazin-3-yl]-pyrimidin-2-yl}-1-thiophen-3-yl-propane-1,3-diamine; hydrochloride;
(4-Chloro-benzyl)-{6-[8-(4-methyl-piperazin-1-yl)-imidazo[1,2-a]pyrazin-3-yl]-pyridin-2-yl}-amine; hydrochloride;
[3-(2-Benzylamino-pyrimidin-4-yl)-imidazo[1,2-a]pyrazin-8-yl]-(2-morpholin-4-yl-ethyl)-amine; hydrochloride;
N-[3-(6-Benzylamino-pyridin-2-yl)-imidazo[1,2-a]pyrazin-8-yl]-cyclohexane-1,4-diamine; hydrochloride;
N1-{4-[8-(4-Methyl-piperazin-1-yl)-imidazo[1,2-a]pyrazin-3-yl]-pyrimidin-2-yl}-1-thiophen-3-yl-ethane-1,2-diamine; hydrochloride;
N-{3-[2-(3-Amino-1-phenyl-propylamino)-pyrimidin-4-yl]-imidazo[1,2-a]pyrazin-8-yl}-cyclohexane-1,4-diamine; hydrochloride; and
N-{3-[2-(2-Amino-1-phenyl-ethylamino)-pyrimidin-4-yl]-imidazo[1,2-a]pyrazin-8-yl}-cyclohexane-1,4-diamine; hydrochloride;
or a pharmaceutically acceptable salt of any of the foregoing compounds.

31. A compound selected from the group comprising:
1-(3-Chloro-phenyl)-N-1-{4-[8-(4-methyl-piperazin-1-yl)-imidazo[1,2-a]pyrazin-3-yl]-pyrimidin-2-yl}-ethane-1,2-diamine; hydrochloride;
N-{3-[6-(2-Amino-1-phenyl-ethylamino)-pyridin-2-yl]-imidazo[1,2-a]pyrazin-8-yl}-cyclohexane-1,4-diamine; hydrochloride;
N-{3-[6-(3-Amino-1-phenyl-propylamino)-pyridin-2-yl]-imidazo[1,2-a]pyrazin-8-yl}-cyclohexane-1,4-diamine; hydrochloride;
N-{3-[6-(3-Chloro-benzylamino)-pyridin-2-yl]-imidazo[1,2-a]pyrazin-8-yl}-cyclohexane-1,4-diamine; hydrochloride;

N-{3-[2-(2-Chloro-benzylamino)-pyrimidin-4-yl]-imidazo[1,2-a]pyrazin-8-yl}-cyclohexane-1,4-diamine; hydrochloride;

N-(3-{6-[(Thiophen-3-ylmethyl)-amino]-pyridin-2-yl}-imidazo[1,2-a]pyrazin-8-yl)-cyclohexane-1,4-diamine; hydrochloride;

N-{3-[6-(2-Chloro-benzylamino)-pyridin-2-yl]-imidazo[1,2-a]pyrazin-8-yl}-cyclohexane-1,4-diamine; hydrochloride;

N-{3-[6-(4-Chloro-benzylamino)-pyridin-2-yl]-imidazo[1,2-a]pyrazin-8-yl}-cyclohexane-1,4-diamine; hydrochloride;

N-(3-{6-[(Thiophen-2-ylmethyl)-amino]-pyridin-2-yl}-imidazo[1,2-a]pyrazin-8-yl)-cyclohexane-1,4-diamine; hydrochloride;

{3-[2-(2-Chloro-benzylamino)-pyrimidin-4-yl]-imidazo[1,2-a]pyrazin-8-yl}-(2-morpholin-4-yl-ethyl)-amine; hydrochloride;

{3-[2-(3-Chloro-benzylamino)-pyrimidin-4-yl]-imidazo[1,2-a]pyrazin-8-yl}-(2-morpholin-4-yl-ethyl)-amine; hydrochloride;

1-(3-Chloro-phenyl)-N-1-{6-[8-(2-morpholin-4-yl-ethylamino)-imidazo[1,2-a]pyrazin-3-yl]-pyridin-2-yl}-propane-1,3-diamine hydrochloride; and 1-(3-Chloro-phenyl)-N-1-{6-[8-(2-morpholin-4-yl-ethylamino)-imidazo[1,2-a]pyrazin-3-yl]-pyridin-2-yl}-ethane-1,2-diamine hydrochloride;

or a pharmaceutically acceptable salt of any of the foregoing compounds.

32. A pharmaceutical composition comprising any of the compounds according to claim 1, or a pharmaceutically acceptable salt thereof, as an active ingredient and a pharmaceutically acceptable carrier or excipient.

* * * * *